United States Patent
Laga et al.

(10) Patent No.: US 9,920,303 B2
(45) Date of Patent: Mar. 20, 2018

(54) BRASSICA PLANTS COMPRISING MUTANT FAD3 ALLELES

(75) Inventors: Benjamin Laga, Wingene (BE); Peter Denolf, Velzeke (BE)

(73) Assignee: BAYER CROPSCIENCE NV, Diegem (BE)

(*) Notice: Subject to any disclaimer, the term of this patent is extended or adjusted under 35 U.S.C. 154(b) by 598 days.

(21) Appl. No.: 13/510,393

(22) PCT Filed: Nov. 19, 2010

(86) PCT No.: PCT/EP2010/007028
§ 371 (c)(1),
(2), (4) Date: Jun. 5, 2012

(87) PCT Pub. No.: WO2011/060946
PCT Pub. Date: May 26, 2011

(65) Prior Publication Data
US 2012/0246755 A1    Sep. 27, 2012

Related U.S. Application Data

(60) Provisional application No. 61/263,042, filed on Nov. 20, 2009.

(30) Foreign Application Priority Data

Nov. 23, 2009    (EP) .................................. 09075513

(51) Int. Cl.
*A01H 5/10* (2006.01)
*C12N 9/02* (2006.01)
*C12N 15/82* (2006.01)

(52) U.S. Cl.
CPC ....... *C12N 9/0083* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 5,750,827 A | 5/1998 | Debonte et al. | |
| 5,985,557 A | 11/1999 | Prudent et al. | |
| 6,001,567 A | 12/1999 | Brow et al. | |
| 7,736,884 B2* | 6/2010 | Gunnarsson et al. | 435/254.1 |
| 2003/0150020 A1* | 8/2003 | Somers | C12N 15/8247 800/281 |
| 2004/0083503 A1 | 4/2004 | Kodali et al. | |
| 2008/0034457 A1 | 2/2008 | DeBonte et al. | |

FOREIGN PATENT DOCUMENTS

| | | | |
|---|---|---|---|
| WO | WO 9418337 A1 * | 8/1994 | C12N 15/82 |
| WO | 0125453 | 4/2001 | |
| WO | 2004072259 | 8/2004 | |
| WO | 2006034059 | 3/2006 | |
| WO | 2006084352 | 8/2006 | |
| WO | 2009007091 | 1/2009 | |
| WO | 2011060946 | 5/2011 | |

OTHER PUBLICATIONS

Vrinten et al. Plant Physiol. 139(1):79-87. Sep. 2005.*
Hu et al. Mapping of the loci controlling oleic and linolenic acid contents and development of fad2 and fad3 allele-speciWc markers in canola (*Brassica napus* L.). Theor Appl Genet 113:497-507, 2006.*
Auld et al. Rapeseed Mutants with Reduced Levels of Polyunsaturated Fatty Acids and Increased Levels of Oleic Acid. Crop. Sci. 32:657-662. May 1992.*
Hu et al (Mapping of the loci controlling oleic and linolenic acid contents and development of fad2 and fad3 allele-speciWc markers in canola <*Brassica napus* L.>. Theor Appl Genet 113:497-507, 2006).*
Yadav et al, Plant Physiol. 103:467-476, 1993.*
Vrinten et al (Two FAD3 desaturase genes control the level of linolenic acid in flax seed. Plant Physiol. 139(1):79-87. Sep. 2005).*
Arondel et al, Science 258 (5086), 1353-1355 (1992).*
Auld et al (Rapeseed Mutants with Reduced Levels of Polyunsaturated Fatty Acids and Increased Levels of Oleic Acid. Crop Sci. 32:657-662, May 1992).*
GenBank Accession No. NM 128552, Submitted (Feb. 18, 2011) Department of Plant Biology, Carnegie Institution 260 Panama Street, Stanford, CA USA.
GenPep Accession No. ACS26169, Submitted (May 4, 2009) Sichuan University, Key Laboratory of Bio-Resources and Eco-Environment, 29 Wangjiang Street, Chengdu, Sichuan 610064, China.
P. Barret, et al., Low linolenic acid level in rapeseed can be easily assessed through the detection of two single base substitution in fad3 genes, 1999.
GenBank Accession No. FJ985689, Submitted (May 4, 2009) Sichuan University, Key Laboratory of Bio-Resources and Eco-Environment, 29 Wangjiang Street, Chengdu, Sichuan 610064, China.
MJ Burns, et al., QTL Analysis of an Intervarietal Set of Substitution Lines in *Brassica napus*(i) Seed oil content and fatty acid composition, Heredity (2003) 90, 39-48, Nature Publishing Group.
W. Diepenbrock, et al., Genetic Regulation of Linolenic Acid Concentration in Rapeseed, CropScience 1987, 27:75-77. (Abstract).
JJ Doyle, et al., A Rapid DNA Isolation Procedure for Small Quantities of Fresh Leaf Tissue, vol. 19, Issue: 1, pp. 11-15. (Abstract).
Steven Henikoff, et al., Tilling. Traditional Mutagenesis Meets Functional Genomics, Plant Physiology, Jun. 2004, vol. 135, pp. 630-636.
X. Hu et al., Mapping of the loci controlling oleic and linolenic acid contents and development of fad2 and fad3 allele-specific markers in canola (*Brassica napus* L.), Theor Appl Genet (2006) 113: 497-507.

(Continued)

Primary Examiner — Medina A Ibrahim
Assistant Examiner — Wayne Zhong
(74) Attorney, Agent, or Firm — Arent Fox LLP

(57) ABSTRACT

The present invention relates to *Brassica* plants comprising mutant FAD3 alleles, FAD3 nucleic acid sequences and proteins, as well as methods for generating and identifying said plants and alleles, which can be used to obtain seed oil with a reduced alpha-linolenic acid content.

26 Claims, No Drawings

(56) References Cited

OTHER PUBLICATIONS

C. Jourdren, et al., Identification of RAPD markers linked to linolenic acid genes in rapeseed, 1996 Kluwer Academic Publishers, Euphytica, 90: 351-357. 1996.

C. Jourdren, et al., Specific molecular marker of the genes controlling linolenic acid content in rapeseed, Theor Appl Genet (1996) 93: 512-518.

GenBank Accession No. L22962, Jan. 31, 1995.

X. Li, et al., A fast neutron deletion mutagenesis-based reverse genetics system for plants, The Plant Journal (2001) 27(3), 235-242.

X. Li, et al., Reverse genetics by fast neutron mutagenesis in higher plants, Funct Integr Genomics (2002) 2:254-258.

C.M. McCallum, et al., Targeting Induced Local Lesions IN Genomes (TILLING) for Plant Functional Genomics, Plant Physiology, Jun. 2000, vol. 123, pp. 439-442.

C.M. McCallum, et al., Targeted Screening for Induced Mutations, 2000 Nature America, Inc., vol. 18.

A. McCartney, et al., Membrane-found fatty acid desaturases are inserted co-translationally into the ER and contain different ER retrieval motifs at their carboxy termini, The Plant Journal (2004) 37, 156-173.

S.B. Needleman, et al., A General Method Applicable to the Search for Similarities in the Amino Acid Sequence of Two Proteins, J. Mol. Biol. (1970) 48, 443-453.

A.S. Reddy, et al., Isolation of a delta 6-desaturase gene from the cyanobacterium *Synechocystis* sp. strain PCC 6803 by gain-of-function expression in *Anabaena* sp. strain PCC 7120, Plant Molecular Biology 27: 293-300, 1993.

D.W. W Reed, et al., Characterization of the *Brassica napus* Extraplastidial Linoleate Desaturase by Expression in *Saacharomyces cerevisiae*, Plant Physiology, Mar. 2000, vol. 122, pp. 715-720.

P. Rice, et al., EMBOSS: The European Molecular Biology Open Software Suite, TIG Jun. 2000, vol. 16, No. 6.

J. Shanklin, et al., Eight Histidine Residues are Catalytically Essential in a Membrane-Associated Iron Enzyme, Stearoyl-CoA Desaturase, and Are Conserved in Alkane Hydroxylase and Xylene Monooxygenase, Biochemistry 1994, 33, 12787-12794.

R.J. Snowdon, Cytogenetics and genome analysis in *Brassica* crops, Chromosome Research 2007, 15:85-95.

P. Vrinten, et al., Two FAD3 Desaturase Genes Control the Level of Linolenic Acid in Flax Seed, Plant Physiology, Sep. 2005, vol. 139, pp. 79-87.

\* cited by examiner

SEQUENCE LISTING

```
<160> NUMBER OF SEQ ID NOS: 37

<210> SEQ ID NO 1
<211> LENGTH: 2985
<212> TYPE: DNA
<213> ORGANISM: Brassica napus
<220> FEATURE:
<221> NAME/KEY: CDS
<222> LOCATION: (1)..(281)
<220> FEATURE:
<221> NAME/KEY: CDS
<222> LOCATION: (838)..(927)
<220> FEATURE:
<221> NAME/KEY: CDS
<222> LOCATION: (1463)..(1529)
<220> FEATURE:
<221> NAME/KEY: CDS
<222> LOCATION: (1931)..(2023)
<220> FEATURE:
<221> NAME/KEY: CDS
<222> LOCATION: (2128)..(2313)
<220> FEATURE:
<221> NAME/KEY: CDS
<222> LOCATION: (2391)..(2471)
<220> FEATURE:
<221> NAME/KEY: CDS
<222> LOCATION: (2559)..(2696)
<220> FEATURE:
<221> NAME/KEY: CDS
<222> LOCATION: (2791)..(2985)

<400> SEQUENCE: 1 atg gtt gtc gct atg gac cag cgt agc aat gcg aac gga gac gaa agg     48
Met Val Val Ala Met Asp Gln Arg Ser Asn Ala Asn Gly Asp Glu Arg
1               5                   10                  15
```

| | |
|---|---|
| ttt gat ccg agc gca caa cca ccg ttc aag atc gga gat ata agg gcg<br>Phe Asp Pro Ser Ala Gln Pro Pro Phe Lys Ile Gly Asp Ile Arg Ala<br>       20                     25                30 | 96 |
| gcc att cct aag cat tgt tgg gta aag agt cct ttg aga tcc atg agc<br>Ala Ile Pro Lys His Cys Trp Val Lys Ser Pro Leu Arg Ser Met Ser<br>       35                     40                45 | 144 |
| tat gtc gcc aga gac att ttc gcc gtc gtg gct ctt gcc gtc gcc gcc<br>Tyr Val Ala Arg Asp Ile Phe Ala Val Val Ala Leu Ala Val Ala Ala<br>50                     55                     60 | 192 |
| gtg tat ttt gat agc tgg ttc ttt tgg cct ctt tat tgg gcc gcc caa<br>Val Tyr Phe Asp Ser Trp Phe Phe Trp Pro Leu Tyr Trp Ala Ala Gln<br>65                     70                     75                80 | 240 |
| gga acc ctg ttc tgg gct atc ttc gta ctc ggc cac gac tg<br>Gly Thr Leu Phe Trp Ala Ile Phe Val Leu Gly His Asp Cys<br>               85                     90 | 281 |
| gtaatttaat ttttctttca acttcttaat tttgatatgt ttatatgttt ttttcgtttt | 341 |
| ttgcattgtc tttgatttct tgaccgtacg ttcgatatga gattttcact gacttcaaga | 401 |
| tttgattctc ttcaggttta cttttttcaa ttttaattat tatgttcacc caatttggcc | 461 |
| tattttaaaa gcaaaagggg atctaagatt tttaattctt tgtttttttt ttgttctttt | 521 |
| tcattagtcg taacactcct aactaaacat ctttttcttt cctataatta ctgttgtttc | 581 |
| cgcattttat ggatctacgt ttgaaatttt caataaacac acattttatt gttttctgta | 641 |
| acaatttaat tactgtatat tggttctttt aattattgtg tgttgttcca atctattttc | 701 |
| gaaatatagt catgtgacac gtcatattct attttgtta ccttgttgaa acgtttgaat | 761 |
| tgagtaaagt tcagttaaca ttgtgcaata atgataaat gtgtttatga tgtaaaattt | 821 |
| aatttgaata atacag t gga cat ggg agc ttc tca gac att cct ctt ctg<br>                         Gly His Gly Ser Phe Ser Asp Ile Pro Leu Leu<br>                         95                      100                  105 | 871 |
| aat act gcg gtt ggt cat att ctt cat tcc ttc att ctc gtt cca tac<br>Asn Thr Ala Val Gly His Ile Leu His Ser Phe Ile Leu Val Pro Tyr<br>           110                     115                   120 | 919 |
| cat ggt tg gtaagtcatt tatttaact tctttttca tgcaaattta<br>His Gly Trp | 967 |
| ttcttgtttt cgtatttctt acatttttcct tgtcattctt ggtgcatgtt agcaaacagt | 1027 |
| aatctgataa ctgaaaatat attaattttt catagtaaaa taatgcatgt gactaaaagt | 1087 |
| ctaaaagcat caaaatcttt agcatccatg aaaaaagaac aaaactttta tttaatgcta | 1147 |
| tgggcctatt tatggtccaa ttagctatta tcatatgaca tgtccttgaa taaattaatg | 1207 |
| tataagttta ataatattta tatttttg ttttaatggc ttattttatt gttaaatgga | 1267 |
| tacatcagct tgaaatatct atgaacatgc atcattttcc taagatacat ttgtttgttg | 1327 |
| ctcaaaaaat aaataactag ttaaacgagt gagattctta gcatctgcct cgaaaacgat | 1387 |
| atgttattga caattccaat ttcatttta tgaaaataaa ataatagttt attttataat | 1447 |
| tgggggttggt tgcag g aga ata agc cat cgg aca cac cac cag aac cat<br>                     Arg Ile Ser His Arg Thr His His Gln Asn His<br>                      125                     130                   135 | 1496 |
| ggc cat gtt gaa aac gac gag tct tgg gtt ccg gtaatctttc cctctctcat<br>Gly His Val Glu Asn Asp Glu Ser Trp Val Pro<br>           140                     145 | 1549 |
| atttttttc ttttttttgaa attctttcat tttaattttc ttaggattct atgtatttat | 1609 |
| ttaaatcaat ccttttttcca gtttgaggct tggacgacca cttgtcagat tcgtcgttta | 1669 |
| gctgtagtaa acaactgatt taaattgttt atagtactgt agttaacttt aacaacgggc | 1729 |

```
cacttatatt cgagccattg gcataaaatg attcttctcg aaattcgttt acttttctta    1789
gtatttttca gttttggagt ttacgtagaa ctaataaaaa taaattttg tataaacata     1849 ccacatgcaa tgaataaatt cgaatatata accatactgt taaatattaa ttaacatttt    1909
aatcttaatt ttgcattcca g ttg cca gaa aaa tta tac aag aat ttg tcc      1960
                         Leu Pro Glu Lys Leu Tyr Lys Asn Leu Ser
                                     150                 155 cac agt aca cgg atg ctc aga tac act gtc cct ctc ccc atg ctc gct      2008
His Ser Thr Arg Met Leu Arg Tyr Thr Val Pro Leu Pro Met Leu Ala
            160                 165                 170 tac cct ctc tat ctg gtaaatccta attcctaatt ttcttcctga ttataattac      2063
Tyr Pro Leu Tyr Leu
        175 aattttgaat ttttagattt tgagtattaa ctaaatataa attaatgttt ggggatgact    2123 acag tgg tac aga agt cct ggt aaa gaa ggg tca cat tat aac cca tac     2172
     Trp Tyr Arg Ser Pro Gly Lys Glu Gly Ser His Tyr Asn Pro Tyr
                 180                 185                 190 agt agt tta ttt gct cca agc gag aga aag ctt att gca act tca act      2220
Ser Ser Leu Phe Ala Pro Ser Glu Arg Lys Leu Ile Ala Thr Ser Thr
            195                 200                 205 act tgc tgg tcg atc atg ttg gcc act ctt gtt tat cta tca ttc ctc      2268
Thr Cys Trp Ser Ile Met Leu Ala Thr Leu Val Tyr Leu Ser Phe Leu
            210                 215                 220 gtt ggt cca gtc aca gtt ctc aaa gtc tat gga gtt cct tac att          2313
Val Gly Pro Val Thr Val Leu Lys Val Tyr Gly Val Pro Tyr Ile
225                 230                 235 gtaagtttca tatattacat tattatatca ttgctaataa aatttgtttt tgacataaag    2373
ttttggaaaa atttcag atc ttt gta atg tgg ttg gac gct gtc acg tac       2423
                   Ile Phe Val Met Trp Leu Asp Ala Val Thr Tyr
                           240                 245                 250 ttg cat cat cat ggt cac gat gat aag ttg cct tgg tac aga ggc aag      2471
Leu His His His Gly His Asp Asp Lys Leu Pro Trp Tyr Arg Gly Lys
            255                 260                 265 gtaagtagat caacattaat ttataagaag caataatgat tagtatttga ttaatctaaa    2531
ttattgatgt tttgtataca ataatag gaa tgg agt tat tta cgt gga gga tta    2585
                              Glu Trp Ser Tyr Leu Arg Gly Gly Leu
                                                  270                 275 aca act att gat aga gat tac ggg atc ttc aac aac att cat cac gat      2633
Thr Thr Ile Asp Arg Asp Tyr Gly Ile Phe Asn Asn Ile His His Asp
            280                 285                 290 att gga act cac gtg atc cat cat ctt ttc cca caa atc cct cac tat      2681
Ile Gly Thr His Val Ile His His Leu Phe Pro Gln Ile Pro His Tyr
            295                 300                 305 cac ttg gtc gat gcc gtgagtgatc tcgctctctc tctagttcca tttgattaaa      2736
His Leu Val Asp Ala
        310 attaaagggt gattaattac taaattagtg atcttaatta atgatatgcg acag acg      2793
                                                              Thr aaa gca gct aaa cat gtg ttg gga aga tac tac aga gaa cca aag acg      2841
Lys Ala Ala Lys His Val Leu Gly Arg Tyr Tyr Arg Glu Pro Lys Thr
    315                 320                 325 tca gga gca ata ccg atc cac ttg gtg gaa agt ttg gtg gca agt att      2889
Ser Gly Ala Ile Pro Ile His Leu Val Glu Ser Leu Val Ala Ser Ile
330                 335                 340                 345 aag aaa gat cat tac gtc agt gac act ggt gat att gtc ttc tac gag      2937
Lys Lys Asp His Tyr Val Ser Asp Thr Gly Asp Ile Val Phe Tyr Glu
            350                 355                 360
```

```
aca gat cca gat ctc tac gtt tat gct tct gac aaa tcc aaa atc aac    2985
Thr Asp Pro Asp Leu Tyr Val Tyr Ala Ser Asp Lys Ser Lys Ile Asn
        365                 370                 375
```

<210> SEQ ID NO 2
<211> LENGTH: 377
<212> TYPE: PRT
<213> ORGANISM: Brassica napus

<400> SEQUENCE: 2

```
Met Val Val Ala Met Asp Gln Arg Ser Asn Ala Asn Gly Asp Glu Arg
1               5                   10                  15

Phe Asp Pro Ser Ala Gln Pro Pro Phe Lys Ile Gly Asp Ile Arg Ala
            20                  25                  30

Ala Ile Pro Lys His Cys Trp Val Lys Ser Pro Leu Arg Ser Met Ser
        35                  40                  45

Tyr Val Ala Arg Asp Ile Phe Ala Val Ala Leu Ala Val Ala Ala
    50                  55                  60

Val Tyr Phe Asp Ser Trp Phe Trp Pro Leu Tyr Trp Ala Ala Gln
65                  70                  75                  80

Gly Thr Leu Phe Trp Ala Ile Phe Val Leu Gly His Asp Cys Gly His
                85                  90                  95

Gly Ser Phe Ser Asp Ile Pro Leu Leu Asn Thr Ala Val Gly His Ile
            100                 105                 110

Leu His Ser Phe Ile Leu Val Pro Tyr His Gly Trp Arg Ile Ser His
        115                 120                 125

Arg Thr His His Gln Asn His Gly His Val Glu Asn Asp Glu Ser Trp
    130                 135                 140

Val Pro Leu Pro Glu Lys Leu Tyr Lys Asn Leu Ser His Ser Thr Arg
145                 150                 155                 160

Met Leu Arg Tyr Thr Val Pro Leu Pro Met Leu Ala Tyr Pro Leu Tyr
                165                 170                 175

Leu Trp Tyr Arg Ser Pro Gly Lys Glu Gly Ser His Tyr Asn Pro Tyr
            180                 185                 190

Ser Ser Leu Phe Ala Pro Ser Glu Arg Lys Leu Ile Ala Thr Ser Thr
        195                 200                 205

Thr Cys Trp Ser Ile Met Leu Ala Thr Leu Val Tyr Leu Ser Phe Leu
    210                 215                 220

Val Gly Pro Val Thr Val Leu Lys Val Tyr Gly Val Pro Tyr Ile Ile
225                 230                 235                 240

Phe Val Met Trp Leu Asp Ala Val Thr Tyr Leu His His His Gly His
                245                 250                 255

Asp Asp Lys Leu Pro Trp Tyr Arg Gly Lys Glu Trp Ser Tyr Leu Arg
            260                 265                 270

Gly Gly Leu Thr Thr Ile Asp Arg Asp Tyr Gly Ile Phe Asn Asn Ile
        275                 280                 285

His His Asp Ile Gly Thr His Val Ile His His Leu Phe Pro Gln Ile
    290                 295                 300

Pro His Tyr His Leu Val Asp Ala Thr Lys Ala Ala Lys His Val Leu
305                 310                 315                 320

Gly Arg Tyr Tyr Arg Glu Pro Lys Thr Ser Gly Ala Ile Pro Ile His
                325                 330                 335

Leu Val Glu Ser Leu Val Ala Ser Ile Lys Lys Asp His Tyr Val Ser
            340                 345                 350

Asp Thr Gly Asp Ile Val Phe Tyr Glu Thr Asp Pro Asp Leu Tyr Val
```

```
                355                 360                 365
Tyr Ala Ser Asp Lys Ser Lys Ile Asn
    370                 375

<210> SEQ ID NO 3
<211> LENGTH: 3555
<212> TYPE: DNA
<213> ORGANISM: Brassica napus
<220> FEATURE:
<221> NAME/KEY: CDS
<222> LOCATION: (1)..(290)
<220> FEATURE:
<221> NAME/KEY: CDS
<222> LOCATION: (882)..(971)
<220> FEATURE:
<221> NAME/KEY: CDS
<222> LOCATION: (2032)..(2098)
<220> FEATURE:
<221> NAME/KEY: CDS
<222> LOCATION: (2499)..(2591)
<220> FEATURE:
<221> NAME/KEY: CDS
<222> LOCATION: (2700)..(2885)
<220> FEATURE:
<221> NAME/KEY: CDS
<222> LOCATION: (2964)..(3044)
<220> FEATURE:
<221> NAME/KEY: CDS
<222> LOCATION: (3130)..(3267)
<220> FEATURE:
<221> NAME/KEY: CDS
<222> LOCATION: (3361)..(3555)

<400> SEQUENCE: 3
```

```
atg gtt gtc gct atg gac cag cgt agc aat gtg aac gga gat tcc aag     48
Met Val Val Ala Met Asp Gln Arg Ser Asn Val Asn Gly Asp Ser Lys
1               5                   10                  15 gac gaa agg ttt gat ccg agc gca caa cca ccg ttt aag atc gga gat     96
Asp Glu Arg Phe Asp Pro Ser Ala Gln Pro Pro Phe Lys Ile Gly Asp
            20                  25                  30 ata agg gct gcg att cct aag cat tgt tgg gtc aag agt cct ttg aga    144
Ile Arg Ala Ala Ile Pro Lys His Cys Trp Val Lys Ser Pro Leu Arg
        35                  40                  45 tcc atg agc tac gtc gcg aga gac att ttc tcc gtc gtg gct ctg gcc    192
Ser Met Ser Tyr Val Ala Arg Asp Ile Phe Ser Val Val Ala Leu Ala
    50                  55                  60 gtc gcc gcc gtg tat ttt gat agc tgg ttc ttc tgg cct ctt tat tgg    240
Val Ala Ala Val Tyr Phe Asp Ser Trp Phe Phe Trp Pro Leu Tyr Trp
65                  70                  75                  80 gcc gcc caa gga acc ctt ttc tgg gcc atc ttc gta ctc ggc cac gac    288
Ala Ala Gln Gly Thr Leu Phe Trp Ala Ile Phe Val Leu Gly His Asp
                85                  90                  95 tg  gtaatttaat tttcaattta ttttttcttc aacttcttaa ttttgatatg          340
Cys tttatatgtt tttttcgttt tttgcatcgt ctttgatttc ttgaacgcac gttcgatatg    400
agattttcac tgacttcaag atttgattct cttcaggttt acttttaaaa aaaaaaatta    460
ttatgttcac ccaaattggc ctattttaaa agcaaagggg atctaagat ttttaattct     520 tctctttttc agtcgtaaca ctgctaactt ttttttttga tcaaatcgta acactcataa    580
gtcctaacta aacatctttt tctttcctat aattattgtt ggttccgcat tttatggatc    640
tacgtttgaa agtttcaata aaacacattt tattgtttga agtaacaat ataattactg     700 tatattgatt cttttaatta ttgtgtgttg ttccaatcta ctttcgaaat atagtcatgt    760
gacacgtcat attctatttt tgttaccttg ttggaacgtt tgaattgagt aaagtttaat    820
```

```
taacattgtg caataaatga taaacatgtt tatgatgtaa aattcaattt gaataataca      880 g t gga cat ggg agc ttc tca gac att cct ctt ctg aat act gcg gtt       927
    Gly His Gly Ser Phe Ser Asp Ile Pro Leu Leu Asn Thr Ala Val
        100                 105                 110 ggt cat att ctt cat tcc ttc att ctc gtt cca tac cat ggt tg            971
Gly His Ile Leu His Ser Phe Ile Leu Val Pro Tyr His Gly Trp
        115                 120                 125 gtaagtcatt tatttaaaca tcttttttcat gcaaatttat tcttgttttc gtatttctta   1031
cattttcctt gtcattcttg gtgcatgtta gcaaactgta atctgataac tgaaaatata   1091
ttaattttcc atagtaaaat aatgcatgtg actaaaagca tcaaaatctt tagcatcgaa   1151
gaaaaaagaa ccaaactttt atttaatgct atgggcctat ttatggtcca attagctatt   1211
atcatatgac atgtccttga ataaattaat gtagcttcat atgtgagttt aataatattt   1271 atatatttt gttttaatgg cttatttat tgttaaatgg atacatcagc ttgaaatgtc     1331
tacgaacatg catcattttc ctagatacac ttgtttgttg ctcaaaaatg aataacttag   1391
ttaaacgagt gagcatgttc tatggggttt cttagagcat gattattgag aagttcctag   1451
agtgaggttt ttaccggaat ataagaatct atctcttaac ttttaactaa aaaaattaag   1511
aaccggcttt taaaactcgt atttaagaac cgttttttag ttttttagtt aaaaatcaag   1571
agacgagttc ttatattccg ctaagaactc caccctgaga acttctcaat aatcatgctc   1631
ttagtgctct aagaagggtc cttaacaaaa tattaataat aagatatagt gtgggcccaa   1691
aaaaaaacaa aaaccggtt acaaaagtcg cgaaagaagg atcgattttg gtctttact    1751 tgtactgttt gtggatccca ctggtggtgg tccgcgattg gtttcttttt taatttaatt   1811 tatttttta atcggagaaa aaattaaga aaccaaaaac agttttaatc atggcctcat    1871
gttggggttg agttttatat tctgataaga atcccatctt aaaaacccg ttaaacatgc    1931 tcttaccatc tgcttcgaaa atgatatgtt attgacaatt ccaatttcat ttttatgaaa   1991
ataaaataat agtttatttt ataactgagg gtggttgcag g aga ata agc cat cgg   2047
                                             Arg Ile Ser His Arg
                                                     130 aca cac cac cag aac cat ggc cat gtt gaa aac gac gag tct tgg gtt      2095
Thr His His Gln Asn His Gly His Val Glu Asn Asp Glu Ser Trp Val
        135                 140                 145 ccg gtaatctttc cctctctcat atttttttc tttttttga aattctttca              2148
Pro ttttaatttt cttaggattc tatgtattta ttttaatcaa tccttttcc agtttgaggc    2208 taggacgacc acttgtcaga tttgtcgttt agctgtagta aacaactgat ttaaattgtt   2268
tatagtactg tagttaactt taacaacgga ccactatat tcgagccatt ggcataaaat    2328
gattcttctc gaaattcgtt tacttttctt agtattttc aattttggag tttacgtaga    2388
actaataaaa agaaaaactt ataaacacac cacatgcaat gaataaattc gaatatataa   2448
ccatactgtt aaatattaat ttacatttta atcttaattt tgcattccag ttg cca      2504
                                                          Leu Pro
                                                              150 gaa aaa tta tac aag aat ttg tcc cac agt aca cgg atg ctc aga tac      2552
Glu Lys Leu Tyr Lys Asn Leu Ser His Ser Thr Arg Met Leu Arg Tyr
        155                 160                 165 act gtc cct ctc ccc atg ctc gct tac cct ctc tat ctg gtaaatccta       2601
Thr Val Pro Leu Pro Met Leu Ala Tyr Pro Leu Tyr Leu
        170                 175                 180 attcctaatt tttcttcctg attataatta caattttgaa tttttagatt ttgagtatta   2661
```

```
actaaatata aattaaattt gtttggggat gactacag tgg tac aga agt cct ggt    2717
                                         Trp Tyr Arg Ser Pro Gly
                                                         185 aaa gaa ggg tca cat tat aac cca tac agt agt tta ttt gcc cca agc    2765
Lys Glu Gly Ser His Tyr Asn Pro Tyr Ser Ser Leu Phe Ala Pro Ser
            190                 195                 200 gag aga aag ctt att gca act tca act act tgc tgg tcg atc gtg ttg    2813
Glu Arg Lys Leu Ile Ala Thr Ser Thr Thr Cys Trp Ser Ile Val Leu
        205                 210                 215 gcc act ctt gtt tat cta tca ttc ctc gtt ggt cca gtc aca gtt cta    2861
Ala Thr Leu Val Tyr Leu Ser Phe Leu Val Gly Pro Val Thr Val Leu
    220                 225                 230 aaa gtc tat ggt gtt cct tac att gtaagtttca tatttctt tattatatca    2915
Lys Val Tyr Gly Val Pro Tyr Ile
235                 240 ttgctaatat aatttgtttt tgacataaaa gttttggaaa aatttcag atc ttt gta    2972
                                                    Ile Phe Val
                                                            245 atg tgg ttg gac gct gtc acg tac ttg cat cat cat ggt cac gat gat    3020
Met Trp Leu Asp Ala Val Thr Tyr Leu His His His Gly His Asp Asp
                250                 255                 260 aag ctg cct tgg tac aga ggc aag gtaagtagat caacattatt tataagaagc    3074
Lys Leu Pro Trp Tyr Arg Gly Lys
            265 aataatgatt agtagttgaa taatctgaat ttttgatgtt tttgtacaat aatag gaa    3132
                                                            Glu
                                                            270 tgg agt tat tta cgt gga gga tta aca act gtt gat aga gat tac ggg    3180
Trp Ser Tyr Leu Arg Gly Gly Leu Thr Thr Val Asp Arg Asp Tyr Gly
                275                 280                 285 atc ttc aac aac att cat cac gat att gga act cac gtg atc cat cat    3228
Ile Phe Asn Asn Ile His His Asp Ile Gly Thr His Val Ile His His
            290                 295                 300 ctt ttc cca caa atc cct cac tat cac ttg gtc gat gcc gtgagtgatc    3277
Leu Phe Pro Gln Ile Pro His Tyr His Leu Val Asp Ala
305                 310                 315 tcgctctctc tctagtttca tttgattata ttaaagggtg attaattact aaattagtga    3337
tcttaattaa tgacatgcga cag acg aaa gca gct aaa cat gtg ttg gga aga    3390
                        Thr Lys Ala Ala Lys His Val Leu Gly Arg
                                320                 325 tac tac aga gaa cca aag acg tca gga gca ata ccg atc cac tta gtg    3438
Tyr Tyr Arg Glu Pro Lys Thr Ser Gly Ala Ile Pro Ile His Leu Val
                330                 335                 340 gaa agt ttg gtg gca agt att aag aaa gat cat tac gtc agt gac act    3486
Glu Ser Leu Val Ala Ser Ile Lys Lys Asp His Tyr Val Ser Asp Thr
            345                 350                 355 ggt gat att gtc ttc tac gag aca gat cca gat ctc tac gtt tat gct    3534
Gly Asp Ile Val Phe Tyr Glu Thr Asp Pro Asp Leu Tyr Val Tyr Ala
        360                 365                 370 tct gac aaa tcc aaa atc aat                                          3555
Ser Asp Lys Ser Lys Ile Asn
    375                 380

<210> SEQ ID NO 4
<211> LENGTH: 380
<212> TYPE: PRT
<213> ORGANISM: Brassica napus

<400> SEQUENCE: 4
```

```
Met Val Val Ala Met Asp Gln Arg Ser Asn Val Asn Gly Asp Ser Lys
1               5                   10                  15

Asp Glu Arg Phe Asp Pro Ser Ala Gln Pro Pro Phe Lys Ile Gly Asp
            20                  25                  30

Ile Arg Ala Ala Ile Pro Lys His Cys Trp Val Lys Ser Pro Leu Arg
            35                  40                  45

Ser Met Ser Tyr Val Ala Arg Asp Ile Phe Ser Val Val Ala Leu Ala
        50                  55                  60

Val Ala Ala Val Tyr Phe Asp Ser Trp Phe Trp Pro Leu Tyr Trp
65                  70                  75                  80

Ala Ala Gln Gly Thr Leu Phe Trp Ala Ile Phe Val Leu Gly His Asp
                85                  90                  95

Cys Gly His Gly Ser Phe Ser Asp Ile Pro Leu Leu Asn Thr Ala Val
            100                 105                 110

Gly His Ile Leu His Ser Phe Ile Leu Val Pro Tyr His Gly Trp Arg
            115                 120                 125

Ile Ser His Arg Thr His His Gln Asn His Gly His Val Glu Asn Asp
    130                 135                 140

Glu Ser Trp Val Pro Leu Pro Glu Lys Leu Tyr Lys Asn Leu Ser His
145                 150                 155                 160

Ser Thr Arg Met Leu Arg Tyr Thr Val Pro Leu Pro Met Leu Ala Tyr
                165                 170                 175

Pro Leu Tyr Leu Trp Tyr Arg Ser Pro Gly Lys Glu Gly Ser His Tyr
            180                 185                 190

Asn Pro Tyr Ser Ser Leu Phe Ala Pro Ser Glu Arg Lys Leu Ile Ala
            195                 200                 205

Thr Ser Thr Thr Cys Trp Ser Ile Val Leu Ala Thr Leu Val Tyr Leu
    210                 215                 220

Ser Phe Leu Val Gly Pro Val Thr Val Leu Lys Val Tyr Gly Val Pro
225                 230                 235                 240

Tyr Ile Ile Phe Val Met Trp Leu Asp Ala Val Thr Tyr Leu His His
                245                 250                 255

His Gly His Asp Asp Lys Leu Pro Trp Tyr Arg Gly Lys Glu Trp Ser
            260                 265                 270

Tyr Leu Arg Gly Gly Leu Thr Thr Val Asp Arg Asp Tyr Gly Ile Phe
    275                 280                 285

Asn Asn Ile His His Asp Ile Gly Thr His Val Ile His His Leu Phe
    290                 295                 300

Pro Gln Ile Pro His Tyr His Leu Val Asp Ala Thr Lys Ala Ala Lys
305                 310                 315                 320

His Val Leu Gly Arg Tyr Tyr Arg Glu Pro Lys Thr Ser Gly Ala Ile
                325                 330                 335

Pro Ile His Leu Val Glu Ser Leu Val Ala Ser Ile Lys Lys Asp His
            340                 345                 350

Tyr Val Ser Asp Thr Gly Asp Ile Val Phe Tyr Glu Thr Asp Pro Asp
    355                 360                 365

Leu Tyr Val Tyr Ala Ser Asp Lys Ser Lys Ile Asn
    370                 375                 380

<210> SEQ ID NO 5
<211> LENGTH: 4512
<212> TYPE: DNA
<213> ORGANISM: Brassica napus
<220> FEATURE:
<221> NAME/KEY: CDS
```

```
<222> LOCATION: (1)..(299)
<220> FEATURE:
<221> NAME/KEY: CDS
<222> LOCATION: (923)..(1012)
<220> FEATURE:
<221> NAME/KEY: CDS
<222> LOCATION: (1683)..(1749)
<220> FEATURE:
<221> NAME/KEY: CDS
<222> LOCATION: (3451)..(3543)
<220> FEATURE:
<221> NAME/KEY: CDS
<222> LOCATION: (3650)..(3835)
<220> FEATURE:
<221> NAME/KEY: CDS
<222> LOCATION: (3921)..(4001)
<220> FEATURE:
<221> NAME/KEY: CDS
<222> LOCATION: (4096)..(4233)
<220> FEATURE:
<221> NAME/KEY: CDS
<222> LOCATION: (4318)..(4512)

<400> SEQUENCE: 5 atg gtt gtt gct atg gac cag cgc agc aat gtt aac gga gat tcc ggt       48
Met Val Val Ala Met Asp Gln Arg Ser Asn Val Asn Gly Asp Ser Gly
1               5                   10                  15 gcc cgg aag gaa gaa ggg ttt gat cca agc gaa caa cca ccg ttt aag       96
Ala Arg Lys Glu Glu Gly Phe Asp Pro Ser Glu Gln Pro Pro Phe Lys
            20                  25                  30 atc gga gat atc agg gcg gcg att cct aag cat tgt tgg gtg aag agt      144
Ile Gly Asp Ile Arg Ala Ala Ile Pro Lys His Cys Trp Val Lys Ser
        35                  40                  45 cct ttg aga tct atg agc tac gtc gcc aga gac att ttc gcc gtc gcg      192
Pro Leu Arg Ser Met Ser Tyr Val Ala Arg Asp Ile Phe Ala Val Ala
    50                  55                  60 gct ctg gcc atg gcc gcc gtg tat ttt gat agc tgg ttc ctc tgg cca      240
Ala Leu Ala Met Ala Ala Val Tyr Phe Asp Ser Trp Phe Leu Trp Pro
65                  70                  75                  80 ctc tac tgg gtt gcc caa gga acc ctt ttc tgg gcc atc ttc gtt ctt      288
Leu Tyr Trp Val Ala Gln Gly Thr Leu Phe Trp Ala Ile Phe Val Leu
                85                  90                  95 ggc cac gac tg  gtaaattaaa ttttctgttt taattatttt gactcttttt          339
Gly His Asp Cys gttcaattta ttaatttctt gaatgcacgt tcgatgagta tcgtcgtcac tgacttcaag    399
atttaattct tttgaggtta cctttttcatg ttcaattatt aaaaaaataa aataaaatat    459
aggatctaag atttttttct tcatcagttc aagcatcatc actcatcagt cgtaagactc    519
gtaacaaaat atcttctttt ctataattaa tattatttcc gcatttaatg gatctacgtt    579
ttgatgttct caaattttgt ttctctttct ctagatcccc ggaactttta attataatta    639
tagtatagta taatatcaag aaaatatact gtttattttt tttggcaaca aatatattac    699
tcttgtttct ttgacaagaa aaaatatatt gttttttttct tcttttttgtg ttccaatcta   759 ttttcgagat ttagacaagt gacacgtcat ataccggatt tgttaccttg ttaaagagtt    819
tgggttaaaa caaatgtaga aaagttaaaa taaattgtgc aataaatgat aaatacgttt    879
ttatgttaaa caatgatgtg aaaataaaat tgaataatgg cag t gga cat ggg agt    935
                                                Gly His Gly Ser ttt tca gac att cct ctg ctg aac agt gtg gtt ggt cac att ctt cat      983
Phe Ser Asp Ile Pro Leu Leu Asn Ser Val Val Gly His Ile Leu His
105                 110                 115                 120 tca ttc atc ctc gtt cct tac cat ggt tg  gtaagtcatt tattaactat       1032
Ser Phe Ile Leu Val Pro Tyr His Gly Trp
```

```
            125
ttccatgtaa actattagta cttgttttcg tatttcttac attttcgttt gtcattcttc    1092
ttgggtgcat gctagcaaac tgtaatcagt attaactggg aactaccaac tgttttttt     1152 tgctagagta gcaattttat aattaaataa gaatcctatt aaacaatgca tgtgacaata    1212
tgaggttgct tttctgttca aaacaaatct ttagaagcca atgaaaaaga atccaaaact    1272
ttttttaaat gatatgcgcc tatctattgg tcctgactcc tgagttttct tactttctta    1332
agtataatta gattttgatt ttttttatag gttttcacta ttgttatttg tttacatcag    1392
cttcagatat cttcgaaaaa gatttacatg catcaatttc atgaggattt atagtttttc    1452
ttttacttat ttccgacaca atgtttagta gtaaaaagca ttaaatgttt ttttgctcaa    1512
aaaaaaagaa tgggattgtt agagcactct attgttagtt gttcaataaa tataccaact    1572
aaaaaaacaa aataaatata aaatgagtga gattgttaaa tcattataga gacaatttca    1632
ttttcacaaa aataaataaa tacataactt tttataattg gggtttgcag g aga ata      1689
                                                         Arg Ile agc cat cgg aca cac cac cag aac cat ggc cat gtt gaa aac gac gag      1737
Ser His Arg Thr His His Gln Asn His Gly His Val Glu Asn Asp Glu
        135                 140                 145 tct tgg gtt ccg gtaatctttc ctactctcgt agtttctctt gtcttttatt           1789
Ser Trp Val Pro
    150 tatttgtttg ttttcggaa tttattctta tgtctatgtt cttaggattc tatatgttta    1849 ttttattagt ttatgttttc agtctgaggt cagaccgacc acttgtcaga tctgttttct    1909 agctgtagta aaaacaatt tgcaagtgta atagttcagc ataattgatc ttgttagagc     1969 atttccaaaa caaactttat aattttaaat atacagtttt ttgttctcta aaaaagaatt    2029 taaaattttt aaagtttgag ggacgaaact tcaaatttga actttcacta ctcaacttca    2089 aatttgaaat ttcatctttt ttatttacat tttgatcatt ataattaatt atacattaca    2149 tttatgattc ttaagtattt tctcatttat tgttttaatt cttaaatttt ttatacatca    2209 taaatatttc caatttgttt ttataaattc aaattttaca caaaaaagta ataaaaattt    2269 taaataagat ttataatatt ttaaaactat aattaggcaa aaaaaatatt acaaaaaaat    2329 gtaataaaaa cttaaaaata agatatatca agacataatt attagaaatt ttaaatatta    2389 taacaatatt aataatctgg taaatttgct ccaaaacctc aaaaatttct aaattattgt    2449 ccaaacaaat ttgtttaacc gaatatggag cattacaaaa ataatttttat ggaatagtgt    2509 ggtattttgc ttgtagttaa tatttaatta tgtatttcta tttataattt tatatatta     2569 atgtaagatt ttttaatta atattactgt aatattttta tatgtgtact agttatttat    2629 aaaagtttta tagatttgta ttagttataa caaaaataag gatcattgtg taaaatacaa    2689 ataattttga aattacgttt aaagttttgg ttatgaaaaa aatactttga aactttaaat    2749 ttagagtttt gcaaactttta aaatgttaga tagatagtt ttttggagat gcatttagtg    2809 gttatggtag taactcagaa aatgaaaaat ctatactttt atactccctc cgttttttaa    2869 tataagtcgt tttacagtta tacacgtaga ttaagaaaac cattaatttc ttatattttc    2929 tagacaaaaa catcattaat tatttaccta accacaattc aaccaatata aaatagaag     2989 atatattacc attggtcata caacattaat tattaataaa ttttacatag aaaaccgaaa    3049 acgacatata atttggaaca aaaaaatttc tctaaaacga cttatattaa aaaacggagg    3109 gagtagtacc taacttttaac gatggaccac ttatattcga gtccttagca taaatgatt    3169
```

```
ctcctcgaaa tccgtttact ttcttcatta ttttttcctt ttcagttttg gcgttttcgt       3229
aatacttttg tcttcaatct tgaaagctat tagtataaaa acttataaac acatcacatg       3289
caatgaatta atacgaatac ataaccagaa tgacaaattt tcaatgaata tttaatacca       3349
gtaagtacta ctccgtaata gtaatagtaa tagtcatatt aattttttt tgtcatcaaa        3409 caaacagtaa tagtaatatt aattataatt atgtatttca g ttg cca gaa aag ttg       3465
                                              Leu Pro Glu Lys Leu
                                                            155 tac aag aac ttg ccc cat agt act cgg atg ctc aga tac act gtt cct         3513
Tyr Lys Asn Leu Pro His Ser Thr Arg Met Leu Arg Tyr Thr Val Pro
        160                 165                 170 ctg ccc atg ctc gct tac ccg atc tat ctg gtaaaaaaaa atacaatttc           3563
Leu Pro Met Leu Ala Tyr Pro Ile Tyr Leu
175                 180 aatttttttc ttaaaattac aaatggtttt atattttgag ttttaagcca atatataaat       3623
taattttgat tggattttaa ctacag tgg tac aga agt cct gga aaa gaa ggg        3676
                       Trp Tyr Arg Ser Pro Gly Lys Glu Gly
                                   185                 190 tca cat ttt aac cca tac agt agt tta ttt gct cca agc gag agg aag         3724
Ser His Phe Asn Pro Tyr Ser Ser Leu Phe Ala Pro Ser Glu Arg Lys
            195                 200                 205 ctt att gca act tca aca act tgc tgg tcc ata atg ttg gcc act ctt         3772
Leu Ile Ala Thr Ser Thr Thr Cys Trp Ser Ile Met Leu Ala Thr Leu
210                 215                 220 gtt tat cta tcg ttc ctc gtt ggt cca gtc aca gtt ctc aaa gtc tat         3820
Val Tyr Leu Ser Phe Leu Val Gly Pro Val Thr Val Leu Lys Val Tyr
225                 230                 235                 240 ggt gtt cct tac att gtaagtttca catattatta caagagattt atatattatt        3875
Gly Val Pro Tyr Ile
            245 aataataaat ttgtttttg acataaagtt ttggaaaatt ttcag atc ttt gta atg        3932
                                                 Ile Phe Val Met tgg ttg gac gct gtc acg tac ttg cat cat cat ggt cac gat gag aag         3980
Trp Leu Asp Ala Val Thr Tyr Leu His His His Gly His Asp Glu Lys
250                 255                 260                 265 ttg cct tgg tac aga ggc aag gtaaataaat caattttaa aaagaaatgt             4031
Leu Pro Trp Tyr Arg Gly Lys
                270 acagaaagca ataatggtta gtattgatta atcttaattt ttgatgtttt gcatacaata      4091 atag gaa tgg agt tat tta cgt gga gga tta aca act att gat aga gat       4140
     Glu Trp Ser Tyr Leu Arg Gly Gly Leu Thr Thr Ile Asp Arg Asp
         275                 280                 285 tac gga atc ttc aac aac atc cat cac gac att gga act cac gtg atc        4188
Tyr Gly Ile Phe Asn Asn Ile His His Asp Ile Gly Thr His Val Ile
        290                 295                 300 cat cat ctt ttc cca caa atc cct cac tat cac ttg gtc gat gcg            4233
His His Leu Phe Pro Gln Ile Pro His Tyr His Leu Val Asp Ala
305                 310                 315 gtgagtgatc tagctttctc tctctctagt ttcatttgat taaatggtga ttaattacta      4293
atttaattaa tgaattgtgg acag acg aga gca gct aaa cat gtg tta gga         4344
                         Thr Arg Ala Ala Lys His Val Leu Gly
                                         320                 325 aga tac tac aga gag ccg aag acg tca gga gca ata ccg att cac ttg        4392
Arg Tyr Tyr Arg Glu Pro Lys Thr Ser Gly Ala Ile Pro Ile His Leu
        330                 335                 340 gtg gag agt ttg gtc gca agt att aaa aaa gat cat tac gtc agt gac        4440
Val Glu Ser Leu Val Ala Ser Ile Lys Lys Asp His Tyr Val Ser Asp
```

```
                    345                 350                 355
act ggt gat att gtc ttc tac gag aca gat cca gat ctc tac gtt tat      4488
Thr Gly Asp Ile Val Phe Tyr Glu Thr Asp Pro Asp Leu Tyr Val Tyr
360                 365                 370                 375 gct tcg gac aaa tct aaa atc aat                                      4512
Ala Ser Asp Lys Ser Lys Ile Asn
                380

<210> SEQ ID NO 6
<211> LENGTH: 383
<212> TYPE: PRT
<213> ORGANISM: Brassica napus

<400> SEQUENCE: 6

Met Val Val Ala Met Asp Gln Arg Ser Asn Val Asn Gly Asp Ser Gly
1               5                   10                  15

Ala Arg Lys Glu Glu Gly Phe Asp Pro Ser Glu Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Ala Arg Asp Ile Phe Ala Val Ala
    50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
    210                 215                 220

Val Tyr Leu Ser Phe Leu Val Gly Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
            260                 265                 270

Glu Trp Ser Tyr Leu Arg Gly Gly Leu Thr Thr Ile Asp Arg Asp Tyr
        275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
```

```
                            325                 330                 335
Gly Ala Ile Pro Ile His Leu Val Glu Ser Leu Val Ala Ser Ile Lys
                340                 345                 350

Lys Asp His Tyr Val Ser Asp Thr Gly Asp Ile Val Phe Tyr Glu Thr
            355                 360                 365

Asp Pro Asp Leu Tyr Val Tyr Ala Ser Asp Lys Ser Lys Ile Asn
        370                 375                 380

<210> SEQ ID NO 7
<211> LENGTH: 3729
<212> TYPE: DNA
<213> ORGANISM: Brassica napus
<220> FEATURE:
<221> NAME/KEY: CDS
<222> LOCATION: (1)..(299)
<220> FEATURE:
<221> NAME/KEY: CDS
<222> LOCATION: (782)..(871)
<220> FEATURE:
<221> NAME/KEY: CDS
<222> LOCATION: (1687)..(1753)
<220> FEATURE:
<221> NAME/KEY: CDS
<222> LOCATION: (2665)..(2757)
<220> FEATURE:
<221> NAME/KEY: CDS
<222> LOCATION: (2845)..(3030)
<220> FEATURE:
<221> NAME/KEY: CDS
<222> LOCATION: (3125)..(3205)
<220> FEATURE:
<221> NAME/KEY: CDS
<222> LOCATION: (3300)..(3437)
<220> FEATURE:
<221> NAME/KEY: CDS
<222> LOCATION: (3535)..(3729)

<400> SEQUENCE: 7 atg gtt gtt gct atg gac caa cgc acc aat gtg aac gga gat gcc ggt      48
Met Val Val Ala Met Asp Gln Arg Thr Asn Val Asn Gly Asp Ala Gly
1               5                   10                  15 gcc cgg aag gaa gaa ggg ttt gat ccg agc gca caa ccg ccg ttt aag      96
Ala Arg Lys Glu Glu Gly Phe Asp Pro Ser Ala Gln Pro Pro Phe Lys
            20                  25                  30 atc ggg gac ata agg gct gcg att cct aag cat tgt tgg gtg aaa agt     144
Ile Gly Asp Ile Arg Ala Ala Ile Pro Lys His Cys Trp Val Lys Ser
        35                  40                  45 cct ttg aga tct atg agc tac gta gcc aga gac att tgt gcc gtc gcg     192
Pro Leu Arg Ser Met Ser Tyr Val Ala Arg Asp Ile Cys Ala Val Ala
    50                  55                  60 gct ttg gcc att gcc gcc gtg tat ttt gat agc tgg ttc ctc tgt cct     240
Ala Leu Ala Ile Ala Ala Val Tyr Phe Asp Ser Trp Phe Leu Cys Pro
65                  70                  75                  80 ctc tat tgg gtc gcc caa gga acc ctt ttc tgg gcc atc ttc gtc ctc     288
Leu Tyr Trp Val Ala Gln Gly Thr Leu Phe Trp Ala Ile Phe Val Leu
                85                  90                  95 ggc cac gac tg gtaaagtttc ttccattttg cattgcatcg atttattgaa          339
Gly His Asp Cys tgcacgttct acgagtattg tttgtcagtt acttcgtaaa atgattcttt tgatgttcat    399
tttttgaaga tctaagattt ttttttaga ttttcttttt aaatcattgt tccaccacca    459
cctttcatcg gtcgtacgac tcgttacaac accacatctt tattttctat aattactact   519
gcttccgcat tttatggatc tctcaactta taattaaagt ataatatcaa gaatatctat   579
tattttcttt aaacaagaaa gataatattg tttctttgtt attttggtgt atttccaatc   639
```

```
tatttcgaga tttagaaatg tgacacgtca ttaccttgtt gaagtgttta aaacaaacat      699
ggaaagttta aataaatagt gcaataaatg atatatatgt atatgatgaa taatgatgtg      759
aaatataatt gaataatggc ag t gga cat ggg agt ttc tca gac att cct        809
                         Gly His Gly Ser Phe Ser Asp Ile Pro
                                            105 ctg ctg aat agt gtg gtt ggc cat att ctt cat tcc ttc atc ctc gtt       857
Leu Leu Asn Ser Val Val Gly His Ile Leu His Ser Phe Ile Leu Val
110             115                 120                 125 cct tac cat ggt tg  gtaagtcagc ttatcaaccc tttttactat attattaatt       911
Pro Tyr His Gly Trp attaaacttg catttgtata cttggtgcaa gttggtaaat gtaatctgat aactgaaaat      971
ctattcattg ctcgttctat ttttttttgg ctagagacaa ttttataatt aaataatgca     1031
tgtgagaata tgactattta tgtgaggtag cttttcttat tcctgtcgaa aagcatcaaa     1091
tctttagcaa cgaaggaaaa aggaatcaaa tttttatta aatgcaatgg gtctatgtct      1151
tggtcattag ttttttgcat ataatttatt tatatttttt tcttaacagc agctaattta     1211
attataatta aatattcatt ttataaataa tattagacca attattaaag gttagatatt     1271
ttaagaatta ttcatgactt tgtttattgg aactccttt atcttttaat cttttctatt      1331
tctccatttt taataatgag aaactgactt caaatctcca ataaagatgg tcttatgtag     1391
taacagtata attttttgtt tggtaaatgt aacatcatct tcaaatatct ttgaaaatag     1451
acttacatgc attattttgc tgcgacatta ttgtcactta ttcctggcaa taaattagtt     1511
tattactgaa cttttttgg tcaatttatt actagtaact ttaaacttaa aagagtgaga      1571
ttgtttgatc aaaaaaaata aaaatagagt gagatagtta gaatctgcca tgaaagcaac     1631
actatataga caatttaatt tttatgaaaa cacatttaat aatttgaggc tgcag g        1687 aga ata agc cat cgg aca cac cac cag aac cat ggc cat gtt gaa aac      1735
Arg Ile Ser His Arg Thr His His Gln Asn His Gly His Val Glu Asn
                135                 140                 145 gac gag tct tgg gtt ccg gtaacatttc cctctttaat aatttctatt              1783
Asp Glu Ser Trp Val Pro
            150 tttctgtcaa aataattagt ttttcgaaat ttgaggccag aacgaccact tgtcaaattt     1843 gatttttagc tgtagtaaaa acagtttgct agtgtcacag ttaaccggta attgattctt     1903 tttaacgatt tatagaagta acattttgt aaaataaaat atacattatg gtatgtgaca      1963 acggaccacg cttatttgta ttggtgaatc ttttaattac tccctccaat ttattttagt     2023 tgcagattta gatttatgca catagattaa taaaaatatt ttgcacattt tcaaaataaa     2083 aacaccatta cttatacaac taaccatatt tcaaccaata aaaataaatt agaaaatatt     2143 atttataaat tttgtattga aattataaaa taatacttat tttaaaacga aattaattta     2203 caacgacaat taaactgaaa cggaaagaaa ttattaatac ttaattaaag agttttaga      2263 aaaattgaaa gacatgttta tgcgaaactc atgtgaaagt ctttgaaata atagattttg     2323 gtataaatat ttcaattttt cttaaaataa aattatata ttaatataat ttgtgataaa      2383 atctcgtcaa aaactcacta atgcaaatgc ttttattttg aatttcttac tcctctaaat     2443 gcatttactt ttatactaat attattttct ttctctaatt tggcgtttcg taatagtttg     2503 tctgtatttt gaaaactaac aaaaaataat aaaaacaaaa gcttataaac acatagcatg     2563 caatgaatat gtacgaatat atataccaat acatatctaa gtactatttt tccaagtact     2623 taatcttgat tactaaaatt catttttaatt gttcctttca g tta cca gaa agg tta   2679
```

```
                    Leu Pro Glu Arg Leu
                                155 tac aag aat tta ccc cac agt act cgg atg ctc aga tac act gtc cct    2727
Tyr Lys Asn Leu Pro His Ser Thr Arg Met Leu Arg Tyr Thr Val Pro
        160                 165                 170 ctg ccc atg ctc gct tac ccg atc tat ctg gtatttttta attcctaaaa      2777
Leu Pro Met Leu Ala Tyr Pro Ile Tyr Leu
    175                 180 tttactacaa gtcatttag actgtgtttt aaaacaatat aattattttt gtttggtttt   2837 actgcag tgg tac aga agt cct gga aaa gaa ggg tca cat ttt aac cca    2886
        Trp Tyr Arg Ser Pro Gly Lys Glu Gly Ser His Phe Asn Pro
                185                 190                 195 tac agt ggt tta ttt gct cca agc gag aga aag ctt att gca act tcg    2934
Tyr Ser Gly Leu Phe Ala Pro Ser Glu Arg Lys Leu Ile Ala Thr Ser
            200                 205                 210 act act tgc tgg tcc ata atg ttg gca att ctt atc tgt ctt tcc ttc    2982
Thr Thr Cys Trp Ser Ile Met Leu Ala Ile Leu Ile Cys Leu Ser Phe
        215                 220                 225 ctc gtt ggt cca gtc aca gtt ctc aaa gta tac ggt gtt cct tac att    3030
Leu Val Gly Pro Val Thr Val Leu Lys Val Tyr Gly Val Pro Tyr Ile
230                 235                 240                 245 gtaagtttct tagtatatca taaagggtat atatttatta ttcaatatat atactatatg  3090
atttgttttt gtcatatatt tttgaaatat tcag atc ttt gtg atg tgg ttg gac 3145
                                    Ile Phe Val Met Trp Leu Asp
                                                        250 gct gtc act tac ttg cat cac cat ggt cat gat gag aag ttg cct tgg    3193
Ala Val Thr Tyr Leu His His His Gly His Asp Glu Lys Leu Pro Trp
            255                 260                 265 tac aga ggc aag gtaattaaat taactattac aagtatttta caaaaaacta        3245
Tyr Arg Gly Lys
    270 atgattagta tatttgatta atcttaattc ttgatgtttt gtgattaata atag gaa    3302
                                                            Glu tgg agt tac tta cgt gga gga tta aca act att gat aga gat tac gga   3350
Trp Ser Tyr Leu Arg Gly Gly Leu Thr Thr Ile Asp Arg Asp Tyr Gly
    275                 280                 285 att ttc aac aac att cat cac gac att gga act cac gtg atc cat cat   3398
Ile Phe Asn Asn Ile His His Asp Ile Gly Thr His Val Ile His His
290                 295                 300                 305 ctt ttc cca caa atc cct cac tat cac ttg gtc gat gct gtgagtcatc    3447
Leu Phe Pro Gln Ile Pro His Tyr His Leu Val Asp Ala
            310                 315 tcactctctg gctactttca tcaaaaccat ttgattaaag ggtgattaat tactaatgta  3507
gtgattttaa caaatggaat gtgacag aca aaa gca gct aaa cat gtg ttg gga 3561
                           Thr Lys Ala Ala Lys His Val Leu Gly
                                320                 325 aga tac tac aga gaa cca aag acg tca gga gca ata ccg atc cac ttg   3609
Arg Tyr Tyr Arg Glu Pro Lys Thr Ser Gly Ala Ile Pro Ile His Leu
        330                 335                 340 gtg gag agt ttg gta gca agt att aag aaa gat cat tac gtc agt gac   3657
Val Glu Ser Leu Val Ala Ser Ile Lys Lys Asp His Tyr Val Ser Asp
            345                 350                 355 act ggt gac att gtc ttc tac gag act gat cca gat ctc tac gtt tat   3705
Thr Gly Asp Ile Val Phe Tyr Glu Thr Asp Pro Asp Leu Tyr Val Tyr
360                 365                 370                 375 gct tct gtc aaa tcg aaa atc aat                                   3729
Ala Ser Val Lys Ser Lys Ile Asn
                380
```

<210> SEQ ID NO 8
<211> LENGTH: 383
<212> TYPE: PRT
<213> ORGANISM: Brassica napus

<400> SEQUENCE: 8

Met Val Val Ala Met Asp Gln Arg Thr Asn Val Asn Gly Asp Ala Gly
1               5                   10                  15

Ala Arg Lys Glu Glu Gly Phe Asp Pro Ser Ala Gln Pro Pro Phe Lys
                20                  25                  30

Ile Gly Asp Ile Arg Ala Ala Ile Pro Lys His Cys Trp Val Lys Ser
            35                  40                  45

Pro Leu Arg Ser Met Ser Tyr Val Ala Arg Asp Ile Cys Ala Val Ala
        50                  55                  60

Ala Leu Ala Ile Ala Ala Val Tyr Phe Asp Ser Trp Phe Leu Cys Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
                100                 105                 110

Ser Val Val Gly His Ile Leu His Ser Phe Ile Leu Val Pro Tyr His
            115                 120                 125

Gly Trp Arg Ile Ser His Arg Thr His His Gln Asn His Gly His Val
        130                 135                 140

Glu Asn Asp Glu Ser Trp Val Pro Leu Pro Glu Arg Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
                180                 185                 190

Ser His Phe Asn Pro Tyr Ser Gly Leu Phe Ala Pro Ser Glu Arg Lys
            195                 200                 205

Leu Ile Ala Thr Ser Thr Thr Cys Trp Ser Ile Met Leu Ala Ile Leu
        210                 215                 220

Ile Cys Leu Ser Phe Leu Val Gly Pro Val Thr Val Leu Lys Val Tyr
225                 230                 235                 240

Gly Val Pro Tyr Ile Ile Phe Val Met Trp Leu Asp Ala Val Thr Tyr
                245                 250                 255

Leu His His His Gly His Asp Glu Lys Leu Pro Trp Tyr Arg Gly Lys
                260                 265                 270

Glu Trp Ser Tyr Leu Arg Gly Gly Leu Thr Thr Ile Asp Arg Asp Tyr
            275                 280                 285

Gly Ile Phe Asn Asn Ile His His Asp Ile Gly Thr His Val Ile His
        290                 295                 300

His Leu Phe Pro Gln Ile Pro His Tyr His Leu Val Asp Ala Thr Lys
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
                340                 345                 350

Lys Asp His Tyr Val Ser Asp Thr Gly Asp Ile Val Phe Tyr Glu Thr
            355                 360                 365

Asp Pro Asp Leu Tyr Val Tyr Ala Ser Val Lys Ser Lys Ile Asn

-continued

```
<210> SEQ ID NO 9
<211> LENGTH: 4770
<212> TYPE: DNA
<213> ORGANISM: Brassica napus
<220> FEATURE:
<221> NAME/KEY: CDS
<222> LOCATION: (1)..(299)
<220> FEATURE:
<221> NAME/KEY: CDS
<222> LOCATION: (913)..(1002)
<220> FEATURE:
<221> NAME/KEY: CDS
<222> LOCATION: (1665)..(1731)
<220> FEATURE:
<221> NAME/KEY: CDS
<222> LOCATION: (3709)..(3801)
<220> FEATURE:
<221> NAME/KEY: CDS
<222> LOCATION: (3908)..(4093)
<220> FEATURE:
<221> NAME/KEY: CDS
<222> LOCATION: (4179)..(4259)
<220> FEATURE:
<221> NAME/KEY: CDS
<222> LOCATION: (4354)..(4491)
<220> FEATURE:
<221> NAME/KEY: CDS
<222> LOCATION: (4576)..(4770)

<400> SEQUENCE: 9
```

| | | | | | | | | | | | | | | | | |
|---|---|---|---|---|---|---|---|---|---|---|---|---|---|---|---|---|
| atg | gtt | gtt | gct | atg | tac | cag | cgc | agc | aat | gtt | aac | gga | gat | tcc | ggt | 48 |
| Met | Val | Val | Ala | Met | Tyr | Gln | Arg | Ser | Asn | Val | Asn | Gly | Asp | Ser | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | cgg | aag | gaa | gaa | ggg | ttt | gat | cca | agc | gca | caa | cca | ccg | ttt | aag | 96 |
| Ala | Arg | Lys | Glu | Glu | Gly | Phe | Asp | Pro | Ser | Ala | Gln | Pro | Pro | Phe | Lys | |
| | | 20 | | | | | 25 | | | | | 30 | | | | |

| | | | | | | | | | | | | | | | | |
|---|---|---|---|---|---|---|---|---|---|---|---|---|---|---|---|---|
| atc | gga | gat | ata | agg | gcg | gcg | att | cct | aag | cat | tgc | tgg | gtg | aag | agt | 144 |
| Ile | Gly | Asp | Ile | Arg | Ala | Ala | Ile | Pro | Lys | His | Cys | Trp | Val | Lys | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cct | ttg | aga | tct | atg | agc | tac | gtc | gcc | aga | gac | att | ttc | gcc | gtc | gcg | 192 |
| Pro | Leu | Arg | Ser | Met | Ser | Tyr | Val | Ala | Arg | Asp | Ile | Phe | Ala | Val | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| gct | ctg | gcc | atg | gcc | gcc | gtg | tat | ttt | gat | agc | tgg | ttc | ctc | tgg | cca | 240 |
| Ala | Leu | Ala | Met | Ala | Ala | Val | Tyr | Phe | Asp | Ser | Trp | Phe | Leu | Trp | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctc | tac | tgg | gtt | gcc | caa | gga | acc | ctt | ttc | tgg | gcc | atc | ttc | gtt | ctt | 288 |
| Leu | Tyr | Trp | Val | Ala | Gln | Gly | Thr | Leu | Phe | Trp | Ala | Ile | Phe | Val | Leu | |
| | | | | 85 | | | | | 90 | | | | | 95 | | |

| | | | | | | |
|---|---|---|---|---|---|---|
| ggc | cac | gac | tg | gtaaattaaa | ttttcagttt taattatttt gtctctttt | 339 |
| Gly | His | Asp | Cys | | | |

| | |
|---|---|
| gttcaattta ttaatttctt gaatgcacgt tcgatgagta tcgtcactga cttcaagatt | 399 |
| taattctttt gaggttactt tttcatgttt aattattaaa aaataaaag aaaatatagg | 459 |
| atctaagatt ttttttcttc atcaatgttc aagcatcatc actcatcagt cgtaagactc | 519 |
| gtaacaaaat atcttctttt ctataattaa tattatttcc gcattttatg gatctacgtt | 579 |
| ttgatgttct caattttgt ttctctttct ctagatcccc ggaactttta attataatta | 639 |
| tagtatagta taatatcaag aaaatatact gtttattttt ttggcaacaa atatattgtt | 699 |
| ttttgacaag aaaaatatat atatttttc ttctttttgt gttccaatct attttgtgat | 759 |
| ttagacaagt gacacgtcat ataccggatt tgttaccttg ttaaagagct tgagttaaaa | 819 |
| caaatgtaga aaagttaaaa taattgtgc aataaatgat aaatacgttt ttatgttaaa | 879 |

| | |
|---|---|
| taatgatgtg aaaataaaat tgaataatgg cag t gga cat ggg agt ttc tca<br>                                              Gly His Gly Ser Phe Ser<br>                                                        105 | 931 |
| gac att cct ctg ctg aac agt gtg gtt ggt cac att ctt cat tca ttc<br>Asp Ile Pro Leu Leu Asn Ser Val Val Gly His Ile Leu His Ser Phe<br>         110                 115                 120 | 979 |
| atc ctc gtt cct tac cat ggt tg  gtaagtcatt tattaactat ttccatgtaa<br>Ile Leu Val Pro Tyr His Gly Trp<br>       125 | 1032 |
| attattagta cttgttttcg tatttcttac attttcgttt gttattcttg ggtgcaatgc | 1092 |
| taggaaactg taatcagtat taactggaaa ctaccgactg ttttttttgtt gctagagtag | 1152 |
| caattttata attaaataag aatcctatta aacaatgcat gtgactatat gaggttgctt | 1212 |
| tttctgttca aaagcatcaa atctttagca gccaatgaaa aagaatccaa acctttctt | 1272 |
| aaatgatatg cgcctatcta tggtcctgag ttttcttagt ttcttaagta tatttagatt | 1332 |
| ttgatttttt tttaggtttt cacttattgt tatttgttta catcagcttc aaatatcttc | 1392 |
| gaaaagact tacatgcatc aatttcctga ggatttatag ttttttttac ttatttctga | 1452 |
| cacaatgttt attagtaaaa agcatcaaat gttttttttgc tcaaaaaaaa gaatgggatt | 1512 |
| gttagagcac tctattgtta gttgttcaat aaatatatca actaaaaaaa caaaataaat | 1572 |
| ataaaatgag tgagattgtt aaatcattat agagacaatt tcattttcac aaaaataaat | 1632 |
| aaatacataa cttttgtaat tggggtttgc ag g aga ata agc cat cgg aca cac<br>                                              Arg Ile Ser His Arg Thr His<br>                                                        135 | 1686 |
| cac cag aac cat ggc cat gtt gaa aac gac gag tct tgg gtt ccg<br>His Gln Asn His Gly His Val Glu Asn Asp Glu Ser Trp Val Pro<br>         140                 145                 150 | 1731 |
| gtaatctttc ctactctcat agtttctctt gtcttttatt gatttgttct ttttggggaa | 1791 |
| ttcattctta tgtctaagtt cttatgatta ttggggttct aaggtagaaa ttctatctta | 1851 |
| gaatataaaa acatgtctct taatttttaa ctaaaaagtt aagaaccagc ttttaaataa | 1911 |
| gaattttaaa aactggtttt ttaaattttt tagttaaaag ttaaaaaacg aattattata | 1971 |
| tttctctaaa aacctcgtca taagaaccct cattgatcat gctatgttta ttttattagt | 2031 |
| ttatgttttc agtctgaggt cagaccggcc acttgtcaga tctgttttct agctgtagta | 2091 |
| aaaaacaatt tgccagtgta atagttcagc ggtaattaat gttctggaat ctatctcaaa | 2151 |
| tttttttttt ataacttcag atataaagtt ttttgttctt aaaaaataaa tttcaaaatt | 2211 |
| tcaaatttga agttttttttt atttgcattt tgatcgttat aattaattac acgttacatt | 2271 |
| tataattctg aagtatttttt tcatttatcg ttttaattct taaattttttt atatattata | 2331 |
| aatatttcca gtttgttttt ataaattcaa attttacaca taaagtaat aaaaaaactt | 2391 |
| taaaataaga tacatgaaga cataactatt agaaaatttt aaatattata actatactaa | 2451 |
| taatctggta aatttgctct ggaacctcca aaattattgt ctaaacaaat tttatataac | 2511 |
| cgaagatgga acattacgaa aataattta tgaataata tgttattttg cttctaattt | 2571 |
| aatatttaat tatatatttc tatttataat tttatatatt taatgtaatt ttttattaat | 2631 |
| taatattact gtaatatttt tatatatgtg ctagttattt ataatttttt ttatggattt | 2691 |
| atatttgtta taacaaataa agatcattgt gtaaaataca aataatttttg aaattacgtt | 2751 |
| tgaagtttgt ttttgaagaa aaccactttg aaacttttaaa tttagagttt cgtgaactct | 2811 |
| aaaatagaga gttttttttta gaggttacgc agtaactcag aaaatgaaaa atctatactt | 2871 |
| ttatagtacc gaactttaac gatggaccac ttagagcatc attaacgggg gttcttagga | 2931 |

```
cggggttctt agcggaatat aagaacctga ctcttaattt ttaactgaaa atgctaagag   2991
tcggctctta actttaatga tgctaagagt cggctcttaa ctttaaggac ggggttctta   3051
agagccgact cttaactttt tcagttaaaa taacttttc agttaaaagt taagagtcgg   3111
gttcttatat tctgttaaga accatgtact aagaaccctg tgttaatgat ggtgttatat   3171
tcgagtcctt agcgtaaaat gattctcctc gaaatccgtt tactttcttc gttattttt   3231 cctttcagt tttggcgttt tcgtaatact tttctctgca atcttgaaag ctattagtat   3291
aaaacttata aacacatgaa ttaatacgaa tacataacca gaatgacaaa ttttcaatga   3351
atatttaata ctagtaagta ctactccgta atactccctc tgttttttaa agatgaatgt   3411
tctagagaaa tattttgttt ccaaatgatg tattttcat gttttcaaag tatatttgt   3471 caactaataa tgaaaaattg tgtatttcaa aaatattaat tacatttctt ttaatccaat   3531
tggtttaaaa atataaaaaa tataaagtta caaaaaacta tgcattaata actaaatttt   3591
aatatgattt cttaataaat gtgaaaatcc tagaacattc atctttaaaa aacagaggga   3651
gtagtaatta gtaatagtaa tagtaatagt catattaatt ataattatgt atttcag     3708 ttg cca gaa aag ttg tac aag aac ttg ccc cat agt act cgg atg ctc    3756
Leu Pro Glu Lys Leu Tyr Lys Asn Leu Pro His Ser Thr Arg Met Leu
    155                 160                 165 aga tac act gtc cct ctg ccc atg ctc gct tac ccg atc tat ctg        3801
Arg Tyr Thr Val Pro Leu Pro Met Leu Ala Tyr Pro Ile Tyr Leu
    170                 175                 180 gtaaaaaaaa aatacaattt ctattttttc ttaaaattac aaatgatttt atattttgag   3861
ttttaagcca atatataaat taattttgat tggaccttaa ctacag tgg tac aga     3916
                                                  Trp Tyr Arg
                                                          185 agt cct gga aaa gaa ggg tca cat ttt aac cca tac agt agt tta ttt    3964
Ser Pro Gly Lys Glu Gly Ser His Phe Asn Pro Tyr Ser Ser Leu Phe
    190                 195                 200 gct cca agc gag agg aag ctt att gca act tca act act tgc tgg tcc    4012
Ala Pro Ser Glu Arg Lys Leu Ile Ala Thr Ser Thr Thr Cys Trp Ser
    205                 210                 215 ata atg ttg gcc act ctt gtt tat cta tcg ttc ctc gtt gat cca gtc    4060
Ile Met Leu Ala Thr Leu Val Tyr Leu Ser Phe Leu Val Asp Pro Val
    220                 225                 230 aca gtt ctc aaa gtc tat ggc gtt cct tac att gtaagtttca catattatta  4113
Thr Val Leu Lys Val Tyr Gly Val Pro Tyr Ile
235                 240                 245 caagaaattt atatattatt aataataaat ttgttttttg acataaagtt ttggaaaatt   4173 ttcag atc ttt gtg atg tgg ttg gac gct gtc acg tac ttg cat cat cat  4223
      Ile Phe Val Met Trp Leu Asp Ala Val Thr Tyr Leu His His His
                          250                 255                 260 ggt cac gat gag aag ttg cct tgg tac aga ggc aag gtaattaaat         4269
Gly His Asp Glu Lys Leu Pro Trp Tyr Arg Gly Lys
                265                 270 caatttttaa aaagaaatgt acagaaagca ataatggtta gtattgatta atcttaattt   4329
ttgatgtttt gcatacaata atag gaa tgg agt tat tta cgt gga gga tta    4380
                              Glu Trp Ser Tyr Leu Arg Gly Gly Leu
                                              275                 280 aca act att gat aga gat tac gga atc ttc aac aac atc cat cac gac    4428
Thr Thr Ile Asp Arg Asp Tyr Gly Ile Phe Asn Asn Ile His His Asp
                285                 290                 295 att gga act cac gtg atc cat cat ctt ttc cca caa atc cct cac tat    4476
Ile Gly Thr His Val Ile His His Leu Phe Pro Gln Ile Pro His Tyr
```

```
                 300                 305                 310
cac ttg gtc gat gcc gtgagtgatc tagcttcctc tctctctagt ttcatttgat        4531
His Leu Val Asp Ala
            315 taaatggtga ttaattacta atttaattaa tgaattgtgg acag acg aga gca gct       4587
                                              Thr Arg Ala Ala
                                                      320 aaa cat gtg tta gga aga tac tac aga gag ccg aag acg tca gga gca        4635
Lys His Val Leu Gly Arg Tyr Tyr Arg Glu Pro Lys Thr Ser Gly Ala
            325                 330                 335 ata ccg att cac ttg gtg gag agt ttg gtc gca agt att aaa aaa gat        4683
Ile Pro Ile His Leu Val Glu Ser Leu Val Ala Ser Ile Lys Lys Asp
        340                 345                 350 cat tac gtc agt gac act ggt gat att gtc ttc tac gag aca gat cca        4731
His Tyr Val Ser Asp Thr Gly Asp Ile Val Phe Tyr Glu Thr Asp Pro
355                 360                 365                 370 gat ctc tac gtt tat gct tct gac aaa tct aaa atc aat                    4770
Asp Leu Tyr Val Tyr Ala Ser Asp Lys Ser Lys Ile Asn
                    375                 380

<210> SEQ ID NO 10
<211> LENGTH: 383
<212> TYPE: PRT
<213> ORGANISM: Brassica napus

<400> SEQUENCE: 10

Met Val Val Ala Met Tyr Gln Arg Ser Asn Val Asn Gly Asp Ser Gly
1               5                   10                  15

Ala Arg Lys Glu Glu Gly Phe Asp Pro Ser Ala Gln Pro Pro Phe Lys
            20                  25                  30

Ile Gly Asp Ile Arg Ala Ala Ile Pro Lys His Cys Trp Val Lys Ser
        35                  40                  45

Pro Leu Arg Ser Met Ser Tyr Val Ala Arg Asp Ile Phe Ala Val Ala
    50                  55                  60

Ala Leu Ala Met Ala Ala Val Tyr Phe Asp Ser Trp Phe Leu Trp Pro
65                  70                  75                  80

Leu Tyr Trp Val Ala Gln Gly Thr Leu Phe Trp Ala Ile Phe Val Leu
                85                  90                  95

Gly His Asp Cys Gly His Gly Ser Phe Ser Asp Ile Pro Leu Leu Asn
            100                 105                 110

Ser Val Val Gly His Ile Leu His Ser Phe Ile Leu Val Pro Tyr His
        115                 120                 125

Gly Trp Arg Ile Ser His Arg Thr His His Gln Asn His Gly His Val
    130                 135                 140

Glu Asn Asp Glu Ser Trp Val Pro Leu Pro Glu Lys Leu Tyr Lys Asn
145                 150                 155                 160

Leu Pro His Ser Thr Arg Met Leu Arg Tyr Thr Val Pro Leu Pro Met
                165                 170                 175

Leu Ala Tyr Pro Ile Tyr Leu Trp Tyr Arg Ser Pro Gly Lys Glu Gly
            180                 185                 190

Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
    210                 215                 220

Val Tyr Leu Ser Phe Leu Val Asp Pro Val Thr Val Leu Lys Val Tyr
225                 230                 235                 240
```

Gly Val Pro Tyr Ile Ile Phe Val Met Trp Leu Asp Ala Val Thr Tyr
            245                 250                 255

Leu His His His Gly His Asp Glu Lys Leu Pro Trp Tyr Arg Gly Lys
        260                 265                 270

Glu Trp Ser Tyr Leu Arg Gly Leu Thr Thr Ile Asp Arg Asp Tyr
    275                 280                 285

Gly Ile Phe Asn Asn Ile His His Asp Ile Gly Thr His Val Ile His
    290                 295                 300

His Leu Phe Pro Gln Ile Pro His Tyr His Leu Val Asp Ala Thr Arg
305                 310                 315                 320

Ala Ala Lys His Val Leu Gly Arg Tyr Tyr Arg Glu Pro Lys Thr Ser
                325                 330                 335

Gly Ala Ile Pro Ile His Leu Val Glu Ser Leu Val Ala Ser Ile Lys
            340                 345                 350

Lys Asp His Tyr Val Ser Asp Thr Gly Asp Ile Val Phe Tyr Glu Thr
        355                 360                 365

Asp Pro Asp Leu Tyr Val Tyr Ala Ser Asp Lys Ser Lys Ile Asn
    370                 375                 380

<210> SEQ ID NO 11
<211> LENGTH: 1131
<212> TYPE: DNA
<213> ORGANISM: Brassica napus

<400> SEQUENCE: 11
atggttgtcg ctatggacca gcgtagcaat gcgaacggag acgaaaggtt tgatccgagc        60
gcacaaccac cgttcaagat cggagatata agggcggcca ttcctaagca ttgttgggta       120
aagagtcctt tgagatccat gagctatgtc gccagagaca ttttcgccgt cgtggctctt       180
gccgtcgccg ccgtgtattt tgatagctgg ttcttttggc ctctttattg ggccgcccaa       240
ggaaccctgt tctgggctat cttcgtactc ggccacgact gtggacatgg gagcttctca       300
gacattcctc ttctgaatac tgcggttggt catattcttc attccttcat tctcgttcca       360
taccatggtt ggagaataag ccatcggaca caccaccaga accatggcca tgttgaaaac       420
gacgagtctt gggttccgtt gccagaaaaa ttatacaaga atttgtccca cagtacacgg       480
atgctcagat acactgtccc tctccccatg ctcgcttacc ctctctatct gtggtacaga       540
agtcctggta agaagggtc acattataac ccatacagta gtttatttgc tccaagcgag       600
agaaagctta ttgcaacttc aactacttgc tggtcgatca tgttggccac tcttgtttat       660
ctatcattcc tcgttggtcc agtcacagtt ctcaaagtct atggagttcc ttacattatc       720
tttgtaatgt ggttggacgc tgtcacgtac ttgcatcatc atggtcacga tgataagttg       780
ccttggtaca gaggcaagga atggagttat tacgtggag gattaacaac tattgataga       840
gattacggga tcttcaacaa cattcatcac gatattggaa ctcacgtgat ccatcatctt       900
ttcccacaaa tccctcacta tcacttggtc gatgccacga aagcagctaa acatgtgttg       960
ggaagatact acagagaacc aaagacgtca ggagcaatac cgatccactt ggtggaaagt      1020
ttggtggcaa gtattaagaa agatcattac gtcagtgaca ctggtgatat tgtcttctac      1080
gagacagatc cagatctcta cgtttatgct tctgacaaat ccaaaatcaa c               1131

<210> SEQ ID NO 12
<211> LENGTH: 1140
<212> TYPE: DNA
<213> ORGANISM: Brassica napus

<400> SEQUENCE: 12

```
atggttgtcg ctatggacca gcgtagcaat gtgaacggag attccaagga cgaaaggttt      60
gatccgagcg cacaaccacc gtttaagatc ggagatataa gggctgcgat tcctaagcat     120
tgttgggtca agagtccttt gagatccatg agctacgtcg cgagagacat tttctccgtc     180
gtggctctgg ccgtcgccgc cgtgtatttt gatagctggt tcttctggcc tctttattgg     240
gccgcccaag gaacccttt ctgggccatc ttcgtactcg gccacgactg tggacatggg      300
agcttctcag acattcctct tctgaatact gcggttggtc atattcttca ttccttcatt     360
ctcgttccat accatggttg gagaataagc catcggacac accaccagaa ccatggccat     420
gttgaaaacg acgagtcttg ggttccgttg ccagaaaaat tatacaagaa tttgtcccac     480
agtacacgga tgctcagata cactgtccct ctccccatgc tcgcttaccc tctctatctg     540
tggtacagaa gtcctggtaa agaagggtca cattataacc catacagtag tttatttgcc     600
ccaagcgaga gaaagcttat tgcaacttca actacttgct ggtcgatcgt gttggccact     660
cttgtttatc tatcattcct cgttggtcca gtcacagttc taaaagtcta tggtgttcct     720
tacattatct ttgtaatgtg gttggacgct gtcacgtact gcatcatca tggtcacgat      780
gataagctgc cttggtacag aggcaaggaa tggagttatt acgtggagg attaacaact      840
gttgatagag attacgggat cttcaacaac attcatcacg atattggaac tcacgtgatc     900
catcatcttt tcccacaaat ccctcactat cacttggtcg atgccacgaa agcagctaaa     960
catgtgttgg gaagatacta cagagaacca aagacgtcag gagcaatacc gatccactta    1020
gtggaaagtt tggtggcaag tattaagaaa gatcattacg tcagtgacac tggtgatatt    1080
gtcttctacg agacagatcc agatctctac gtttatgctt ctgacaaatc caaaatcaat    1140
```

<210> SEQ ID NO 13
<211> LENGTH: 1149
<212> TYPE: DNA
<213> ORGANISM: Brassica napus

<400> SEQUENCE: 13

```
atggttgttg ctatggacca gcgcagcaat gttaacggag attccggtgc ccggaaggaa      60
gaagggtttg atccaagcga acaaccaccg tttaagatcg gagatatcag gcggcgatt     120
cctaagcatt gttgggtgaa gagtcctttg agatctatga gctacgtcgc cagagacatt     180
ttcgccgtcg cggctctggc catggccgcc gtgtattttg atagctggtt cctctggcca     240
ctctactggg ttgcccaagg aaccctttc tgggccatct tcgttcttgg ccacgactgt      300
ggacatggga gttttcaga cattcctctg ctgaacagtg tggttggtca cattcttcat      360
tcattcatcc tcgttcctta ccatggttgg agaataagcc atcggacaca ccaccagaac     420
catggccatg ttgaaaacga cgagtcttgg gttccgttgc cagaaaagtt gtacaagaac     480
ttgccccata gtactcggat gctcagatac actgttcctc tgcccatgct cgcttacccg     540
atctatctgt ggtacagaag tcctggaaaa gaagggtcac attttaaccc atacagtagt     600
ttatttgctc caagcgagag gaagcttatt gcaacttcaa caacttgctg gtccataatg     660
ttggccactc ttgtttatct atcgttcctc gttggtccag tcacagttct caaagtctat     720
ggtgttcctt acattatctt tgtaatgtgg ttggacgctg tcacgtactt gcatcatcat     780
ggtcacgatg agaagttgcc ttggtacaga ggcaaggaat ggagttattt acgtggagga     840
ttaacaacta ttgatagaga ttacgggatc ttcaacaaca tccatcacga cattggaact     900
cacgtgatcc atcatctttt cccacaaatc cctcactatc acttggtcga tgcgacgaga     960
```

-continued

| | |
|---|---|
| gcagctaaac atgtgttagg aagatactac agagagccga agacgtcagg agcaataccg | 1020 |
| attcacttgg tggagagttt ggtcgcaagt attaaaaaag atcattacgt cagtgacact | 1080 |
| ggtgatattg tcttctacga gacagatcca gatctctacg tttatgcttc ggacaaatct | 1140 |
| aaaatcaat | 1149 |

<210> SEQ ID NO 14
<211> LENGTH: 1149
<212> TYPE: DNA
<213> ORGANISM: Brassica napus

<400> SEQUENCE: 14

| | |
|---|---|
| atggttgttg ctatggacca acgcaccaat gtgaacggag atgccggtgc ccggaaggaa | 60 |
| gaagggtttg atccgagcgc acaaccgccg tttaagatcg gggacataag ggctgcgatt | 120 |
| cctaagcatt gttgggtgaa aagtcctttg agatctatga gctacgtagc cagagacatt | 180 |
| tgtgccgtcg cggctttggc cattgccgcc gtgtattttg atagctggtt cctctgtcct | 240 |
| ctctattggg tcgcccaagg aacccttttc tgggccatct tcgtcctcgg ccacgactgt | 300 |
| ggacatggga gtttctcaga cattcctctg ctgaatagtg tggttggcca tattcttcat | 360 |
| tccttcatcc tcgttcctta ccatggttgg agaataagcc atcggacaca ccaccagaac | 420 |
| catggccatg ttgaaaacga cgagtcttgg gttccgttac agaaaggtt atacaagaat | 480 |
| ttaccccaca gtactcggat gctcagatac actgtccctc tgcccatgct cgcttacccg | 540 |
| atctatctgt ggtacagaag tcctggaaaa aagggtcac attttaaccc atacagtggt | 600 |
| ttatttgctc caagcgagag aaagcttatt gcaacttcga ctacttgctg gtccataatg | 660 |
| ttggcaattc ttatctgtct ttccttcctc gttggtccag tcacagttct caaagtatac | 720 |
| ggtgttcctt acattatctt tgtgatgtgg ttggacgctg tcacttactt gcatcaccat | 780 |
| ggtcatgatg agaagttgcc ttggtacaga ggcaaggaat ggagttactt acgtggagga | 840 |
| ttaacaacta ttgatagaga ttacggaatt ttcaacaaca ttcatcacga cattggaact | 900 |
| cacgtgatcc atcatctttt cccacaaatc cctcactatc acttggtcga tgctacaaaa | 960 |
| gcagctaaac atgtgttggg aagatactac agagaaccaa agacgtcagg agcaataccg | 1020 |
| atccacttgg tggagagttt ggtagcaagt attaagaaag atcattacgt cagtgacact | 1080 |
| ggtgacattg tcttctacga gactgatcca gatctctacg tttatgcttc tgtcaaatcg | 1140 |
| aaaatcaat | 1149 |

<210> SEQ ID NO 15
<211> LENGTH: 1149
<212> TYPE: DNA
<213> ORGANISM: Brassica napus

<400> SEQUENCE: 15

| | |
|---|---|
| atggttgttg ctatgtacca gcgcagcaat gttaacggag attccggtgc ccggaaggaa | 60 |
| gaagggtttg atccaagcgc acaaccaccg tttaagatcg gagatataag ggcggcgatt | 120 |
| cctaagcatt gctgggtgaa gagtcctttg agatctatga gctacgtcgc cagagacatt | 180 |
| ttcgccgtcg cggctctggc cattgccgcc gtgtattttg atagctggtt cctctggcca | 240 |
| ctctactggg ttgcccaagg aacccttttc tgggccatct tcgttcttgg ccacgactgt | 300 |
| ggacatggga gtttctcaga cattcctctg ctgaacagtg tggttggtca cattcttcat | 360 |
| tcattcatcc tcgttcctta ccatggttgg agaataagcc atcggacaca ccaccagaac | 420 |

```
catggccatg ttgaaaacga cgagtcttgg gttccgttgc cagaaaagtt gtacaagaac    480
ttgccccata gtactcggat gctcagatac actgtccctc tgcccatgct cgcttacccg    540
atctatctgt ggtacagaag tcctggaaaa gaagggtcac attttaaccc atacagtagt    600
ttatttgctc caagcgagag gaagcttatt gcaacttcaa ctacttgctg gtccataatg    660
ttggccactc ttgtttatct atcgttcctc gttgatccag tcacagttct caaagtctat    720
ggcgttcctt acattatctt tgtgatgtgg ttggacgctg tcacgtactt gcatcatcat    780
ggtcacgatg agaagttgcc ttggtacaga ggcaaggaat ggagttattt acgtggagga    840
ttaacaacta ttgatagaga ttacggaatc ttcaacaaca tccatcacga cattggaact    900
cacgtgatcc atcatctttt cccacaaatc cctcactatc acttggtcga tgccacgaga    960
gcagctaaac atgtgttagg aagatactac agagagccga agacgtcagg agcaataccg   1020
attcacttgg tggagagttt ggtcgcaagt attaaaaaag atcattacgt cagtgacact   1080
ggtgatattg tcttctacga gacagatcca gatctctacg tttatgcttc tgacaaatct   1140
aaaatcaat                                                           1149
```

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
tggagttatc tacgtggagg                                                20

<210> SEQ ID NO 17
<211> LENGTH: 20
<212> TYPE: DNA
<213> ORGANISM: Artificial
<220> FEATURE:
<223> OTHER INFORMATION: PCR primer

<400> SEQUENCE: 17
gcgtaaacgt agagatctgg                                                20

<210> SEQ ID NO 18
<211> LENGTH: 19
<212> TYPE: DNA
<213> ORGANISM: Artificial
<220> FEATURE:
<223> OTHER INFORMATION: probe

<400> SEQUENCE: 18
tctttgtaat gtgattgga                                                 19

<210> SEQ ID NO 19
<211> LENGTH: 19
<212> TYPE: DNA
<213> ORGANISM: Artificial
<220> FEATURE:
<223> OTHER INFORMATION: probe

<400> SEQUENCE: 19
ctttgtaatg tggttggac                                                 19

<210> SEQ ID NO 20
<211> LENGTH: 27
<212> TYPE: DNA
<213> ORGANISM: Artificial

-continued

```
<220> FEATURE:
<223> OTHER INFORMATION: primer

<400> SEQUENCE: 20
cagtcacagt tctcaaagtc tatggag                                        27

<210> SEQ ID NO 21
<211> LENGTH: 24
<212> TYPE: DNA
<213> ORGANISM: Artificial
<220> FEATURE:
<223> OTHER INFORMATION: primer

<400> SEQUENCE: 21
tgcctctgta ccaaggcaac ttat                                           24

<210> SEQ ID NO 22
<211> LENGTH: 19
<212> TYPE: DNA
<213> ORGANISM: Artificial
<220> FEATURE:
<223> OTHER INFORMATION: probe

<400> SEQUENCE: 22
ggatgactac agtgataca                                                 19

<210> SEQ ID NO 23
<211> LENGTH: 20
<212> TYPE: DNA
<213> ORGANISM: Artificial
<220> FEATURE:
<223> OTHER INFORMATION: probe

<400> SEQUENCE: 23
gatgactaca gtggtacaga                                                20

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
cctctctatc tggtaaatcc taattcctaa                                     30

<210> SEQ ID NO 25
<211> LENGTH: 29
<212> TYPE: DNA
<213> ORGANISM: Artificial
<220> FEATURE:
<223> OTHER INFORMATION: primer

<400> SEQUENCE: 25
gtatgggtta taatgtgacc cttctttac                                      29

<210> SEQ ID NO 26
<211> LENGTH: 20
<212> TYPE: DNA
<213> ORGANISM: Artificial
<220> FEATURE:
<223> OTHER INFORMATION: probe

<400> SEQUENCE: 26
atctttgtaa tgtagttgga                                                20
```

```
<210> SEQ ID NO 27
<211> LENGTH: 20
<212> TYPE: DNA
<213> ORGANISM: Artificial
<220> FEATURE:
<223> OTHER INFORMATION: probe

<400> SEQUENCE: 27
atctttgtaa tgtggttgga                                               20

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
ggtgttcctt acattgtaag tttcaca                                       27

<210> SEQ ID NO 29
<211> LENGTH: 23
<212> TYPE: DNA
<213> ORGANISM: Artificial
<220> FEATURE:
<223> OTHER INFORMATION: primer

<400> SEQUENCE: 29
gcctctgtac caaggcaact tct                                           23

<210> SEQ ID NO 30
<211> LENGTH: 19
<212> TYPE: DNA
<213> ORGANISM: Artificial
<220> FEATURE:
<223> OTHER INFORMATION: probe

<400> SEQUENCE: 30
ttactgcagt gatacagaa                                                19

<210> SEQ ID NO 31
<211> LENGTH: 18
<212> TYPE: DNA
<213> ORGANISM: Artificial
<220> FEATURE:
<223> OTHER INFORMATION: probe

<400> SEQUENCE: 31
ttactgcagt ggtacaga                                                 18

<210> SEQ ID NO 32
<211> LENGTH: 25
<212> TYPE: DNA
<213> ORGANISM: Artificial
<220> FEATURE:
<223> OTHER INFORMATION: primer

<400> SEQUENCE: 32
cgcttacccg atctatctgg tattt                                         25

<210> SEQ ID NO 33
<211> LENGTH: 25
<212> TYPE: DNA
<213> ORGANISM: Artificial
<220> FEATURE:
<223> OTHER INFORMATION: primer
```

```
<400> SEQUENCE: 33
gggttaaaat gtgacccttc ttttc                                              25

<210> SEQ ID NO 34
<211> LENGTH: 20
<212> TYPE: DNA
<213> ORGANISM: Artificial
<220> FEATURE:
<223> OTHER INFORMATION: probe

<400> SEQUENCE: 34
gaccttaact acagtagtac                                                    20

<210> SEQ ID NO 35
<211> LENGTH: 20
<212> TYPE: DNA
<213> ORGANISM: Artificial
<220> FEATURE:
<223> OTHER INFORMATION: probe

<400> SEQUENCE: 35
accttaacta cagtggtaca                                                    20

<210> SEQ ID NO 36
<211> LENGTH: 23
<212> TYPE: DNA
<213> ORGANISM: Artificial
<220> FEATURE:
<223> OTHER INFORMATION: primer

<400> SEQUENCE: 36
atgctcgctt acccgatcta ttt                                                23

<210> SEQ ID NO 37
<211> LENGTH: 24
<212> TYPE: DNA
<213> ORGANISM: Artificial
<220> FEATURE:
<223> OTHER INFORMATION: primer

<400> SEQUENCE: 37
ctctcgcttg gagcaaataa acta                                               24
```

BRASSICA PLANTS COMPRISING MUTANT FAD3 ALLELES

CROSS-REFERENCE TO RELATED APPLICATIONS

This application is a § 371 U.S. National Stage of International Application No. PCT/EP2010/007028, filed Oct. 19, 2010, which claims the benefit of European Patent Application Serial No. 09075513.3, filed Nov. 23, 2009, and U.S. Provisional Patent Application Ser. No. 61/263,042, filed Nov. 20, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS09-2011WO.ST25.txt", created on Nov. 18, 2010, and having a size of 78,300 bytes and is filed concurrently with the specification. The sequence listing contained in this ASCII formatted document is part of the specification and is herein incorporated by reference in its entirety.

FIELD OF THE INVENTION

This invention relates to crop plants and parts, particularly of the Brassicaceae family, in particular *Brassica* species, with improved fatty acid composition, more specifically, reduced alpha-linolenic acid content in seed. This invention also relates to a fatty acid desaturases and nucleic acids encoding desaturase proteins. More particularly, this invention relates to nucleic acids encoding delta-15 fatty acid desaturase proteins, and mutants thereof, that affect fatty acid composition in plant seed oil. Methods are also provided to identify molecular markers associated with reduced alpha-linolenic acid content in seed in a population of plants.

BACKGROUND OF THE INVENTION

Vegetable oils are increasingly important economically because they are widely used in human and animal diets and in many industrial applications. However, the fatty acid compositions of these oils are often not optimal for many of these uses. Because specialty oils with particular fatty acid composition are needed for both nutritional and industrial purposes, there is considerable interest in modifying oil composition by plant breeding and/or by new molecular tools of plant biotechnology.

The specific performance and health attributes of edible oils are determined largely by their fatty acid composition. Most vegetable oils derived from commercial plant varieties are composed primarily of palmitic (C16:0), stearic (C18:0), oleic (C18:1), linoleic (C18:2) and linolenic (C18:3) acids. Palmitic and stearic acids are, respectively, 16 and 18 carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids.

*Brassica* species like *Brassica napus* (*B. napus*) and *Brassica rapa* (*B. rapa*) constitute the third most important source of vegetable oil in the world. In Canada, plant scientists focused their efforts on creating so-called "double-low" varieties which were low in erucic acid in the seed oil and low in glucosinolates in the solid meal remaining after oil extraction (i.e., an erucic acid content of less than 2.0 percent by weight based upon the total fatty acid content (called herein after wt %), and a glucosinolate content of less than 30 micromoles per gram of the oil-free meal). These higher quality forms of rape developed in Canada are known as canola.

Oil extracted from natural and previously commercially useful varieties of canola contains a relatively high (8%-10%) alpha-linolenic acid content (C18:3) (US Patent Application 20080034457). Higher values of e.g. 11% have also been reported (http://www.canolacouncil.org/canola_oil_properties_and_uses.aspx). This trienoic fatty acid is unstable and easily oxidized during cooking, which in turn creates off-flavors of the oil (Gailliard, 1980, Vol. 4, pp. 85-116 In: Stumpf, P. K., ed., The Biochemistry of Plants, Academic Press, New York). It also develops off odors and rancid flavors during storage (Hawrysh, 1990, Stability of canola oil, Chapter 7, pp. 99-122 In: F. Shahidi, ed. Canola and Rapeseed: Production, Chemistry, Nutrition, and Processing Technology, Van Nostrand Reinhold, N.Y.). Both flavor and nutritional quality of the oil is improved by reducing the C18:3 levels in favor of C18:2 (Diepenbrock and Wilson, Crop Sci 27:75-77, 1987)

It is known that reducing the alpha-linolenic acid content level by hydrogenation increases the oxidative stability of the oil. Unfortunately, chemical hydrogenation leads to the formation of trans-fatty acids, which have been linked to elevated levels of low-density lipoprotein cholesterol (LDL or "bad" cholesterol) in the blood, and consequently, to an increased risk of coronary heart disease.

Another strategy to improve oil quality is by breeding for low linolenic varieties, which is particularly challenging since C18:3 content is a multi-gene trait and inherited in a recessive manner with a relatively low heritability (WO04072259). Burns et al. (Heredity 90:39-48, 2003) identified five qualitative trait loci (QTL) associated with C18:3 content in *B. napus*, of which three with positive effect located on N6, N7 and N18, and two with negative effect on N7 and N11. Genetic analysis of a population derived from the cross between "Stellar" (having a low C18:3 content (3%)) and 'Drakkar' (having a "conventional" C18:3 level (9-10%)) indicated that the low C18:3 trait was controlled by two major loci with additive effects designated L1 and L2 (Jourdren et al., Euphytica 90:351-357, 1996). These two major loci controlling C18:3 content were found to correspond to two FAD3 (fatty acid desaturase 3) genes; one located on A genome (originating from *Brassica rapa*) on N4 and the other on the C genome (originating from *Brassica oleracea*) on N14 (Jourdren et al., Theor. Appl. Genet. 93:512-518, 1996; Barret et al., GCIRC, 1999).

Canola varieties with mutations in the FAD3 gene have been described in the art. For example, WO06/034059 describes that two canola varieties with reduced linolenic acid content, IMC01 and IMC02 (originally disclosed in U.S. Pat. No. 5,750,827 and US patent application 20080034457, respectively) are thought to have mutations in FAD3 genes. WO04/072259 discloses a FAD3 allele (of the C genome) with a single nucleotide substitution in a 5' splice site from a mutant canola line DMS 100 with a linolenic acid content of about 3%. WO01/25453 describes new FAD3 variants with multiple amino acid substitutions, one of which is also present in "Stellar", from the low linolenic "Apollo" variety. In US patent application 20040083503 a non-functional FAD3 mutant is disclosed with an amino acid substitution in a conserved domain. However, the linolenic acid phenotype of canola plants comprising such mutant FAD3 alleles can be highly variable depending on the genetic background.

Therefore, despite the fact that sequences of various FAD3 alleles are available in the art, a need remains for alternative methods (especially non-transgenic methods) for stably reducing the amount of alpha-linolenic acid in seed, without having a negative effect on the plants growth and development. The inventions described hereinafter in the different embodiments, examples and claims provide methods and means for developing crop plants which produce seed oil that is low in C18:3 content.

SUMMARY OF THE INVENTION

The inventors have found that *Brassica napus* plants comprise five different FAD3 genes and that the levels of C18:3 in *Brassica* plants, particularly in the seed oil of said *Brassica* plants, can be controlled by controlling the number and/or types of FAD3 genes/alleles that are "functionally expressed" in seeds, i.e. that result in functional (biologically active) FAD3 protein. By combining certain mutant alleles of the five FAD3 genes ("fad3 alleles"), resulting in a reduction of the level of functional FAD3 protein, the level of C18:3 in the seed oil can be significantly reduced. It is thought that the more FAD3 mutant alleles are combined in a plant the greater the reduction in C18:3 seed oil content will be, while remaining a normal plant growth and seed development.

Thus, in a first aspect, the present invention provides in one embodiment a *Brassica* plant (and parts thereof, such as seeds) comprising at least two mutant FAD3 alleles in its genome, wherein
  i. the first mutant FAD3 allele is selected from the group consisting of FAD3-A1 or FAD3-C1; and
  ii. the second mutant FAD3 allele is selected from the group consisting of FAD3-A2, FAD3-A3 or FAD3-C2.
wherein the seed oil of said plant displays a significant reduction in the amount of total alpha-linolenic acid (C18:3) present in the seed oil of a plant said mutant FAD3 alleles when compared to the seed oil of similar plants not comprising said mutant FAD3 allele(s).

The invention also provides a plant further comprising a third full knock-out mutant FAD3 allele, wherein said third full knock-out mutant FAD3 allele is selected from the group consisting of FAD3-A1 or FAD3-C1, whereby the mutant FAD3 alleles are mutant alleles of at least three different FAD3 genes.

Also provided herein is a plant further comprising fourth full knock-out mutant FAD3 allele, wherein said fourth full knock-out mutant FAD3 allele is selected from the group consisting of FAD3-A2, FAD3-A3 or FAD3-C2, whereby the mutant FAD3 alleles are mutant alleles of at least four different FAD3 genes.

The invention furthermore provides a plant further comprising a fifth full knock-out mutant FAD3 allele, wherein said fifth full knock-out mutant FAD3 allele is selected from the group consisting of FAD3-A2, FAD3-A3 or FAD3-C2, whereby the mutant FAD3 alleles are mutant alleles of at least five different FAD3 genes.

In another aspect, the invention provides (isolated) nucleic acid sequences encoding wild type and/or mutant FAD3 proteins, as well as fragments thereof, and methods of using these nucleic acid sequences to modify the *Brassica* seed oil composition. Also provided herein are the wild type and/or mutant FAD3 proteins themselves and their use, as well as plants comprising these mutant FAD3 alleles and FAD3 proteins.

The invention further relates to a plant, and cells, parts, seeds and progeny thereof, comprising one or more knock-out mutant FAD3 alleles. In one aspect, the plant comprises a reduced amount of functional FAD3 proteins compared to a plant, and cells, parts, seeds and progeny thereof, comprising a FAD3 allele encoding the corresponding functional FAD3 protein. Such plants, and cells, parts, seeds and progeny thereof, can be used for obtaining plants producing seed or grain with altered seed oil composition, in particular for obtaining *Brassica* plants producing seed or grain with a significantly reduced C18:3 seed oil content that preferably maintain an agronomically suitable plant development. As used herein, "plant part" includes anything derived from a plant of the invention, including plant parts such as cells, tissues, organs, seeds, seed pods, seed meal, seed cake, seed fats or oils.

In a further aspect, the invention relates to seed or grain with a reduced C18:3 oil content, which can be obtained from a plant according to the present invention, and the use of said seed or grain, for example for planting and growing progeny from the plants or for producing seed meal, seed cake, seed fats or oils.

In yet another aspect of the invention, methods are provided for generating and selecting plants, and cells, parts, seeds and progeny thereof, containing one or more full knock-out FAD3 alleles. In particular, methods are provided for generating and selecting *Brassica* plants comprising at least two FAD3 genes, in particular *Brassica napus* plants, and cells, parts, seeds and progeny thereof, containing at least two full knock-out mutant FAD3 alleles at at least two different loci in the genome (i.e. at least two different FAD3 genes) and to distinguish between the presence of mutant FAD3 alleles and wild type FAD3 alleles in a plant or plant part. Thus methods are provided (such as mutagenesis and/or marker assisted selection) for generating and/or identifying mutant FAD3 alleles or plants or plant parts comprising such alleles and for combining a suitable number of mutant FAD3 alleles in a single plant, whereby the plant has a significantly reduced C18:3 seed oil content.

Methods are also provided for using the plant, and cells, parts, seeds and progeny thereof, of the invention, for obtaining "low linolenic acid" seed oil from crushed *Brassica* seeds. As used herein, "plant product" includes anything derived from a plant of the invention, including plant parts such as seeds, seed meal, seed cake, seed fats or oils.

GENERAL DEFINITIONS

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence which is within a plant cell, e.g. an endogenous allele of a FAD3 gene present within the nuclear genome of a *Brassica* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. a pre-mRNA, comprising intron sequences, which is then spliced into a mature mRNA) in a cell, operable linked to regulatory regions (e.g. a promoter).

A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a 'transgene'), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

The terms "protein" or "polypeptide" are used interchangeably and refer to molecules consisting of a chain of amino acids, without reference to a specific mode of action, size, 3-dimensional structure or origin. A "fragment" or "portion" of a FAD3 protein may thus still be referred to as a "protein". An "isolated protein" is used to refer to a protein which is no longer in its natural environment, for example in vitro or in a recombinant bacterial or plant host cell. An "enzyme" is a protein comprising enzymatic activity, such as functional FAD3 proteins, which are capable of desaturation linoleic acid to linolenic acid.

As used herein "FAD3 protein", also known as "fatty acid desaturase 3", "omega-3 fatty acid desaturase" or "delta-15 desaturase", refers to an ER resident protein that introduces the the third double bond in the biosynthesis of C18:3 fatty acids. Fatty acid desaturases are iron-containing enzymes that catalyze the NAD-(P)H- and O2-dependent introduction of double bonds into methylene-interrupted fatty acyl chains. Hydropathy analyses indicate that these enzymes contain up to three long hydrophobic domains which would be long enough to span the membrane bilayer twice. The enzymes contain three conserved His-containing regions (His-boxes), which have a consistent positioning with respect to these potential membrane spanning domains. All single histidine residues in these conserved regions, which are putatively involved in iron binding, appeared essential for protein function (Shanklin et al., Biochemistry 33:12787-94, 1994). In FAD3-A1 (SEQ ID NO: 2), eight conserved putative diiron-binding histidines are present on amino acid positions 92, 96, 128, 131, 132, 295, 298 and 299 (GenBank: ACS26169.1).

The term "signal sequence" or "signal peptide" refers to a short (3-60 amino acids long) peptide chain on the N-terminus of a protein which directs initial targeting of a protein to intracellular organelles such as the endoplasmatic reticulum (ER). ER resident proteins, such as FAD3, may comprise a cleavable N-terminal signal sequence for initial, co-translational targeting to the ER, but the first transmembrane domain may also act as a non-cleavable signal sequence directing co-translational protein synthesis and acting as a stop transfer sequence for anchoring the protein in the membrane. It was demonstrated that Brassica FAD3 is inserted into the ER membrane in a co-translational manner (McCartney et al., 2004, Plant Journal 37, pages 156-173).

"ER retention motif" as used herein, is a C terminal tetrapeptide motif H/K/RDEL which is responsible for static ER retention or retrieval from other compartments in the secretory pathway. Any non-conserved amino acid change to the motif is known to results in loss of ER retrieval. FAD3 comprises a conserved dilysine motif (amino acid positions -3 and -5 relative to the C-terminus) which functions as an ER retention signal. Truncation of the five C-terminal amino acids -KSKIN or a substitution of the two lysines to alanines resulted in mislocalization of FAD3 to the Golgi or to the plasma membrane respectively, as well as a severe impairment of FAD3 enzymatic activity (McCartney et al., 2004, Plant Journal 37, pages 156-173). Corresponding amino acid regions or residues in other FAD3 sequences can be found by methods known in the art, such as by determining the optimal alignment, as described below.

The term "FAD3 gene" refers herein to the nucleic acid sequence encoding a fatty acid desaturase (i.e. a FAD3 protein). A functional "FAD3 protein" has fatty acyl desaturase activity, more specifically, it is capable of desaturating linoleic acid (C18:2) into linolenic acid (C18:3). The functionality of FAD3 proteins can be tested using a biological assay. To determine the function and/or the functionality of a specific FAD3 gene/protein, a yeast expression system as described by Vrinten et al. (2005, Plant Physiol. 139:79-87) or by Reed et al. (2000, Plant Physiol. 122:715-20) or a bacterial expression system as described by e.g. Reddy et al. (Plant Mol Biol 22:293-300, 1993) can, for example be used. Alternatively, the gene encoding the FAD3 protein can e.g. be transformed into Brassica (or another plant) and the resulting transformants screened for overexpression phenotypes, as described in e.g. US Patent Application 20040083503.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found. For example, the "FAD3-A1" refers to the position on a chromosome where the FAD3-A1 gene (and two FAD3-A1 alleles) may be found, while the "FADS-C1 locus" refers to the position on a chromosome where the FADS-C1 gene (and two FADS-C1 alleles) may be found.

"Essentially similar", as used herein, refers to sequences having at least 75%, at least 80%, at least 85%, at least 90%, at least 95%, 98%, 99% or 100% sequence identity. These nucleic acid sequences may also be referred to as being "substantially identical" or "essentially identical" to the FADS sequences provided in the sequence listing. The "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 μg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

The term "ortholog" of a gene or protein refers herein to the homologous gene or protein found in another species, which has the same function as the gene or protein, but is (usually) diverged in sequence from the time point on when the species harboring the genes diverged (i.e. the genes evolved from a common ancestor by speciation). Orthologs of the *Brassica napus* FAD3 genes may thus be identified in other plant species (e.g. *Brassica juncea*, etc.) based on both sequence comparisons (e.g. based on percentages sequence identity over the entire sequence or over specific domains) and/or functional analysis.

The term "mutant" or "mutation" refers to e.g. a plant or gene that is different from the so-called "wild type" variant (also written "wildtype" or "wild-type"), which refers to a typical form of e.g. a plant or gene as it most commonly occurs in nature. A "wild type plant" refers to a plant with the most common phenotype of such plant in the natural population. A "wild type allele" refers to an allele of a gene required to produce the wild-type phenotype. A mutant plant or allele can occur in the natural population or be produced by human intervention, e.g. by mutagenesis, and a "mutant allele" thus refers to an allele of a gene required to produce the mutant phenotype. As used herein, the term "mutant FAD3 allele" (e.g. mutant FAD3-A1, FAD3-C1, FAD3-A2, FAD3-A3 or FAD3-C2) refers to a FAD3 allele, which directs expression of a significantly reduced amount of functional FAD3 protein than the corresponding wild type allele. This can occur either by the mutant FAD3 allele encoding a non-functional FAD3 protein which, as used herein, refers to a FAD3 protein having no biological activity a significantly modified and/or a significantly reduced biological activity as compared to the corresponding wild-type functional FAD3 protein, or by the mutant FAD3 allele encoding a significantly reduced amount of functional FAD3 protein or no FAD3 protein at all. Such a "mutant FAD3 allele" thus comprises one or more mutations in its nucleic acid sequence when compared to the wild type allele, whereby the mutation(s) preferably result in a significantly reduced (absolute or relative) amount of functional FAD3 protein in the cell in vivo.

Mutations in nucleic acid sequences may include for instance:
(a) a "missense mutation", which is a change in the nucleic acid sequence that results in the substitution of an amino acid for another amino acid;
(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
(c) an "insertion mutation" of one or more amino acids, due to one or more codons having been added in the coding sequence of the nucleic acid;
(d) a "deletion mutation" of one or more amino acids, due to one or more codons having been deleted in the coding sequence of the nucleic acid;
(e) a "frameshift mutation", resulting in the nucleic acid sequence being translated in a different frame downstream of the mutation. A frameshift mutation can have various causes, such as the insertion, deletion or duplication of one or more nucleotides, but also mutations which affect pre-mRNA splicing (splice site mutations) can result in frameshifts;

(f) a "splice site mutation", which alters or abolishes the correct splicing of the pre-mRNA sequence, resulting in a protein of different amino acid sequence than the wild type. For example, one or more exons may be skipped during RNA splicing, resulting in a protein lacking the amino acids encoded by the skipped exons. Alternatively, the reading frame may be altered through incorrect splicing, or one or more introns may be retained, or alternate splice donors or acceptors may be generated, or splicing may be initiated at an alternate position (e.g. within an intron), or alternate polyadenylation signals may be generated. Correct pre-mRNA splicing is a complex process, which can be affected by various mutations in the nucleotide sequence of the FAD3-encoding genes. In higher eukaryotes, such as plants, the major spliceosome splices introns containing GU at the 5' splice site (donor site) and AG at the 3' splice site (acceptor site). This GU-AG rule (or GT-AG rule; see Lewin, Genes VI, Oxford University Press 1998, pp 885-920, ISBN 0198577788) is followed in about 99% of splice sites of nuclear eukaryotic genes, while introns containing other dinucleotides at the 5' and 3' splice site, such as GC-AG and AU-AC account for only about 1% and 0.1% respectively It is desired that the mutation(s) in the nucleic acid sequence preferably result in a mutant protein comprising significantly reduced or no enzymatic activity in vivo, i.e. C18:2 to C18:3 desaturase activity. Basically, any mutation which results in a protein comprising at least one amino acid insertion, deletion and/or substitution relative to the wild type protein can lead to significantly reduced or no enzymatic activity. It is, however, understood that mutations in certain parts of the protein are more likely to result in a reduced function of the mutant FAD3 protein, such as mutations leading to truncated proteins, whereby significant portions of the functional and/or structural domains, are lacking.

As used herein, a "full knock-out allele" is a mutant allele directing a significantly reduced or no functional FAD3 expression, i.e. a significantly reduced amount of functional FAD3 protein or no functional FAD3 protein, in the cell in vivo. Full knock-out mutant FAD3 alleles include for instance deletion mutations of the entire or a substantial part of the coding region, or frameshift or stop-codon mutations that lead to a substantial or entire deletion of the protein. For example, a full knock-out FAD3 allele comprises a mutation that disrupts or deletes the ER retention motif that is present in the 5 most C-terminal amino acids (-KSKIN). This will result in a complete loss of ER retrieval and subsequent accumulation of the protein in the Golgi or plasma membrane, rendering it incapable of performing its function (McCartney et al., 2004, Plant Journal 37, pages 156-173). Therefore, for example any stop codon, frame shift or splice site mutation that leads to a C-terminal truncation of the protein that includes the ER retention motif will result in a full knock-out FAD3 allele, as does a missense mutation (e.g. a substitution of one or both of the two lysines), insertion or deletion in the nucleotide sequence encoding the motif itself, i.e. starting from nt 1117 of SEQ ID NO: 11 (corresponding to Lys373 of SEQ ID NO: 2) and further downstream relative to the ATG start codon in the coding sequence of FAD3-A1 or homologous residues hereto.

Alternatively, a full knock-out mutant FAD3 allele comprises a mutation that deletes or disrupts any one of the eight conserved histidine residues. For example, a full knock-out mutant FAD3 allele comprises a mutation, e.g. nonsense or frameshift mutation, between nucleotide (nt) 274-276 and nt 895-897 relative to the ATG start codon in the coding sequence of FAD3-A1 (genbank accession number FJ985689.1) encoding respectively the first and last conserved histidines (His92 and His299 of the FAD3-A1 protein; genbank accession number ACS26169.1), or homologous residues hereto. In another example, missense mutations that lead to substitution of any of these eight histidine residues will result in a non-functional FAD3 protein. In yet another example, a full knock-out mutant FAD3 allele comprises insertion, deletion or splice site mutation(s) that delete or alter any of the nucleotides encoding the eight di-iron binding histidines, or alter the positioning of one ore more of the eight di-iron binding histidines with respect to the potential membrane spanning domains or to each other.

Another example of a full knock-out mutant FAD3 allele is a FAD3 allele encoding a N-terminally truncated FAD3 protein. In case of a mutation upstream of the nucleotides encoding the first di-iron histidine, an alterative ATG, downstream of the original start codon, may be used for translation initations, whereby an N-terminally truncated protein may still be formed. However, such a truncation will disrupt or delete the potential N-terminal signal sequence, which normally functions to target the protein to the ER, leading to a dislocation of FAD3 to the cytosol, thus rendering it incapable of performing its normal function.

As used herein, a "significantly reduced amount of functional FAD3 protein" (e.g. functional FAD3-A1, FAD3-A2, FAD3-A3, FAD3-C1 and/or FAD3-C2 protein) refers to a reduction in the amount of a functional FAD3 protein produced by the cell comprising a mutant FAD3 allele by at least 30%, 40%, 50%, 60%, 70%, 80%, 90%, 95% or 100% (i.e. no functional protein is produced by the cell) as compared to the amount of the functional FAD3 protein produced by the cell not comprising the mutant FAD3 allele. This definition encompasses the production of a "non-functional" FAD3 protein (e.g. truncated FAD3 protein) having no biological activity (C18:2 to C18:3 desaturase activity) in vivo, the reduction in the absolute amount of the functional FAD3 protein (e.g. no functional FAD3 protein being made due to the mutation in the FAD3 gene) and/or the production of an FAD3 protein with significantly reduced biological activity compared to the activity of a functional wild type FAD3 protein (such as an FAD3 protein in which one or more amino acid residues that are crucial for the biological activity of the encoded FAD3 protein, are substituted for another amino acid residue or deleted).

The term "mutant FAD3 protein", as used herein, refers to a FAD3 protein encoded by a mutant FAD3 nucleic acid sequence ("fad3 allele") whereby the mutation results in a significantly reduced and/or no biological FAD3 activity (C18:2 to C18:3 desaturase activity) in vivo, compared to the activity of the FAD3 protein encoded by a non-mutant, wild type FAD3 sequence ("FAD3 allele").

As used herein, "a significantly reduced C18:3 content" or "low alpha-linolenic acid" refers to a significant reduction in the amount of total alpha-linolenic acid (C18:3) present in the seed oil of a plant comprising one or more mutant FAD3 alleles when compared to the seed oil of a corresponding plant not comprising said mutant FAD3 allele(s). In another embodiment the C18:3 seed oil content of said plants comprising one or more mutant FAD3 alleles is reduced to below 11% wt, 10% wt, 9% wt, 8% wt, 7.0 wt %, 6.0 wt %, 5.0 wt %, 4.0 wt %, 3.0 wt %, 2.5 wt %, 2.0 wt %, 1.5% wt, 1.0 wt %, 0.5 wt of the total seed oil content.

It is understood that the C18:3 seed oil content may vary depending on genetic background and growth conditions (e.g. temperature). Without intending to limit the invention, it is expected that the C18:3 seed oil levels will generally be higher when plants are grown in the field than when they are grown in the greenhouse. Therefore, in order to determine whether a plant according to the invention, i.e. a plant comprising one or more mutant FAD3 alleles, has a significantly reduced C18:3 seed oil content, a comparison should be made with a corresponding plant (i.e. of the same genetic background) not comprising said mutant FAD3 allele(s) grown under the same conditions, rather than evaluating absolute C18:3 seed oil levels.

The fatty acid composition of seed oil, including the C18:3 content, can be determined using methods known in the art, for example by extracting the fatty acyls from the seeds and analyzing their relative levels in the seed oil by capillary gas-liquid chromatography as described in e.g. WO09/007091.

"Mutagenesis", as used herein, refers to the process in which plant cells (e.g., a plurality of Brassica seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more FAD3 alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, Brassica plants are regenerated from the treated cells using known techniques. For instance, the resulting Brassica seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for Brassica napus. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant FAD3 alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant FAD3 alleles are described in the Examples below.

Whenever reference is made to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the C18:3 seed oil content), such as seed obtained by selfing or crossing, e.g. hybrid seed (obtained by crossing two inbred parental lines), hybrid plants and plant parts derived there from are encompassed herein, unless otherwise indicated.

"Crop plant" refers to plant species cultivated as a crop, such as Brassica napus (AACC, 2n=38), Brassica juncea (AABB, 2n=36), Brassica carinata (BBCC, 2n=34), Brassica rapa (syn. B. campestris) (AA, 2n=20), Brassica oleracea (CC, 2n=18) or Brassica nigra (BB, 2n=16). The definition does not encompass weeds, such as Arabidopsis thaliana.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

As used herein, the term "non-naturally occurring" or "cultivated" when used in reference to a plant, means a plant with a genome that has been modified by man. A transgenic plant, for example, is a non-naturally occurring plant that contains an exogenous nucleic acid molecule, e.g., a chimeric gene comprising a transcribed region which when transcribed yields a biologically active RNA molecule capable of reducing the expression of an endogenous gene, such as a FAD3 gene according to the invention, and, therefore, has been genetically modified by man. In addition, a plant that contains a mutation in an endogenous gene, for example, a mutation in an endogenous FAD3 gene, (e.g. in a regulatory element or in the coding sequence) as a result of an exposure to a mutagenic agent is also considered a non-naturally plant, since it has been genetically modified by man. Furthermore, a plant of a particular species, such as Brassica napus, that contains a mutation in an endogenous gene, for example, in an endogenous FADS gene, that in nature does not occur in that particular plant species, as a result of, for example, directed breeding processes, such as marker-assisted breeding and selection or introgression, with a plant of the same or another species, such as Brassica juncea or rapa, of that plant is also considered a non-naturally occurring plant. In contrast, a plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring plant typically has a nucleotide sequence that is altered as compared to a naturally occurring plant, a non-naturally occurring plant also can be genetically modified by man without altering its nucleotide sequence, for example, by modifying its methylation pattern.

As used herein, "an agronomically suitable plant development" refers to a development of the plant, in particular an oilseed rape plant, which does not adversely affect its performance under normal agricultural practices, more specifically its establishment in the field, vigor, flowering time, height, maturation, lodging resistance, yield, disease resistance, resistance to pod shattering, etc. Thus, lines with significantly reduced C18: seed oil content with agronomically suitable plant development have a C18:3 seed oil content that has decreased as compared to the C18:3 seed oil content of a plant known to have an average C18:3 seed oil content while maintaining a similar establishment in the field, vigor, flowering time, height, maturation, lodging resistance, yield, disease resistance, resistance to pod shattering, etc.

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

DETAILED DESCRIPTION

*Brassica napus* (genome AACC, 2n=4×38), which is an allotetraploid (amphidiploid) species containing essentially two diploid genomes (the A and the C genome) due to its origin from diploid ancestors, is described to comprise two FAD3 genes in its genome located on the A and C genome, herein after called FAD3-A1 and FAD3-C1 respectively. It was found by the inventors that the *Brassica napus* genome contains three additional FAD3 genes, which were designated FAD3-A2, FAD3-A3 and FAD3-C2. It was found in crosses with an elite male and an elite female *Brassica* breeding line that *Brassica napus* plants that are homozygous for either a mutant FAD3-A1 or FAD3-C1 allele, show a significant decrease in C18:3 seed oil content when compared to *Brassica napus* plants not comprising mutant FAD3 alleles, while plants homozygous for a mutation in any of the newly identified FAD3 genes did not display a reduction in C18:3. It was further found that in addition to homozygosity for the FAD3-A1 or FAD3-C1 mutant alleles, the presence of a second mutant FAD3 gene in homozygous state, surprisingly also of the of the new FAD3 genes, in *Brassica napus* could further reduce C18:3 seed oil content. Moreover, in addition to both the FAD3-A1 and FAD3-C1 mutation in homozygous state, homozygosity for a third mutant FAD3 allele could reduce C18:3 content in seed oil of plants grown in the greenhouse even to below 3% of the total seed oil content. It was furthermore observed that the more additional mutant FAD3 alleles are stacked on top of the mutant alleles of the FAD3A1 and FAD3C1 genes, the lower the C18:3 oil content, both in *Brassica* plants grown in the greenhouse as well as for plants grown in the field.

Thus, in a first embodiment the invention provides a *Brassica* plant comprising at least two full knock-out mutant FAD3 alleles of two different FAD3 genes, wherein
  i. the first mutant FAD3 allele is selected from the group consisting of FAD3-A1 or FAD3-C1; and
  ii. the second mutant FAD3 allele is selected from the group consisting of FAD3-A2, FAD3-A3 or FAD3-C2.

In one embodiment double mutant plants are provided herein that are heterozygous or homozygous for the first mutant FAD3 allele and heterozygous or homozygous for the second mutant FAD3 allele, wherein the genotype of the plant can be described as (the mutant FAD3 allele is abbreviated to fad3 while the wild type allele is depicted as FAD3):
  FAD3-A1/fad3-a1, FAD3-A2/fad3-a2
  FAD3-A1/fad3-a1, FAD3-A3/fad3-a3
  FAD3-A1/fad3-a1, FAD3-C2/fad3-c2
  FAD3-C1/fad3-c1, FAD3-A2/fad3-a2
  FAD3-C1/fad3-c1, FAD3-A3/fad3-a3
  FAD3-C1/fad3-c1, FAD3-C2/fad3-c2
  fad3-a1/fad3-a1, FAD3-A2/fad3-a2
  fad3-a1/fad3-a1, FAD3-A3/fad3-a3
  fad3-a1/fad3-a1, FAD3-C2/fad3-c2
  fad3-c1/fad3-c1, FAD3-A2/fad3-a2
  fad3-c1/fad3-c1, FAD3-A3/fad3-a2
  fad3-c1/fad3-c1, FAD3-C2/fad3-c2
  FAD3-A1/fad3-a1, fad3-a2/fad3-a2
  FAD3-A1/fad3-a1, fad3-a3/fad3-a3
  FAD3-A1/fad3-a1, fad3-c2/fad3-c2
  FAD3-C1/fad3-c1, fad3-a2/fad3-a2
  FAD3-C1/fad3-c1, fad3-a3/fad3-a3
  FAD3-C1/fad3-c1, fad3-c1/fad3-c2
  fad3-a1/fad3-a1, fad3-a2/fad3-a2
  fad3-a1/fad3-a1, fad3-a3/fad3-a3
  fad3-a1/fad3-a1, fad3-c2/fad3-c2
  fad3-c1/fad3-c1, fad3-a2/fad3-a2
  fad3-c1/fad3-c1, fad3-a3/fad3-a2
  fad3-c1/fad3-c1, fad3-c1/fad3-c2
wherein the plant is homozygous for the wild type alleles of the remaining FAD3 genes (e.g. FAD3-A1/fad3-a1, FAD3-A2/fad3-a2 corresponds to the genotype FAD3-A1/fad3-a1, FAD3-A2/fad3-a2, FAD3-A3/FAD3-A3, FAD3-C1/FAD3-C1, FAD3-C2/FAD3-C2)

The invention also provides a plant further comprising a third full knock-out mutant FAD3 allele, wherein said third full knock-out mutant FAD3 allele is selected from the group consisting of FAD3-A1 or FAD3-C1, whereby the mutant FAD3 alleles are mutant alleles of at least three different FAD3 genes.

It will be clear to the skilled person that when FAD3-A1 is chosen as the first full knock-out mutant FAD3 allele, the third full knock-out mutant FAD3 allele will be FAD3-C1, and vice versa.

Thus, in another embodiment triple mutant plants are provided herein that are heterozygous or homozygous for the first mutant FAD3 allele, heterozygous or homozygous for the second mutant FAD3 allele and heterozygous or homozygous for the third mutant FAD3 allele, wherein the genotype of the plant can be described as (the mutant FAD3 allele is abbreviated to fad3 while the wild type allele is depicted as FAD3):
  FAD3-A1/fad3-a1, FAD3-A2/fad3-a2, FAD3-C1/fad3-c1
  FAD3-A1/fad3-a1, FAD3-A3/fad3-a3, FAD3-C1/fad3-c1
  FAD3-A1/fad3-a1, FAD3-C2/fad3-c2, FAD3-C1/fad3-c1
  fad3-a1/fad3-a1, FAD3-A2/fad3-a2, FAD3-C1/fad3-c1
  fad3-a1/fad3-a1, FAD3-A3/fad3-a3, FAD3-C1/fad3-c1
  fad3-a1/fad3-a1, FAD3-C2/fad3-c2, FAD3-C1/fad3-c1
  FAD3-A1/fad3-a1, fad3-a2/fad3-a2, FAD3-C1/fad3-c1
  FAD3-A1/fad3-a1, fad3-a3/fad3-a3, FAD3-C1/fad3-c1
  FAD3-A1/fad3-a1, fad3-c2/fad3-c2, FAD3-C1/fad3-c1
  FAD3-A1/fad3-a1, FAD3-A2/fad3-a2, fad3-c1/fad3-c1
  FAD3-A1/fad3-a1, FAD3-A3/fad3-a3, fad3-c1/fad3-c1
  FAD3-A1/fad3-a1, FAD3-C2/fad3-c2, fad3-c1/fad3-c1
  fad3-a1/fad3-a1, FAD3-A2/fad3-a2, fad3-c1/fad3-c1
  fad3-a1/fad3-a1, FAD3-A3/fad3-a3, fad3-c1/fad3-c1
  fad3-a1/fad3-a1, FAD3-C2/fad3-c2, fad3-c1/fad3-c1
  fad3-a1/fad3-a1, fad3-a2/fad3-a2, FAD3-C1/fad3-c1
  fad3-a1/fad3-a1, fad3-a3/fad3-a3, FAD3-C1/fad3-c1
  fad3-a1/fad3-a1, fad3-c2/fad3-c2, FAD3-C1/fad3-c1
  FAD3-A1/fad3-a1, fad3-a2/fad3-a2, fad3-c1/fad3-c1
  FAD3-A1/fad3-a1, fad3-a3/fad3-a3, fad3-c1/fad3-c1
  FAD3-A1/fad3-a1, fad3-c2/fad3-c2, fad3-c1/fad3-c1
  fad3-a1/fad3-a1, fad3-a2/fad3-a2, fad3-c1/fad3-c1
  fad3-a1/fad3-a1, fad3-a3/fad3-a3, fad3-c1/fad3-c1
  fad3-a1/fad3-a1, fad3-c2/fad3-c2, fad3-c1/fad3-c1 wherein the plant is homozygous for the wild type alleles of the remaining FAD3 genes (e.g. FAD3-A1/fad3-a1, FAD3-A2/fad3-a2, FAD3-C1/fad3-c1 corresponds to the genotype FAD3-A1/fad3-a1, FAD3-A2/fad3-a2, FAD3-C1/fad3-c1, FAD3-A3/FAD3-A3, FAD3-C2/FAD3-C2).

It is believed that the more mutant FAD3 alleles will be combined in a plant, the greater the reduction in C18:3 seed oil content will be. Therefore, the invention also provides a plant further comprising fourth full knock-out mutant FAD3 allele, wherein said fourth full knock-out mutant FAD3 allele is selected from the group consisting of FAD3-A2, FAD3-A3 or FAD3-C2, whereby the mutant FAD3 alleles are mutant alleles of at least four different FAD3 genes.

It will be clear to the skilled person that when FAD3-A2 is chosen as the second full knock-out mutant FAD3 allele, the fourth full knock-out mutant FAD3 allele will be FAD3-A3 or FAD3-C2. Similarly, when FAD3-A3 is chosen as the second full knock-out mutant FAD3 allele, the fourth full knock-out mutant FAD3 allele will be FAD3-A2 or FAD3-C2 and when FAD3-C2 is chosen as the second full knock-out mutant FAD3 allele, the fourth full knock-out mutant FAD3 allele will be FAD3-A2 or FAD3-A3.

Thus, in another embodiment quadruple mutant plants are provided herein that are heterozygous or homozygous for the first mutant FAD3 allele, heterozygous or homozygous for the second mutant FAD3 allele, heterozygous or homozygous for the third mutant FAD3 allele and heterozygous or homozygous for the fourth mutant FAD3 allele are provided herein, wherein the genotype of the plant can be described as (the mutant FAD3 allele is abbreviated to fad3 while the wild type allele is depicted as FAD3):

FAD3-A1/fad3-a1, FAD3-A2/fad3-a2, FAD3-C1/fad3-c1, FAD3-A3/fad3-a3

FAD3-A1/fad3-a1, FAD3-A2/fad3-a2, FAD3-C1/fad3-c1, FAD3-C2/fad3-c2

FAD3-A1/fad3-a1, FAD3-A3/fad3-a3, FAD3-C1/fad3-c1, FAD3-C2/fad3-c2

FAD3-A1/fad3-a1, FAD3-A2/fad3-a2, FAD3-C1/fad3-c1, fad3-a3/fad3-a3

FAD3-A1/fad3-a1, FAD3-A2/fad3-a2, FAD3-C1/fad3-c1, fad3-c2/fad3-c2

FAD3-A1/fad3-a1, FAD3-A3/fad3-a3, FAD3-C1/fad3-c1, fad3-c2/fad3-c2

FAD3-A1/fad3-a1, FAD3-A2/fad3-a2, fad3-c1/fad3-c1, FAD3-A3/fad3-a3

FAD3-A1/fad3-a1, FAD3-A2/fad3-a2, fad3-c1/fad3-c1, FAD3-C2/fad3-c2

FAD3-A1/fad3-a1, FAD3-A3/fad3-a3, fad3-c1/fad3-c1, FAD3-C2/fad3-c2

FAD3-A1/fad3-a1, fad3-a2/fad3-a2, FAD3-C1/fad3-c1, FAD3-A3/fad3-a3

FAD3-A1/fad3-a1, fad3-a2/fad3-a2, FAD3-C1/fad3-c1, FAD3-C2/fad3-c2

FAD3-A1/fad3-a1, fad3-a3/fad3-a3, FAD3-C1/fad3-c1, FAD3-C2/fad3-c2 fad3-a1/fad3-a1, FAD3-A2/fad3-a2, FAD3-C1/fad3-c1, FAD3-A3/fad3-a3 fad3-a1/fad3-a1, FAD3-A2/fad3-a2, FAD3-C1/fad3-c1, FAD3-C2/fad3-c2 fad3-a1/fad3-a1, FAD3-A3/fad3-a3, FAD3-C1/fad3-c1, FAD3-C2/fad3-c2 fad3-a1/fad3-a1, FAD3-A2/fad3-a2, fad3-c1/fad3-c1, FAD3-A3/fad3-a3 fad3-a1/fad3-a1, FAD3-A2/fad3-a2, fad3-c1/fad3-c1, FAD3-C2/fad3-c2 fad3-a1/fad3-a1, FAD3-A3/fad3-a3, fad3-c1/fad3-c1, FAD3-C2/fad3-c2 fad3-a1/fad3-a1, fad3-a2/fad3-a2, FAD3-C1/fad3-c1, FAD3-A3/fad3-a3 fad3-a1/fad3-a1, fad3-a2/fad3-a2, FAD3-C1/fad3-c1, FAD3-C2/fad3-c2 fad3-a1/fad3-a1, fad3-a3/fad3-a3, FAD3-C1/fad3-c1, FAD3-C2/fad3-c2 fad3-a1/fad3-a1, FAD3-A2/fad3-a2, FAD3-C1/fad3-c1, fad3-a3/fad3-a3 fad3-a1/fad3-a1, FAD3-A2/fad3-a2, FAD3-C1/fad3-c1, fad3-c2/fad3-c2 fad3-a1/fad3-a1, FAD3-A3/fad3-a3, FAD3-C1/fad3-c1, fad3-c2/fad3-c2

FAD3-A1/fad3-a1, FAD3-A2/fad3-a2, fad3-c1/fad3-c1, fad3-a3/fad3-a3

FAD3-A1/fad3-a1, FAD3-A2/fad3-a2, fad3-c1/fad3-c1, fad3-c2/fad3-c2

FAD3-A1/fad3-a1, FAD3-A3/fad3-a3, fad3-c1/fad3-c1, fad3-c2/fad3-c2

FAD3-A1/fad3-a1, fad3-a2/fad3-a2, FAD3-C1/fad3-c1, fad3-a3/fad3-a3

FAD3-A1/fad3-a1, fad3-a2/fad3-a2, FAD3-C1/fad3-c1, fad3-c2/fad3-c2

FAD3-A1/fad3-a1, fad3-a3/fad3-a3, FAD3-C1/fad3-c1, fad3-c2/fad3-c2

FAD3-A1/fad3-a1, fad3-a2/fad3-a2, fad3-c1/fad3-c1, FAD3-A3/fad3-a3

FAD3-A1/fad3-a1, fad3-a2/fad3-a2, fad3-c1/fad3-c1, FAD3-C2/fad3-c2

FAD3-A1/fad3-a1, fad3-a3/fad3-a3, fad3-c1/fad3-c1, FAD3-C2/fad3-c2

FAD3-A1/fad3-a1, fad3-a2/fad3-a2, fad3-c1/fad3-c1, fad3-a3/fad3-a3

FAD3-A1/fad3-a1, fad3-a2/fad3-a2, fad3-c1/fad3-c1, fad3-c2/fad3-c2

FAD3-A1/fad3-a1, fad3-a3/fad3-a3, fad3-c1/fad3-c1, fad3-c2/fad3-c2 fad3-a1/fad3-a1, FAD3-A2/fad3-a2, fad3-c1/fad3-c1, fad3-a3/fad3-a3 fad3-a1/fad3-a1, FAD3-A2/fad3-a2, fad3-c1/fad3-c1, fad3-c2/fad3-c2 fad3-a1/fad3-a1, FAD3-A3/fad3-a3, fad3-c1/fad3-c1, fad3-c2/fad3-c2 fad3-a1/fad3-a1, fad3-a2/fad3-a2, FAD3-C1/fad3-c1, fad3-a3/fad3-a3 fad3-a1/fad3-a1, fad3-a2/fad3-a2, FAD3-C1/fad3-c1, fad3-c2/fad3-c2 fad3-a1/fad3-a1, fad3-a3/fad3-a3, FAD3-C1/fad3-c1, fad3-c2/fad3-c2 fad3-a1/fad3-a1, fad3-a2/fad3-a2, fad3-c1/fad3-c1, FAD3-A3/fad3-a3 fad3-a1/fad3-a1, fad3-a2/fad3-a2, fad3-c1/fad3-c1, FAD3-C2/fad3-c2 fad3-a1/fad3-a1, fad3-a3/fad3-a3, fad3-c1/fad3-c1, FAD3-C2/fad3-c2 fad3-a1/fad3-a1, fad3-a2/fad3-a2, fad3-c1/fad3-c1, fad3-a3/fad3-a3 fad3-a1/fad3-a1, fad3-a2/fad3-a2, fad3-c1/fad3-c1, fad3-c2/fad3-c2 fad3-a1/fad3-a1, fad3-a3/fad3-a3, fad3-c1/fad3-c1, fad3-c2/fad3-c2 wherein the plant is homozygous for the wild type alleles of the remaining FAD3 genes (e.g. FAD3-A1/fad3-a1, FAD3-A2/fad3-a2, FAD3-C1/fad3-c1, FAD3-A3/fad3-a3 corresponds to the genotype FAD3-A1/fad3-a1, FAD3-A2/fad3-a2, FAD3-C1/fad3-c1, FAD3-A3/fad3-a3, FAD3-C2/FAD3-C2).

The invention furthermore provides a plant further comprising a fifth full knock-out mutant FAD3 allele, wherein said fifth full knock-out mutant FAD3 allele is selected from the group consisting of FAD3-A2, FAD3-A3 or FAD3-C2, whereby the mutant FAD3 alleles are mutant alleles of at least five different FAD3 genes.

Thus, in another embodiment quintuple mutant plants are provided herein that are heterozygous or homozygous for the first mutant FAD3 allele, heterozygous or homozygous for the second mutant FAD3 allele, heterozygous or homozygous for the third mutant FAD3 allele, heterozygous or homozygous for the fourth mutant FAD3 allele and heterozygous or homozygous for the fifth mutant FAD3 allele, wherein the genotype of the plant can be described as (the mutant FAD3 allele is abbreviated to fad3 while the wild type allele is depicted as FAD3):

FAD3-A1/fad3-a1, FAD3-A2/fad3-a2, FAD3-A3/fad3-a3, FAD3-C1/fad3-c1, FAD3-C2/fad3-c2
fad3-a1/fad3-a1, FAD3-A2/fad3-a2, FAD3-A3/fad3-a3, FAD3-C1/fad3-c1, FAD3-C2/fad3-c2
FAD3-A1/fad3-a1, fad3-a2/fad3-a2, FAD3-A3/fad3-a3, FAD3-C1/fad3-c1, FAD3-C2/fad3-c2
FAD3-A1/fad3-a1, FAD3-A2/fad3-a2, fad3-a3/fad3-a3, FAD3-C1/fad3-c1, FAD3-C2/fad3-c2
FAD3-A1/fad3-a1, FAD3-A2/fad3-a2, FAD3-A3/fad3-a3, fad3-c1/fad3-c1, FAD3-C2/fad3-c2
FAD3-A1/fad3-a1, FAD3-A2/fad3-a2, FAD3-A3/fad3-a3, FAD3-C1/fad3-c1, fad3-c2/fad3-c2
fad3a1/fad3-a1, fad3-a2/fad3-a2, FAD3-A3/fad3-a3, FAD3-C1/fad3-c1, FAD3-C2/fad3-c2
fad3a1/fad3-a1, FAD3-A2/fad3-a2, fad3-a3/fad3-a3, FAD3-C1/fad3-c1, FAD3-C2/fad3-c2
fad3a1/fad3-a1, FAD3-A2/fad3-a2, FAD3-A3/fad3-a3, fad3-c1/fad3-c1, FAD3-C2/fad3-c2
fad3a1/fad3-a1, FAD3-A2/fad3-a2, FAD3-A3/fad3-a3, FAD3-C1/fad3-c1, fad3-c2/fad3-c2
FAD3-A1/fad3-a1, fad3-a2/fad3-a2, fad3-a3/fad3-a3, FAD3-C1/fad3-c1, FAD3-C2/fad3-c2
FAD3-A1/fad3-a1, fad3-a2/fad3-a2, FAD3-A3/fad3-a3, fad3-c1/fad3-c1, FAD3-C2/fad3-c2
FAD3-A1/fad3-a1, fad3-a2/fad3-a2, FAD3-A3/fad3-a3, FAD3-C1/fad3-c1, fad3-c2/fad3-c2
FAD3-A1/fad3-a1, FAD3-A2/fad3-a2, fad3-a3/fad3-a3, fad3-c1/fad3-c1, FAD3-C2/fad3-c2
FAD3-A1/fad3-a1, FAD3-A2/fad3-a2, fad3-a3/fad3-a3, FAD3-C1/fad3-c1, fad3-c2/fad3-c2
FAD3-A1/fad3-a1, FAD3-A2/fad3-a2, FAD3-A3/fad3-a3, fad3-c1/fad3-c1, fad3-c2/fad3-c2
fad3-a1/fad3-a1, fad3-a2/fad3-a2, fad3-a3/fad3-a3, FAD3-C1/fad3-c1, FAD3-C2/fad3-c2
fad3-a1/fad3-a1, fad3-a2/fad3-a2, fad3-a3/fad3-a3, FAD3-C1/fad3-c1, fad3-c2/fad3-c2
fad3-a1/fad3-a1, fad3-a2/fad3-a2, FAD3-A3/fad3-a3, fad3-c1/fad3-c1, FAD3-C2/fad3-c2
fad3-a1/fad3-a1, FAD3-A2/fad3-a2, fad3-a3/fad3-a3, fad3-c1/fad3-c1, FAD3-C2/fad3-c2
fad3-a1/fad3-a1, FAD3-A2/fad3-a2, fad3-a3/fad3-a3, FAD3-C1/fad3-c1, fad3-c2/fad3-c2
fad3-a1/fad3-a1, FAD3-A2/fad3-a2, FAD3-A3/fad3-a3, fad3-c1/fad3-c1, fad3-c2/fad3-c2
FAD3-A1/fad3-a1, fad3-a2/fad3-a2, fad3-a3/fad3-a3, fad3-c1/fad3-c1, FAD3-C2/fad3-c2
FAD3-A1/fad3-a1, fad3-a2/fad3-a2, fad3-a3/fad3-a3, FAD3-C1/fad3-c1, fad3-c2/fad3-c2
FAD3-A1/fad3-a1, fad3-a2/fad3-a2, FAD3-A3/fad3-a3, fad3-c1/fad3-c1, fad3-c2/fad3-c2
FAD3-A1/fad3-a1, FAD3-A2/fad3-a2, fad3-a3/fad3-a3, fad3-c1/fad3-c1, fad3-c2/fad3-c2
fad3-a1/fad3-a1, fad3-a2/fad3-a2, fad3-a3/fad3-a3, fad3-c1/fad3-c1, FAD3-C2/fad3-c2
fad3-a1/fad3-a1, fad3-a2/fad3-a2, fad3-a3/fad3-a3, FAD3-C1/fad3-c1, fad3-c2/fad3-c2
fad3-a1/fad3-a1, fad3-a2/fad3-a2, daf3-a3/fad3-a3, FAD3-C1/fad3-c1, fad3-c2/fad3-c2
fad3-a1/fad3-a1, fad3-a2/fad3-a2, FAD3-A3/fad3-a3, fad3-c1/fad3-c1, fad3-c2/fad3-c2
fad3-a1/fad3-a1, FAD3-A2/fad3-a2, fad3-a3/fad3-a3, fad3-c1/fad3-c1, fad3-c2/fad3-c2
FAD3-A1/fad3-a1, fad3-a2/fad3-a2, fad3-a3/fad3-a3, fad3-c1/fad3-c1, fad3-c2/fad3-c2
fad3-a1/fad3-a1, fad3-a2/fad3-a2, fad3-a3/fad3-a3, fad3-c1/fad3-c1, fad3-c2/fad3-c2

In another embodiment the plants of the invention comprises mutant FAD3 alleles comprising a nonsense (stopcodon) mutation.

In yet another embodiment the plants of the invention comprise mutant FAD3 alleles that are selected from the group consisting of LOLI105, LOLI103, LOLI108, LOLI111 or LOLI115.

As used herein, LOLI105 or LOLI105 is a mutant allele of a FAD3-A1 genomic sequence, coding sequence or amino acid sequence of respectively SEQ ID NO: 11 or SEQ ID NO: 2, comprising a mutation in SEQ ID NO: 1 at nucleotide position 2405, in SEQ ID NO: 11 at nucleotide position 732 or in SEQ ID NO: 2 at amino acid position 244, resulting in a codon change in SEQ ID NO: 1 or SEQ ID NO: 11 of TGG to TGA or an amino acid change in SEQ ID NO: 2 of Trp to stop.

As used herein, LOLI103 or LOLI103 is a mutant allele of a FAD3-C1 genomic sequence, coding sequence or amino acid sequence of respectively SEQ ID NO: 3, SEQ ID NO: 12 or SEQ ID NO: 4, comprising a mutation in SEQ ID NO: 3 at nucleotide position 2702, in SEQ ID NO: 12 at nucleotide position 543 or in SEQ ID NO: 4 at amino acid position 181, resulting in a codon change in SEQ ID NO: 3 or SEQ ID NO: 12 of TGG to TGA or amino acid change in SEQ ID NO: 4 of Trp to stop.

As used herein, LOLI108 or LOLI108 is a mutant allele of a FAD3-A2 genomic sequence, coding sequence or aminoacid sequence of respectively SEQ ID NO: 5, SEQ ID NO: 13 or SEQ ID NO: 6, comprising a mutation in SEQ ID NO: 5 at nucleotide position 3934, in SEQ ID NO: 13 at nucleotide position 749 or in SEQ ID NO: 6 at amino acid position 250, resulting in a codon change in SEQ ID NO: 5 or SEQ ID NO: 13 of TGG to TAG or an amino acid change in SEQ ID NO: 6 of Trp to stop.

As used herein, LOLI111 or LOLI111 is a mutant allele of a FAD3-A3 genomic sequence, coding sequence or aminoacid sequence of respectively SEQ ID NO: 7, SEQ ID NO: 14 or SEQ ID NO: 8, comprising a mutation in SEQ ID NO: 7 at nucleotide position 2847, in SEQ ID NO: 14 at nucleotide position 552 or in SEQ ID NO: 8 at amino acid position 184, resulting in a codon change in SEQ ID NO: 7 or SEQ ID NO: 14 of TGG to TGA or an amino acid change in SEQ ID NO: 8 of Trp to stop.

As used herein, LOLI115 or LOLI115 is a mutant allele of a FAD3-C2 genomic sequence, coding sequence or aminoacid sequence of respectively SEQ ID NO: 9, SEQ ID NO: 15 or SEQ ID NO: 10, comprising a mutation in SEQ ID NO: 9 at nucleotide position 3909, in SEQ ID NO: 15 at nucleotide position 551 or in SEQ ID NO: 10 at amino acid position 184, resulting in a codon change in SEQ ID NO: 9 or SEQ ID NO: 15 of TGG to TAG or an amino acid change in SEQ ID NO: 10 of Trp to stop.

In one embodiment, the plant of the invention may produce a significantly reduced amount of functional FAD3 protein compared to the amount of functional FAD3 protein produced by a corresponding plant not comprising the mutant FAD3 alleles of the invention. In another embodiment, the seed of the plant may have a significantly reduced C18:3 seed oil content compared to plants not comprising the mutant FAD3 alleles.

Further provided herein are nucleic acid sequences of wild type and mutant FAD3 genes/alleles from *Brassica* species, as well as the wild type and mutant FAD3 proteins. Also provided are methods of generating and combining mutant and wild type FAD3 alleles in *Brassica* plants, as well as *Brassica* plants and plant parts comprising specific combinations of wild type and mutant FAD3 alleles in their genome, whereby the C18:3 seed oil content is decreased. The use of these plants for transferring mutant FAD3 alleles to other plants is also an embodiment of the invention, as are the plant products of any of the plants described. In addition kits and methods for marker assisted selection (MAS) for combining or detecting FAD3 genes and/or alleles are provided. Each of the embodiments of the invention is described in detail herein below.

Nucleic Acid Sequences According to the Invention

Provided are both wild type FAD3 nucleic acid sequences encoding functional FAD3 proteins and mutant FAD3 nucleic acid sequences (comprising one or more mutations, preferably mutations which result in no or a significantly reduced biological activity of the encoded FAD3 protein or in no FAD3 protein being produced) of FAD3 genes from Brassicaceae, particularly from *Brassica* species, especially from *Brassica napus*, but also from other *Brassica* crop species. For example, *Brassica* species comprising an A and/or a C genome may comprise different alleles of FAD3 genes, which can be identified and combined in a single plant according to the invention. In addition, mutagenesis methods can be used to generate mutations in wild type FAD3 alleles, thereby generating mutant FAD3 alleles for use according to the invention. Because specific FAD3 alleles are preferably combined in a plant by crossing and selection, in one embodiment the FAD3 nucleic acid sequences are provided within a plant (i.e. endogenously), e.g. a *Brassica* plant, preferably a *Brassica* plant which can be crossed with *Brassica napus* or which can be used to make a "synthetic" *Brassica napus* plant. Hybridization between different *Brassica* species is described in the art, e.g., as referred to in Snowdon (2007, Chromosome research 15: 85-95). Interspecific hybridization can, for example, be used to transfer genes from, e.g., the C genome in *B. napus* (AACC) to the C genome in *B. carinata* (BBCC), or even from, e.g., the C genome in *B. napus* (AACC) to the B genome in *B. juncea* (AABB) (by the sporadic event of illegitimate recombination between their C and B genomes). "Resynthesized" or "synthetic" *Brassica napus* lines can be produced by crossing the original ancestors, *B. oleracea* (CC) and *B. rapa* (AA). Interspecific, and also intergeneric, incompatibility barriers can be successfully overcome in crosses between *Brassica* crop species and their relatives, e.g., by embryo rescue techniques or protoplast fusion (see e.g. Snowdon, above).

However, isolated FAD3 and FAD3 nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described herein) and for selection and transfer of specific alleles from one plant into another, in order to generate a plant having the desired combination of functional and mutant alleles.

Nucleic acid sequences of FAD3 alleles have been isolated from *Brassica napus* as depicted in the sequence listing. The wild type FAD3 sequences are depicted, while the mutant FAD3 sequences of these sequences, and of sequences essentially similar to these, are described herein below and in the Examples, with reference to the wild type FAD3 sequences. The genomic FAD3 protein-encoding DNA, and corresponding pre-mRNA, comprises 8 exons (numbered exons 1-8 starting from the 5' end) interrupted by 7 introns (numbered introns 1-7, starting from the 5'end). In the cDNA and corresponding processed mRNA (i.e. the spliced RNA), introns are removed and exons are joined, as depicted in the sequence listing. Exon sequences are more conserved evolutionarily and are therefore less variable than intron sequences.

"FAD3-A1 nucleic acid sequences" or "FAD3-A1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 2 or nucleic acid sequences having at least 80%, at least 85%, at least 90%, at least 95%, 96%, 97%, 98%, 99% or 100% sequence identity with SEQ ID NO: 1 or SEQ ID NO: 11. These nucleic acid sequences may also be referred to as being "essentially similar" or "essentially identical" to the FAD3 sequences provided in the sequence listing.

"FAD3-C1 nucleic acid sequences" or "FAD3-C1 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 4 or nucleic acid sequences having at least 80%, at least 85%, at least 90%, at least 95%, 96%, 97%, 98%, 99% or 100% sequence identity with SEQ ID NO: 3 or SEQ ID NO: 12 These nucleic acid sequences may also be referred to as being "essentially similar" or "essentially identical" to the FAD3 sequences provided in the sequence listing.

"FAD3-A2 nucleic acid sequences" or "FAD3-A2 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 6 or nucleic acid sequences having at least 80%, at least 85%, at least 90%, at least 95%, 96%, 97%, 98%, 99% or 100% sequence identity with SEQ ID NO: 5 or SEQ ID NO: 13. These nucleic acid sequences may also be referred to as being "essentially similar" or "essentially identical" to the FAD3 sequences provided in the sequence listing.

"FAD3-A3 nucleic acid sequences" or "FAD3-A3 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 8 or nucleic acid sequences having at least 80%, at least 85%, at least 90%, at least 95%, 96%, 97%, 98%, 99% or 100% sequence identity with SEQ ID NO: 7 or SEQ ID NO: 14. These nucleic acid sequences may also be referred to as being "essentially similar" or "essentially identical" to the FAD3 sequences provided in the sequence listing.

"FAD3-C2 nucleic acid sequences" or "FAD3-C2 variant nucleic acid sequences" according to the invention are nucleic acid sequences encoding an amino acid sequence having at least 75%, at least 80%, at least 85%, at least 90%, at least 95%, 98%, 99% or 100% sequence identity with SEQ ID NO: 10 or nucleic acid sequences having at least 80%, at least 85%, at least 90%, at least 95%, 96%, 97%, 98%, 99% or 100% sequence identity with SEQ ID NO: 9 or SEQ ID NO: 15. These nucleic acid sequences may also be referred to as being "essentially similar" or "essentially identical" to the FAD3 sequences provided in the sequence listing.

Thus the invention provides both nucleic acid sequences encoding wild type, functional FAD3 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type FAD3 protein. As already mentioned, preferably the mutation(s) in the nucleic acid sequence result in one or more amino acid changes (i.e. in relation to the wild type amino acid sequence one or more amino acids are inserted, deleted and/or substituted) whereby the biological activity of the FAD3 protein is significantly reduced or completely abolished or whereby a significantly reduced amount of functional FAD3 protein or no functional FAD3 protein is expressed. A significant reduction in or complete abolishment of the biological activity of the FAD3 protein refers herein to a deletion or disruption of structurally and/or functionally relevant amino acid residues or domains, such as the C-terminal ER retention motif, a deletion, substitution or repositioning of any of the eight conserved histidines, and/or a deletion or disruption the signal sequence, such that the C18:3 seed oil content of a plant expressing the mutant FAD3 allele is decreased as compared to a plant expressing the corresponding wild type FAD3 allele.

Both endogenous and isolated nucleic acid sequences are provided herein. Also provided are fragments of the FAD3 sequences and FAD3 variant nucleic acid sequences defined above, for use as primers or probes and as components of kits according to another aspect of the invention (see further below). A "fragment" of a FAD3 or FAD3 nucleic acid sequence or variant thereof (as defined) may be of various lengths, such as at least 10, 20, 50, 100, 200, 500, 1000, 1100 contiguous nucleotides of the FAD3 coding sequence (or of the variant sequence) or such as at least 10, 20, 50, 100, 200, 500, 1000, 2000, 2900 contiguous nucleotides of the FAD3 genome sequence (or of the variant sequence)

Nucleic Acid Sequences Encoding Functional FAD3 Proteins

The nucleic acid sequences depicted in the sequence listing encode wild type, functional FAD3 proteins from *Brassica napus*. Thus, these sequences are endogenous to the *Brassica napus* plants from which they were isolated. Other *Brassica* crop species, varieties, breeding lines or wild accessions may be screened for other FAD3 alleles, encoding the same FAD3 proteins or variants thereof. For example, nucleic acid hybridization techniques (e.g. Southern blot analysis, using for example stringent hybridization conditions) or PCR-based techniques may be used to identify FAD3 alleles endogenous to other *Brassica* plants, such as various *Brassica napus* varieties, lines or accessions, but also *Brassica juncea* (especially FAD3 alleles on the A-genome), *Brassica carinata* (especially FAD3 alleles on the C-genome) and *Brassica rapa* (A-genome) and *Brassica oleracea* (C-genome) plants, organs and tissues can be screened for other wild type FAD3 alleles. Also, *Brassica nigra* (B-genome), *Brassica carinata* (B- and C-genome), and *Brassica juncea* (A- and B-genome) plants, organs and tissues can be screened for FAD3 alleles on the B-genome. To screen such plants, plant organs or tissues for the presence of FAD3 alleles, the FAD3 nucleic acid sequences provided in the sequence listing, or variants or fragments of any of these, may be used. For example whole sequences or fragments may be used as probes or primers. For example specific or degenerate primers may be used to amplify nucleic acid sequences encoding FAD3 proteins from the genomic DNA or cDNA of the plant, plant organ or tissue. These FAD3 nucleic acid sequences may be isolated and sequenced using standard molecular biology techniques. Bioinformatics analysis may then be used to characterize the allele(s), for example in order to determine which FAD3 allele the sequence corresponds to and which FAD3 protein or protein variant is encoded by the sequence.

Whether a nucleic acid sequence encodes a functional FAD3 protein can be analyzed by recombinant DNA techniques as known in the art, e.g., by a genetic complementation test using, e.g., an *Arabidopsis* plant, which is homozygous for a full knock-out FAD3, or by methods as described above.

In addition, it is understood that FAD3 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below.

Nucleic Acid Sequences Encoding Mutant FAD3 Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as fad3 sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded FAD3 protein (i.e. it is not a "silent mutation"). In another embodiment, the mutation(s) in the nucleic acid sequence result in a significantly reduced or completely abolished biological activity of the encoded FAD3 protein relative to the wild type protein.

The nucleic acid molecules may, thus, comprise one or more mutations, such as: a missense mutation, nonsense mutation or "STOP codon mutation, an insertion or deletion mutation, a frameshift mutation and/or a splice site mutation, as is already described in detail above.

As already mentioned, it is desired that the mutation(s) in the nucleic acid sequence preferably result in a significantly reduced amount of or no functional FAD3 protein in the cell in vivo. Basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant FAD3 protein, such as mutations leading to truncated proteins, whereby significant portions of the functional amino acid residues or domains, such as the ER retention signal, the eight conserved histidine residues or the signal sequence, are deleted or substituted.

Thus in one embodiment, nucleic acid sequences comprising one or more of any of the types of mutations described above are provided. In another embodiment, fad3 sequences comprising one or more stop codon (nonsense) mutations are provided. Any of the above mutant nucleic acid sequences are provided per se (in isolated form), as are plants and plant parts comprising such sequences endogenously. In Table 2 herein below the most preferred fad3 alleles are described.

A nonsense mutation in a FAD3 allele, as used herein, is a mutation in a FAD3 allele whereby one or more translation stop codons are introduced into the coding DNA and the corresponding mRNA sequence of the corresponding wild type FAD3 allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. In one embodiment, a mutant FAD3 allele comprising a nonsense mutation is an FAD3 allele wherein an in-frame stop codon is introduced in the FAD3 codon sequence by a single nucleotide substitution, such as LOLI103, LOLI105, LOLI108, LOLI111 and LOLI115. In another embodiment, a mutant FAD3 allele comprising a nonsense mutation is a FAD3 allele wherein an in-frame stop codon is introduced in the FAD3 coding sequence by double nucleotide substitutions. In yet another embodiment, a mutant FAD3 allele comprising a nonsense mutation is a FAD3 allele wherein an in-frame stop codon is introduced in the FAD3 coding sequence by triple nucleotide substitutions. The truncated protein lacks the amino acids encoded by the coding DNA downstream (3') of the mutation (i.e. the C-terminal part of the FAD3 protein) and maintains the amino acids encoded by the coding DNA upstream (5') of the mutation (i.e. the N-terminal part of the FAD3 protein). In one embodiment, the invention provides a mutant FAD3 allele comprising a nonsense mutation is a FAD3 allele wherein the nonsense mutation is present anywhere upstream of or including the nucleotides encoding the ER retention motive (nt 1117-1131 of SEQ ID NO: 11), so that at least lysine 375 and/or lysine 373, or homologues residues hereto, are lacking.

The more truncated the mutant FAD3 protein is in comparison to the wild type FAD3 protein, the more likely the truncation may result in a significantly reduced or no functionality of the FAD3 protein in vivo. Therefore, in another embodiment, the invention provides a mutant FAD3 allele comprising a nonsense mutation upstream of or including nt 895-897, nt 892-894 or nt 883-885 of SEQ ID NO: 11, i.e. resulting in a truncated protein of less than about 299, 298 or 295 amino acids of SEQ ID NO: 2 (lacking the eighth, seventh, and/or sixth conserved histidines of the third his-box). In yet another embodiment, the invention provides a mutant FAD3 allele comprising a nonsense mutation upstream of or including nt 394-396, nt 391-393 or nt 382-384 of SEQ ID NO: 11, i.e. resulting in a truncated protein of less than about 131, 130 or 128 amino acids of SEQ ID NO: 2 (lacking the fifth, fourth and/or third histidines of the second His-box). In yet another embodiment, the invention provides a mutant FAD3 allele comprising a nonsense mutation upstream of or including nt 286-288 or nt 274-276 of SEQ ID NO: 11, i.e. resulting in a truncated protein of less than about 96 or 92 amino acids of SEQ ID NO: 2 (lacking the second and/or first sixth conserved histidines of the first His-box). As already mentioned, corresponding regions or residues in other FAD3 nucleic acid sequences and FAD3 amino acid sequences can be identified by determining the optimal alignment.

In yet another embodiment, the invention provides mutant FAD3 allele comprising a nonsense mutation which results in the usage of an alternative ATG as start codon and the synthesis of an N-terminally truncated protein lacking the putative signal sequence.

A missense mutation in a FAD3 allele, as used herein, is any mutation (deletion, insertion or substitution) in a FAD3 allele whereby one or more codons are changed into the coding DNA and the corresponding mRNA sequence of the corresponding wild type FAD3 allele, resulting in the substitution of one or more amino acids in the wild type FAD3 protein for one or more other amino acids in the mutant FAD3 protein. In one embodiment, a mutant FAD3 allele comprising a missense mutation is an FAD3 allele wherein one or more of amino acids of the ER retention motif, i.e. residues 373-377, especially lysine 373 and/or 375 of FAD3-A1, or homologous residues hereto, are substituted. Such mutations will lead to a loss of ER localization. Also missense mutations which result in the substitution of one or more of the eight conserved di-iron binding histidine residues will in a complete loss of protein function. Further, missense mutations which result in the substitution of, amino acids in the N-terminal signal sequence are likely to result in a non-functional enzyme, due to loss of its ER localization.

A frameshift mutation in a FAD3 allele, as used herein, is a mutation (deletion, insertion, duplication, and the like) in a FAD3 allele that results in the nucleic acid sequence being translated in a different frame downstream of the mutation leading to a significantly reduced amount of or no functional FAD3 enzyme in vivo.

A splice site mutation in a FAD3 allele is a mutation that results in aberrant splicing of the pre-mRNA thereby resulting in a mutant protein having significantly reduced or no activity. Any mutation (insertion, deletion and/or substitution of one or more nucleotides) which alters pre-mRNA splicing and thereby leads to a significantly reduced amount of or no functional FAD3 enzyme in vivo is encompassed herein. In one embodiment, a mutant FAD3 allele comprising a splice site mutation is a FAD3 allele wherein altered splicing is caused by the introduction in the FAD3 transcribed DNA region of one or more nucleotide substitution(s) of the consensus dinucleotides of the 5' splice site or 3' splice site, as described above. For example, GU may for example be mutated to AU in the donor splice site and/or AG may be mutated to AA in the acceptor splice site sequence.

Amino Acid Sequences According to the Invention

Provided are both wild type (functional) FAD3 amino acid sequences and mutant FAD3 amino acid sequences (comprising one or more mutations, preferably mutations which result in a significantly reduced amount of functional FAD3 enzyme or no functional FAD3 enzyme in vivo) from Brassicaceae, particularly from *Brassica* species, especially from *Brassica napus*, but also from other *Brassica* crop species. For example, *Brassica* species comprising an A and/or a C genome may encode different FAD3 amino acids. In addition, mutagenesis methods can be used to generate mutations in wild type FAD3 alleles, thereby generating mutant alleles which can encode further mutant FAD3 proteins. In one embodiment the wild type and/or mutant FAD3 amino acid sequences are provided within a *Brassica* plant (i.e. endogenously). However, isolated FAD3 amino acid sequences (e.g. isolated from the plant or made synthetically), as well as variants thereof and fragments of any of these are also provided herein.

Amino acid sequences of FAD3 proteins have been deduced from the genomic DNA FAD3 sequences that have been isolated from *Brassica napus* as depicted in the sequence listing. The wild type FAD3 sequences are depicted, while the mutant FAD3 sequences of these sequences, and of sequences essentially similar to these, are described herein below, with reference to the wild type FAD3 sequences. The FAD3 proteins of *Brassica* described herein are 377 to 388 amino acids in length and comprise a number of structural and functional domains and amino acid residues, as described above.

"FAD3-A1 amino acid sequences" or "FAD3-A1 variant amino acid sequences" according to the invention are amino acid sequences having at least 75%, at least 80%, at least 85%, at least 90%, at least 95%, 98%, 99% or 100% sequence identity with SEQ ID NO: 2. These amino acid sequences may also be referred to as being "essentially similar" or "essentially identical" to the FAD3 sequences provided in the sequence listing.

"FAD3-C1 amino acid sequences" or "FAD3-C1 variant amino acid sequences" according to the invention are amino acid sequences having at least 75%, at least 80%, at least 85%, at least 90%, at least 95%, 98%, 99% or 100% sequence identity with SEQ ID NO: 4. These amino acid sequences may also be referred to as being "essentially similar" or "essentially identical" to the FAD3 sequences provided in the sequence listing.

"FAD3-A2 amino acid sequences" or "FAD3-A2 variant amino acid sequences" according to the invention are amino acid sequences having at least 75%, at least 80%, at least 85%, at least 90%, at least 95%, 98%, 99% or 100% sequence identity with SEQ ID NO: 6. These amino acid sequences may also be referred to as being "essentially similar" or "essentially identical" to the FAD3 sequences provided in the sequence listing.

"FAD3-A3 amino acid sequences" or "FAD3-A3 variant amino acid sequences" according to the invention are amino acid sequences having at least 75%, at least 80%, at least 85%, at least 90%, at least 95%, 98%, 99% or 100% sequence identity with SEQ ID NO: 8. These amino acid sequences may also be referred to as being "essentially similar" or "essentially identical" to the FAD3 sequences provided in the sequence listing.

"FAD3-C2 amino acid sequences" or "FAD3-C2 variant amino acid sequences" according to the invention are amino acid sequences having at least 75%, at least 80%, at least 85%, at least 90%, at least 95%, 98%, 99% or 100% sequence identity with SEQ ID NO: 10. These amino acid sequences may also be referred to as being "essentially similar" or "essentially identical" to the FAD3 sequences provided in the sequence listing.

Thus, the invention provides both amino acid sequences of wild type, functional FAD3 proteins, including variants and fragments thereof (as defined further below), as well as mutant amino acid sequences of any of these, whereby the mutation in the amino acid sequence preferably results in a significant reduction in or a complete abolishment of the biological activity of the FAD3 protein as compared to the biological activity of the corresponding wild type FAD3 protein. A significant reduction in or complete abolishment of the biological activity of the FAD3 protein refers herein to a significant reduction in conversion of C18:2 to C18:3, such that the seed oil of a plant expressing the mutant FAD3 protein is has a reduced C18:3 content as compared to a plant expressing the corresponding wild type FAD3 protein.

Both endogenous and isolated amino acid sequences are provided herein. Also provided are fragments of the FAD3 amino acid sequences and FAD3 variant amino acid sequences defined above. A "fragment" of a FAD3 amino acid sequence or variant thereof (as defined) may be of various lengths, such as at least 10, 12, 15, 18, 20, 50, 100, 150, 200, 250, 300, 350 or 370 contiguous amino acids of the FAD3 sequence (or of the variant sequence).

Amino Acid Sequences of Functional FAD3 Proteins

The amino acid sequences depicted in the sequence listing are wild type, functional FAD3 proteins from *Brassica napus*. Thus, these sequences are endogenous to the *Brassica napus* plants from which they were isolated. Other *Brassica* crop species, varieties, breeding lines or wild accessions may be screened for other functional FAD3 proteins with the same amino acid sequences or variants thereof, as described above.

In addition, it is understood that FAD3 amino acid sequences and variants thereof (or fragments of any of these) may be identified in silico, by screening amino acid databases for essentially similar sequences. Fragments of amino acid molecules according to the invention are also provided.

Amino Acid Sequences of Mutant FAD3 Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the FAD3 protein relative to the wild type protein. As described above, basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant FAD3 protein, such as mutations leading to truncated proteins, whereby significant portions of the functional and/or structural amino acid residues or domains, such as the ER retention signal, the eight conserved histidine residues or the signal sequence, are deleted or substituted, as is described above.

Thus in one embodiment, mutant FAD3 proteins are provided comprising one or more deletion or insertion mutations, whereby the deletion(s), insertion(s) or substitutions result(s) in a mutant protein which has significantly reduced or no activity in vivo. Such mutant FAD3 proteins are FAD3 proteins wherein at least 1, at least 2, 3, 4, 5, 10, 20, 30, 50, 100, 150, 200, 250, 300, 350, 370 or more amino acids are deleted, inserted or substituted as compared to the wild type FAD3 protein, whereby the deletion(s) or insertion(s) result(s) in a mutant protein which has significantly reduced or no activity in vivo.

In another embodiment, mutant FAD3 proteins are provided which are truncated whereby the truncation results in a mutant protein that has significantly reduced or no activity in vivo. The truncated protein lacks the amino acids encoded by the coding DNA downstream (3') of the mutation (i.e. the C-terminal part of the FAD3 protein) and maintains the amino acids encoded by the coding DNA upstream (5') of the mutation (i.e. the N-terminal part of the FAD3 protein). In one embodiment, the invention provides a truncated FAD3 protein comprising the N-terminal part of the corresponding wild type FAD3 protein up to but not (fully) including the ER retention motif, i.e. corresponding to anywhere upstream of the lysine residue(s) at position 375 and/or 373 of SEQ ID NO: 2, so that at least lysine 375 and/or lysine 373 are lacking (or corresponding lysine residues in other FAD3 proteins). The more truncated the mutant FAD3 protein is in comparison to the wild type FAD3 protein, the more the truncation may result in a significantly reduced or no activity in vivo of the FAD3 protein In another embodiment, the invention provides a truncated protein of less than about 299, 298 or 295 amino acids (lacking the eighth, seventh, and/or sixth conserved histidines of the third his-box), less than about 131, 130 or 128 amino acids (lacking the fifth, fourth and/or third sixth conserved histidines of the second his-box), less than about 96 or 92 amino acids (lacking the second and/or first sixth conserved histidines of the first his-box) of SEQ ID NO: 2 or homologues residues hereto. In yet another embodiment, the invention provides an N-terminally truncated protein lacking the putative signal sequence.

In yet another embodiment, mutant FAD3 proteins are provided comprising one or more substitution mutations, whereby the substitution(s) result(s) in a mutant protein that has significantly reduced or no activity in vivo. Such mutant FAD3 proteins are FAD3 proteins whereby conserved amino acid residues which have a specific function, such as ER targeting or retention, or iron-binding, are substituted. In one embodiment, a mutant FAD3 protein is provided wherein one or more of amino acids of the ER retention motif, i.e. residues 373-377, especially lysine 373 and/or 375 of SEQ ID NO: 2, or homologues residues hereto, are substituted. Such mutations will lead to a loss of ER localization. Also provided are mutant FAD3 proteins with substitution of one or more of the eight conserved histidine residues, which will result in in a complete loss of protein function. Further, mutant FAD3 proteins are provided with substitution(s) of amino acid(s) in the N-terminal signal sequence. Such substitutions are likely to result in a non-functional FAD3 protein, due to loss of initial ER targeting.

In yet another embodiment, mutant FAD3 proteins are provided comprising one or more insertion or deletion mutations, whereby the insertion(s) and/or deletion(s) result(s) in a mutant protein that has significantly reduced or no activity in vivo. Such mutant FAD3 proteins are FAD3 proteins whereby the positioning between conserved amino acid residues which have a specific function has been altered. In one embodiment, a mutant FAD3 protein is provided wherein one or more of amino acids have been inserted between any of the eight conserved histidines and the putative transmembrane domains. In another embodiment, a mutant FAD3 protein is provided wherein one or more of amino acids have been deleted between any of the eight conserved histidines and the putative transmembrane domains. Such mutations are likely to result in an altered structure and possibly loss of function of the FAD3 protein.

Methods According to the Invention

Mutant FAD3 alleles may be generated (for example induced by mutagenesis) and/or identified using a range of methods, which are conventional in the art, for example using PCR based methods to amplify part or all of the FAD3 genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant FAD3 alleles, using techniques which are conventional in the art, for example polymerase chain reaction (PCR) based techniques (amplification of the FAD3 alleles) or hybridization based techniques, e.g. Southern blot analysis, BAC library screening, and the like, and/or direct sequencing of FAD3 alleles. To screen for the presence of point mutations (so called Single Nucleotide Polymorphisms or SNPs) in mutant FAD3 alleles, SNP detection methods conventional in the art can be used, for example oligoligation-based techniques, single base extension-based techniques, such as pyrosequencing, or techniques based on differences in restriction sites, such as TILLING.

As described above, mutagenization (spontaneous as well as induced) of a specific wild-type FAD3 allele results in the presence of one or more deleted, inserted, or substituted nucleotides (hereinafter called "mutation region") in the resulting mutant FAD3 allele. The mutant FAD3 allele can thus be characterized by the location and the configuration of the one or more deleted, inserted, or substituted nucleotides in the wild type FAD3 allele. The site in the wild type FAD3 allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) FAD3 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) FAD3 allele which is located either immediately upstream of and contiguous with (5' flanking region or sequence") or immediately downstream of and contiguous with (3' flanking region or sequence") the mutation region in the mutant FAD3 allele (or in the corresponding wild type FAD3 allele). A "joining region" as used herein refers to a DNA region in the mutant (or the corresponding wild type) FAD3 allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant FAD3 allele or the plant or plant material comprising a specific mutant FAD3 allele, or products which comprise plant material comprising a specific mutant FAD3 allele are based on the specific genomic characteristics of the specific mutant FAD3 allele as compared to the genomic characteristics of the corresponding wild type FAD3 allele, such as, a specific restriction map of the genomic region comprising the mutation region, molecular markers or the sequence of the flanking and/or mutation regions Once a specific mutant FAD3 allele has been sequenced, primers and probes can be developed which specifically recognize a sequence within the 5' flanking, 3' flanking and/or mutation regions of the mutant FAD3 allele in the nucleic acid (DNA or RNA) of a sample by way of a molecular biological technique. For instance a PCR method can be developed to identify the mutant FAD3 allele in biological samples (such as samples of plants, plant material or products comprising plant material). Such a PCR is based on at least two specific "primers": (1) one recognizing a sequence within the 5' or 3' flanking region of the mutant FAD3 allele and the other recognizing a sequence within the 3' or 5' flanking region of the mutant FAD3 allele, respectively; or (2) one recognizing a sequence within the 5' or 3' flanking region of the mutant FAD3 allele and the other recognizing a sequence within the mutation region of the mutant FAD3 allele; or (3) one recognizing a sequence within the 5' or 3' flanking region of the mutant FAD3 allele and the other recognizing a sequence spanning the joining region between the 3' or 5' flanking region and the mutation region of the specific mutant FAD3 allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant FAD3 allele, so that a specific fragment ("mutant FAD3 specific fragment" or discriminating amplicon) is amplified from a nucleic acid sample comprising the specific mutant FAD3 allele. This means that only the targeted mutant FAD3 allele, and no other sequence in the plant genome, is amplified under optimized PCR conditions.

PCR Primers Suitable for the Invention May Be the Following:

oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant FAD3 allele or the complement thereof (i.e., for example, the sequence 5' or 3' flanking the one or more nucleotides deleted, inserted or substituted in the mutant FAD3 alleles of the invention, such as the sequence 5' or 3' flanking the nonsense, missense, insertion, deletion, frameshift or splice site mutations described above or the complement thereof) (primers recognizing 5' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant FAD3 allele or the complement thereof (i.e., for example, the sequence of nucleotides inserted or substituted in the FAD3 genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant FAD3 alleles of the invention and the sequence of the one or more nucleotides inserted or substituted or the sequence 3' or 5', respectively, flanking the one or more nucleotides deleted, such as the joining region between a sequence 5' or 3' flanking non-sense, missense, insertion, deletion, frameshift or splice site mutations in the FAD3 genes of the invention described above and the sequence of the non-sense, missense or frameshift mutations, or the joining region between a sequence 5' or 3' flanking a potential STOP codon mutation as indicated above or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A⇌T; G⇌C) and reading the sequence in the 5' to 3' direction, i.e. in opposite direction of the represented nucleotide sequence.

Examples of primers suitable to identify specific mutant FAD3 alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant FAD3 allele, provided the mismatches still allow specific identification of the specific mutant FAD3 allele with these primers under optimized PCR conditions. The range of allowable mismatches however, can easily be determined experimentally and are known to a person skilled in the art.

Detection and/or identification of a "mutant FAD3 specific fragment" can occur in various ways, e.g., via size estimation after gel or capillary electrophoresis or via fluorescence-based detection methods. The mutant FAD3 specific fragments may also be directly sequenced. Other sequence specific methods for detection of amplified DNA fragments are also known in the art.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant FAD3 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, MgCl$_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify a mutant FAD3 specific fragment that can be used as a "specific probe" for identifying a specific mutant FAD3 allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant FAD3 allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant FAD3 allele (hereinafter referred to as "mutant FAD3 specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant FAD3 allele.

Specific Probes Suitable for the Invention May Be the Following:
  oligonucleotides ranging in length from 13 nt to about 1000 nt, comprising a nucleotide sequence of at least 13 consecutive nucleotides selected from the 5' or 3' flanking sequence of a specific mutant FAD3 allele or the complement thereof (i.e., for example, the sequence 5' or 3' flanking the one or more nucleotides deleted, inserted or substituted in the mutant FAD3 alleles of the invention, such as the sequence 5' or 3' flanking the nonsense, missense, insertion, deletion, frameshift mutations or splice site described above or the sequence 5' or 3' flanking the nonsense, missense, insertion, deletion or frameshift mutations), or a sequence having at least 80% sequence identity therewith (probes recognizing 5' or 3' flanking sequences); or
  oligonucleotides ranging in length from 13 nt to about 1000 nt, comprising a nucleotide sequence of at least 13 consecutive nucleotides selected from the mutation sequence of a specific mutant FAD3 allele or the complement thereof (i.e., for example, the sequence of nucleotides inserted or substituted in the FAD3 genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant FAD3 alleles of the invention and the sequence of the one or more nucleotides inserted or substituted or the sequence 3' or 5', respectively, flanking the one or more nucleotides deleted, such as the joining region between a sequence 5' or 3' flanking nonsense, missense, insertion, deletion, frameshift or splice site mutations in the FAD3 genes of the invention described above and the sequence of the nonsense, missense, insertion, deletion, frameshift or splice site mutations), provided the mentioned nucleotide sequence is not derived exclusively from either the mutation region or flanking regions.

Examples of specific probes suitable to identify specific mutant FAD3 alleles are described in the Examples.

Detection and/or identification of a "mutant FAD3 specific region" hybridizing to a specific probe can occur in various ways, e.g., via size estimation after gel electrophoresis or via fluorescence-based detection methods. Other sequence specific methods for detection of a "mutant FAD3 specific region" hybridizing to a specific probe are also known in the art.

Alternatively, plants or plant parts comprising one or more mutant FAD3 alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant FAD3 alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in FAD3 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant FAD3 alleles. As for the mutagenesis techniques above, preferably Brassica species are screened which comprise an A and/or a C genome, so that the identified FAD3 allele can subsequently be introduced into other *Brassica* species, such as *Brassica napus*, by crossing (inter- or intraspecific crosses) and selection. In ECOTILLING natural polymorphisms in breeding lines or related species are screened for by the TILLING methodology described above, in which individual or pools of plants are used for PCR amplification of the FAD3 target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally, functionality can be tested as indicated above. Using this approach a plurality of mutant FAD3 alleles (and *Brassica* plants comprising one or more of these) can be identified. The desired mutant alleles can then be combined with the desired wild type alleles by crossing and selection methods as described further below. Finally a single plant comprising the desired number of mutant FAD3 and the desired number of wild type FAD3 alleles is generated.

Oligonucleotides suitable as PCR primers or specific probes for detection of a specific mutant FAD3 allele can also be used to develop methods to determine the zygosity status of the specific mutant FAD3 allele.

To determine the zygosity status of a specific mutant FAD3 allele, a PCR-based assay can be developed to determine the presence of a mutant and/or corresponding wild type FAD3 specific allele:

To determine the zygosity status of a specific mutant FAD3 allele, two primers specifically recognizing the wild-type FAD3 allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type FAD3 allele.

Alternatively, to determine the zygosity status of a specific mutant FAD3 allele, two primers specifically recognizing the wild-type FAD3 allele can be designed in such a way that they are directed towards each other and that one of them specifically recognizes the mutation region. These primers may be primers specifically recognizing the sequence of the 5' or 3' flanking region and the mutation region of the wild type FAD3 allele, respectively. This set of primers, together with a third primer which specifically recognizes the sequence of the mutation region in the mutant FAD3 allele, allow simultaneous diagnostic PCR amplification of the mutant FAD3 gene, as well as of the wild type FAD3 gene.

Alternatively, to determine the zygosity status of a specific mutant FAD3 allele, two primers specifically recognizing the wild-type FAD3 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type FAD3 allele, respectively. This set of primers, together with a third primer which specifically recognizes the joining region between the mutation region and the 3' or 5' flanking region of the mutant FAD3 allele, respectively, allow simultaneous diagnostic PCR amplification of the mutant FAD3 gene, as well as of the wild type FAD3 gene.

Alternatively, the zygosity status of a specific mutant FAD3 allele can be determined by using alternative primer sets that specifically recognize mutant and wild type FAD3 alleles.

If the plant is homozygous for the mutant FAD3 allele or the corresponding wild type FAD3 allele, the diagnostic PCR assays described above will give rise to a single PCR product typical, preferably typical in length, for either the mutant or wild type FAD3 allele. If the plant is heterozygous for the mutant FAD3 allele, two specific PCR products will appear, reflecting both the amplification of the mutant and the wild type FAD3 allele.

Identification of the wild type and mutant FAD3 specific PCR products can occur e.g. by size estimation after gel or capillary electrophoresis (e.g. for mutant FAD3 alleles comprising a number of inserted or deleted nucleotides which results in a size difference between the fragments amplified from the wild type and the mutant FAD3 allele, such that said fragments can be visibly separated on a gel); by evaluating the presence or absence of the two different fragments after gel or capillary electrophoresis, whereby the diagnostic PCR amplification of the mutant FAD3 allele can, optionally, be performed separately from the diagnostic PCR amplification of the wild type FAD3 allele; by direct sequencing of the amplified fragments; or by fluorescence-based detection methods.

Examples of primers suitable to determine the zygosity of specific mutant FAD3 alleles are described in the Examples.

Alternatively, to determine the zygosity status of a specific mutant FAD3 allele, a hybridization-based assay can be developed to determine the presence of a mutant and/or corresponding wild type FAD3 specific allele:

To determine the zygosity status of a specific mutant FAD3 allele, two specific probes recognizing the wild-type FAD3 allele can be designed in such a way that each probe specifically recognizes a sequence within the FAD3 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type FAD3 allele.

Alternatively, to determine the zygosity status of a specific mutant FAD3 allele, two specific probes recognizing the wild-type FAD3 allele can be designed in such a way that one of them specifically recognizes a sequence within the FAD3 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type FAD3 allele, respectively. The use of one or, preferably, both of these probes, optionally, together with a third probe which specifically recognizes the sequence of the mutation region in the mutant FAD3 allele, allow diagnostic hybridization of the mutant and of the wild type FAD3 gene.

Alternatively, to determine the zygosity status of a specific mutant FAD3 allele, a specific probe recognizing the wild-type FAD3 allele can be designed in such a way that the probe specifically recognizes the joining region between the 5' or 3' flanking region, preferably the 5' flanking region, and the mutation region of the wild type FAD3 allele. This probe, optionally, together with a second probe that specifically recognizes the joining region between the 5' or 3' flanking region, preferably the 5' flanking region, and the mutation region of the mutant FAD3 allele, allows diagnostic hybridization of the mutant and of the wild type FAD3 gene.

Alternatively, the zygosity status of a specific mutant FAD3 allele can be determined by using alternative sets of probes that specifically recognize mutant and wild type FAD3 alleles.

If the plant is homozygous for the mutant FAD3 gene or the corresponding wild type FAD3 gene, the diagnostic hybridization assays described above will give rise to a single specific hybridization product, such as one or more hybridizing DNA (restriction) fragments, typical, preferably typical in length, for either the mutant or wild type FAD3 allele. If the plant is heterozygous for the mutant FAD3 allele, two specific hybridization products will appear, reflecting both the hybridization of the mutant and the wild type FAD3 allele.

Identification of the wild type and mutant FAD3 specific hybridization products can occur e.g. by size estimation after gel or capillary electrophoresis (e.g. for mutant FAD3 alleles comprising a number of inserted or deleted nucleotides which results in a size difference between the hybridizing DNA (restriction) fragments from the wild type and the mutant FAD3 allele, such that said fragments can be visibly separated on a gel); by evaluating the presence or absence of the two different specific hybridization products after gel or capillary electrophoresis, whereby the diagnostic hybridization of the mutant FAD3 allele can, optionally, be performed separately from the diagnostic hybridization of the wild type FAD3 allele; by direct sequencing of the hybridizing DNA (restriction) fragments; or by fluorescence-based detection methods.

Examples of probes suitable to determine the zygosity of specific mutant FAD3 alleles are described in the Examples.

Furthermore, detection methods specific for a specific mutant FAD3 allele that differ from PCR- or hybridization-based amplification methods can also be developed using the specific mutant FAD3 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant FAD3 allele in biological samples or the determination of the zygosity status of plant material comprising a specific mutant FAD3 allele. More particularly, a preferred embodiment of the kit of the invention comprises at least two specific primers, as described above, for identification of a specific mutant FAD3 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant FAD3 allele therein, as described above, for identification of a specific mutant FAD3 allele, or at least two or three specific probes for the determination of the zygosity status. Optionally, the kit can further comprise any other reagent (such as but not limited to hybridizing buffer, label) for identification of a specific mutant FAD3 allele in biological samples, using the specific probe.

The kit of the invention can be used, and its components can be specifically adjusted, for purposes of quality control (e.g., purity of seed lots), detection of the presence or absence of a specific mutant FAD3 allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant FAD3 allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific (mutant or wild type) FAD3 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denaturated carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

"Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant FAD3 allele, implying the presence of nucleic acids in the samples. Thus the methods referred to herein for identifying a specific mutant FAD3 allele in biological samples, relate to the identification in biological samples of nucleic acids that comprise the specific mutant FAD3 allele.

The present invention also relates to the combination of specific FAD3 alleles in one plant, to the transfer of one or more specific mutant FAD3 allele(s) from one plant to another plant, to the plants comprising one or more specific mutant FAD3 allele(s), the progeny obtained from these plants and to plant cells, plant parts, and plant seeds derived from these plants.

Thus, in one embodiment of the invention a method for combining two or more selected mutant FAD3 alleles in one plant is provided comprising the steps of:
  a. generating and/or identifying two or more plants each comprising one or more selected mutant FAD3 alleles, as described above,
  b. crossing a first plant comprising one or more selected mutant FAD3 alleles with a second plant comprising one or more other selected mutant FAD3 alleles, collecting F1 seeds from the cross, and, optionally, identifying an F1 plant comprising one or more selected mutant FAD3 alleles from the first plant with one or more selected mutant FAD3 alleles from the second plant, as described above,
  c. optionally, repeating step (b) until an F1 plant comprising all selected mutant FAD3 alleles is obtained,
  d. optionally,
     identifying an F1 plant, which is homozygous or heterozygous for a selected mutant FAD3 allele by determining the zygosity status of the mutant FAD3 alleles, as described above, or
     generating plants which are homozygous for one or more of the selected mutant FAD3 alleles by performing one of the following steps:
        extracting doubled haploid plants from treated microspore or pollen cells of F1 plants comprising the one or more selected mutant FAD3 alleles, as described above,
        selfing the F1 plants comprising the one or more selected mutant FAD3 allele(s) for one or more generations (y), collecting F1 Sy seeds from the selfings, and identifying F1 Sy plants, which are homozygous for the one or more mutant FAD3 allele, as described above.

In another embodiment of the invention a method for transferring one or more mutant FAD3 alleles from one plant to another plant is provided comprising the steps of:
  a. generating and/or identifying a first plant comprising one or more selected mutant FAD3 alleles, as described above, or generating the first plant by combining the one or more selected mutant FAD3 alleles in one plant, as described above (wherein the first plant is homozygous or heterozygous for the one or more mutant FAD3 alleles)
  b. crossing the first plant comprising the one or more mutant FAD3 alleles with a second plant not comprising the one or more mutant FAD3 alleles, collecting F1 seeds from the cross (wherein the seeds are heterozygous for a mutant FAD3 allele if the first plant was homozygous for that mutant FAD3 allele, and wherein half of the seeds are heterozygous and half of the seeds are azygous for, i.e. do not comprise, a mutant FAD3 allele if the first plant was heterozygous for that mutant FAD3 allele), and, optionally, identifying F1 plants comprising one or more selected mutant FAD3 alleles, as described above,
  c. backcrossing F1 plants comprising one or more selected mutant FAD3 alleles with the second plant not comprising the one or more selected mutant FAD3 alleles for one or more generations (x), collecting BCx seeds from the crosses, and identifying in every generation BCx plants comprising the one or more selected mutant FAD3 alleles, as described above,
  d. optionally, generating BCx plants which are homozygous for the one or more selected mutant FAD3 alleles by performing one of the following steps:
     extracting doubled haploid plants from treated microspore or pollen cells of BCx plants comprising the one or more desired mutant FAD3 allele(s), as described above
     selfing the BCx plants comprising the one or more desired mutant FAD3 allele(s) for one or more generations (y), collecting BCx Sy seeds from the selfings, and identifying BCx Sy plants, which are homozygous for the one or more desired mutant FAD3 allele, as described above.

In one aspect of the invention, the first and the second plant are Brassicaceae plants, particularly *Brassica* plants, especially *Brassica napus* plants or plants from another *Brassica* crop species. In another aspect of the invention, the first plant is a Brassicaceae plant, particularly a *Brassica* plant, especially a *Brassica napus* plant or a plant from another *Brassica* crop species, and the second plant is a plant from a Brassicaceae breeding line, particularly from a *Brassica* breeding line, especially from a *Brassica napus* breeding line or from a breeding line from another *Brassica* crop species. "Breeding line", as used herein, is a preferably homozygous plant line distinguishable from other plant lines by a preferred genotype and/or phenotype that is used to produce hybrid offspring.

In yet another embodiment of the invention, a method for making a plant, in particular a *Brassica* crop plant, such as a *Brassica napus* plant, of which the seed oil has a significantly reduced C18:3 content, but which preferably maintains an agronomically suitable development, is provided comprising combining and/or transferring mutant FAD3 alleles according to the invention in or to one *Brassica* plant, as described above.

In one aspect of the invention, the plant is a *Brassica* plant comprising at least two mutant FAD3 genes wherein the seed oil has a significantly reduced C18:3 content, but which preferably maintains an agronomically suitable development, by combining and/or transferring at least two mutant FAD3 alleles according to the invention in or to the *Brassica* plant, as described above.

The invention also relates to the use of a plant, in particular a *Brassica* crop plant, such as a *Brassica napus* plant, comprising one or more of the mutant FAD3 alleles of the invention for combining and/or transferring mutant FAD3 alleles according to the invention in or to one *Brassica* plant, as described above.

In yet another embodiment, the invention relates to the use of a mutant FAD3 allele of the invention to reduce the C18:3 content in the seed oil of a *Brassica* plant In another aspect of the invention the use of the plants and seeds of the invention to produce oilseed rape oil is provided.

In a further embodiment, the invention provides the use of the plants of the invention to produce seed comprising mutant FAD3 alleles or to produce a crop of oilseed rape comprising mutant FAD3 proteins.

SEQUENCES

SEQ ID NO: 1: Genomic DNA of the FAD3-A1 gene from *Brassica napus*.
SEQ ID NO: 2: Amino acid sequence of the FAD3-A1 protein from *Brassica napus*
SEQ ID NO: 3: Genomic DNA of the FAD3-C1 gene from *Brassica napus*
SEQ ID NO: 4: Amino acid sequence of the FAD3-A2 protein from *Brassica napus*
SEQ ID NO: 5: Genomic DNA of the FAD3-A2 gene from *Brassica napus*
SEQ ID NO: 6: Amino acid sequence of the FAD3-A2 protein from *Brassica napus*
SEQ ID NO: 7: Genomic DNA of the FAD3-A3 gene from *Brassica napus*
SEQ ID NO: 8: Amino acid sequence of the FAD3-A3 protein from *Brassica napus*
SEQ ID NO: 9: Genomic DNA of the FAD3-C2 gene from *Brassica napus*
SEQ ID NO: 10: Amino acid sequence of the FAD3-C2 protein from *Brassica napus*
SEQ ID NO: 11: Coding region of the FAD3-A1 gene from *Brassica napus*
SEQ ID NO: 12: Coding region of the FAD3-C1 gene from *Brassica napus*
SEQ ID NO: 13: Coding region of the FAD3-A2 gene from *Brassica napus*
SEQ ID NO: 14: Coding region of the FAD3-A3 gene from *Brassica napus*
SEQ ID NO: 15: Coding region of the FAD3-C2 gene from *Brassica napus*
SEQ ID NO: 16: *Arabidopsis* FAD3 forward PCR primer
SEQ ID NO: 17: *Arabidopsis* FAD3 reverse PCR primer
SEQ ID NO: 18: LOLI105 FAM probe
SEQ ID NO: 19: LOLI105 VIC probe
SEQ ID NO: 20: LOLI105 Fw primer
SEQ ID NO: 21: LOLI105 Rw primer
SEQ ID NO: 22: LOLI103 FAM probe
SEQ ID NO: 23: LOLI103 VIC probe
SEQ ID NO: 24: LOLI103 Fw primer
SEQ ID NO: 25: LOLI103 Rw primer
SEQ ID NO: 26: LOLI108 FAM probe
SEQ ID NO: 27: LOLI108 VIC probe
SEQ ID NO: 28: LOLI108 Fw primer
SEQ ID NO: 29: LOLI108 Rw primer
SEQ ID NO: 30: LOLI111 FAM probe
SEQ ID NO: 31: LOLI111 VIC probe
SEQ ID NO: 32: LOLI111 Fw primer
SEQ ID NO: 33: LOLI111 Rw primer
SEQ ID NO: 34: LOLI115 FAM probe
SEQ ID NO: 35: LOLI115 VIC probe
SEQ ID NO: 36: LOLI115 Fw primer
SEQ ID NO: 37: LOLI115 Rw primer

EXAMPLES

All examples were essentially carried out as described in WO09/007091, which is incorporated herein by reference in its entirety.

Example 1—Determination of Number of FAD3 Genes in *Brassica Napus* and Isolation of the DNA Sequences of the FAD3 Genes A Bacterial Artificial Chromosome (BAC) library of a *Brassica napus* research spring OSR line was screened using a probe that was amplified from *Arabidopsis* genomic DNA with primers with SEQ ID NO: 16 and SEQ ID NO: 17 according to standard molecular biological techniques and BAC clones hybridizing to the probe were isolated (hereinafter called "positive colonies").

Southern blot analysis was performed using the same probe as above according to standard molecular biological techniques on BAC clone DNA isolated from the positive colonies and on genomic DNA isolated from *B. napus* (AC), *Brassica rapa* (AA) and *Brassica oleracea* (CC). Based on a comparison between the hybridization patterns obtained after digestion of BAC clone DNA of the identified positive colonies and of genomic DNA isolated from *B. napus, B. rapa* and *B. oleracea*, the BAC clones were grouped in 5 groups, of which three could be mapped to the A genome and two to the C genome. For each of the 5 groups a BAC clone was selected.

Example 2—Characterization of FAD3 Gene Sequences from *Brassica Napus*

The entire DNA sequences of the BAC clones of the selected positive colonies were determined by 454 sequencing, after which the FAD3 sequences were identified by blast analysis (Blast2seq) using the *Arabidopsis thaliana* FAD3 gene (genbank accession number D26508) as query sequence.

The intron-exon structures of the FAD3 sequences were determined with FgeneSH (Softberry, Inc. Mount Kisco, N.Y., USA) and by optimal alignment of the gene sequence with the *A. thaliana* coding sequence (genbank accession number NM_128552). The protein encoding regions of the FAD3 genes as well as the FAD3 amino acid sequences encoded by these nucleic acid sequences are represented in the sequence listing. Of the FAD3 genes mapping to the A-genome, the sequence of the FAD3 gene mapping to N04 was found to correspond to FAD3-A gene (genbank accession number L22962) and was designated FAD3-A1, while the sequences mapping to N05 and NO3 were designated FAD3-A2 and FAD3-A3 respectively. Of the FAD3 genes mapping on C genome, one of the sequences was found to correspond to a FAD3-C gene (described in WO04/072259) and was designated FAD3-C1, while the other was found to be homologous to FAD3-A2 and was designated FAD3-C2. These designations are used throughout the specification. The genomic sequences of the FAD3 genes are represented in the sequence listing.

Example 3—Expression of *Brassica* FAD3 Genes

The relative and absolute expression levels of the various FAD3 genes in developing embryo's from *B. napus* were determined by whole transcriptome sequencing of cDNAs using the Roche 454 GS FLX Titanium technology (http://www.454.com/products-solutions/how-it-works/index.asp). For the production of cDNA total RNA was extracted using TRIZOL reagent (Invitrogen). This was done in triplicate for every embryo developmental stage. Subsequently, total RNA samples derived from embryos of the same developmental stage were pooled and mRNA was purified from the total RNA samples with the GE Healthcare mRNA Purification Kit. In the next step, cDNA was prepared using the SuperScript Double-Stranded cDNA Synthesis Kit (Invitrogen). Then, cDNA was size fractionated using CHROMA Spin-400 columns according to the protocol described in the SMART cDNA Library Construction Kit (Clontech). Following cDNA sequence analysis transcript quantification was done by read counting of target sequences. Expression of each FAD3 gene was normalized for the number of sequences in each time-point dataset.

TABLE 1

Normalized (norm) FAD3 expression and percentage (%) of total FAD3 expression in embryos of *Brassica napus* 14-35 days after flowering (DAF).

|  | 14-20 DAF | | 21-25 DAF | | 26-30 DAF | | 31-35 DAF | |
| --- | --- | --- | --- | --- | --- | --- | --- | --- |
|  | norm | % | norm | % | norm | % | norm | % |
| FAD3-A1 | 210.0 | 38.9% | 213.9 | 39.8% | 150.5 | 42.6% | 22.8 | 26.9% |
| FAD3-C1 | 227.0 | 42.0% | 226.9 | 42.2% | 148.8 | 42.2% | 43.3 | 50.9% |
| FAD3-A2 | 35.0 | 6.5% | 36.7 | 6.8% | 11.6 | 3.3% | 6.3 | 7.4% |
| FAD3-A3 | 32.0 | 5.9% | 38.9 | 7.2% | 30.6 | 8.7% | 9.5 | 11.1% |
| FAD3-C2 | 36.0 | 6.7% | 21.6 | 4.0% | 11.6 | 3.3% | 3.2 | 3.7% |
| tot | 540.0 | 100.0% | 538.0 | 100.0% | 353.0 | 100.0% | 85.1 | 100.0% |

From table 1 it is clear that the total FAD3 expression diminishes over time. FAD3-A1 and FAD3-C1 constitute the larger part of the total FAD3 mRNA expression, both around 40%. This is followed by FAD3-A3, FAD-A2 and FAD-C2, comprising at most 11.1%, 7.4% and 6.7% of the total FAD3 expression, respectively.

Example 4—Generation and Isolation of Mutant *Brassica* FAD3 Alleles

Mutations in the FAD3 genes identified in Example 1 were generated and identified as follows:
- 30,000 seeds from an elite spring oilseed rape breeding line (M0 seeds) were preimbibed for two hours on wet filter paper in deionized or distilled water. Half of the seeds were exposed to 0.8% EMS and half to 1% EMS (Sigma: M0880) and incubated for 4 hours.
- The mutagenized seeds (M1 seeds) were rinsed 3 times and dried in a fume hood overnight. 30,000 M1 plants were grown in soil and selfed to generate M2 seeds. M2 seeds were harvested for each individual M1 plant.
- Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).
- The DNA samples were screened for the presence of point mutations in the FAD3 genes causing the introduction of STOP codons in the protein-encoding regions of the FAD3 genes or the disruption of splice sites in the FAD3 mRNA, by direct sequencing by standard sequencing techniques (Agowa) and analyzing the sequences for the presence of the point mutations using the NovoSNP software (VIB Antwerp).

The following mutant FAD3 alleles were thus identified:

TABLE 2

Mutations in FAD3 genes

| Allele | Nucleotide position | | Wild type codon | Mutant codon | Amino acid sequence and position | Mutation type |
| --- | --- | --- | --- | --- | --- | --- |
|  | Genomic sequence | Coding sequence |  |  |  |  |
| FAD3-A1 LOLI105 | SEQ ID: 1 2405 | SEQ ID: 11 732 | TGG | TGA | SEQ ID: 2 244 | Trp→Stop |
| FAD3-C1 LOLI103 [1] | SEQ ID: 3 2702 | SEQ ID: 12 543 | TGG | TGA | SEQ ID: 4 181 | Trp→Stop |
| FAD3-A2 LOLI108 [2] | SEQ ID: 5 3934 | SEQ ID: 13 749 | TGG | TAG | SEQ ID: 6 250 | Trp→Stop |
| FAD3-A3 LOLI111 [3] | SEQ ID: 7 2847 | SEQ ID: 14 552 | TGG | TGA | SEQ ID: 8 184 | Trp→Stop |
| FAD3-C2 LOLI115 [2] | SEQ ID: 9 3909 | SEQ ID: 15 551 | TGG | TAG | SEQ ID: 10 184 | Trp→Stop |

(1) Seeds comprising FAD3-A1-LOLI105 and FAD3-C1-LOLI103 (designated 09MBBN001740) have been deposited at the NCIMB Limited (Ferguson Building, Craibstone Estate, Bucksburn, Aberdeen, Scotland, AB21 9YA, UK) on Oct. 9, 2009, under accession number NCIMB 41655.
(2) Seeds comprising FAD3-A2-LOLI108 and FAD3-C2-LOLI115 (designated 09MBBN001742) have been deposited at the NCIMB Limited (Ferguson Building, Craibstone Estate, Bucksburn, Aberdeen, Scotland, AB21 9YA, UK) on Oct. 9, 2009, under accession number NCIMB 41656.
(3) Seeds comprising FAD3-A3-LOLI111 (designated 09MBBN000519) have been deposited at the NCIMB Limited (Ferguson Building, Craibstone Estate, Bucksburn, Aberdeen, Scotland, AB21 9YA, UK) on Oct. 9, 2009, under accession number NCIMB 41657.

Access to these deposits will be available during the pendency of the application to the Commissioner of Patents and Trademarks and persons determined by the Commissioner to be entitled thereto upon request. The deposits will be maintained for a period of 30 years, or 5 years after the most recent request, or for the enforceable life of the patent, whichever is longer, and will be replaced if it becomes nonviable during that period.

In conclusion, the above examples show how mutant FAD3 alleles can be generated and isolated. Also, plant material comprising such mutant alleles can be used to combine selected mutant and/or wild type alleles in a plant, as described in the following examples.

Example 5—Identification of a *Brassica* Plant Comprising a Mutant *Brassica* FAD3 Allele

*Brassica* plants comprising the mutations in the FAD3 genes identified in Example 4 were identified as follows:
For each mutant FAD3 allele identified in the DNA sample of an M2 plant, at least 48 M2 plants derived from the same M1 plant as the M2 plant comprising the FAD3 mutation were grown and DNA samples were prepared from leaf samples of each individual M2 plant.
The DNA samples were screened for the presence of the identified point FAD3 mutation as described above in Example 4.
Heterozygous and homozygous (as determined based on the electropherograms) M2 plants comprising the same mutation were selfed and M3 seeds were harvested.

Example 6—Analysis of the Fatty Acid Composition of the Seed Oil of *Brassica* Plants Comprising One to Three Mutant *Brassica* FAD3 Genes in Elite *Brassica* Lines The correlation between the presence of multiple mutant FAD3 alleles in a *Brassica* plant grown in the greenhouse and the fatty acid composition of the seed oil of the *Brassica* plant was determined as follows. Of the *Brassica* plants identified in Example 5 (F1S2), plants comprising a mutant allele of each of the FAD3 genes (LOLI105, LOLI103, LOLI108, LOLI115 and LOLI111) were first crossed with an elite male and an elite female *Brassica* breeding line, and the progeny plants comprising the mutation were subsequently selfed to obtain homozygous plants. For comparison, the same crossings were performed with plants comprising mutant FAD-A1 and FAD-C1 alleles as described in WO01/25453 and WO04/072259, respectively. Subsequently, the fatty acid composition of the seed oil of individual progeny *Brassica* plants homozygous for the mutant FAD3 allele(s) was determined by extracting the fatty acyls from the seeds and analyzing their relative levels in the seed oil by capillary gas-liquid chromatography as described in WO09/007091. Table 3 displays the percentage C18:3 of the total oil content of at least 0.2 g of mature seed of the F1S2×elite crosses of *Brassica* plants grown in the greenhouse.

TABLE 3

Average (Av) and standard deviation (SD) of C18:3 seed oil content percentage (%) in elite male and female crosses.

| allele FAD3A1/FAD3C1/FAD3A2/FAD3A3/FAD3C2 | Female | | Male | |
|---|---|---|---|---|
| | Av C18:3 | SD C18:3 | Av C18:3 | SD C18:3 |
| LOLI103 | | | | |
| FAD3A1/FAD3C1/W-TYPE/W-TYPE/W-TYPE | 3.59 | 0.32 | 3.97 | 0.38 |
| FAD3A1/LOLI103/W-TYPE/W-TYPE/W-TYPE | 3.90 | 0.30 | 3.97 | 0.63 |
| WTYPE/FAD3C1/W-TYPE/W-TYPE/W-TYPE | 5.89 | 0.51 | 5.99 | 0.53 |
| WTYPE/LOLI103/W-TYPE/W-TYPE/W-TYPE | 6.37 | 0.74 | 6.15 | 0.67 |
| LOLI105 | | | | |
| FAD3A1/FAD3C1/W-TYPE/W-TYPE/W-TYPE | 3.82 | 0.74 | 3.69 | 0.88 |
| LOLI105/FAD3C1/W-TYPE/W-TYPE/W-TYPE | 3.68 | 0.42 | 4.35 | 1.54 |
| FAD3A1/W-TYPE/W-TYPE/W-TYPE/W-TYPE | 5.81 | 0.46 | 5.78 | 0.85 |
| LOLI105/W-TYPE/W-TYPE/W-TYPE/W-TYPE | 6.24 | 0.50 | 5.98 | 0.87 |
| LOLI108 | | | | |
| FAD3A1/FAD3C1/W-TYPE/W-TYPE/W-TYPE | 3.42 | 0.11 | 2.84 | 0.12 |
| FAD3A1/FAD3C1/LOLI108/W-TYPE/W-TYPE | 2.62 | 0.08 | 2.96 | 0.31 |
| FAD3A1/W-TYPE/W-TYPE/W-TYPE/W-TYPE | 5.89 | 0.83 | 5.55 | 0.67 |
| FAD3A1/W-TYPE/LOLI108/W-TYPE/W-TYPE | 4.83 | 0.32 | 4.93 | 0.26 |
| W-TYPE/FAD3C1/W-TYPE/W-TYPE/W-TYPE | 5.48 | 0.32 | 5.04 | 0.23 |
| W-TYPE/FAD3C1/LOLI108/W-TYPE/W-TYPE | 4.31 | 0.37 | 4.36 | 1.06 |
| W-TYPE/W-TYPE/W-TYPE/W-TYPE/W-TYPE | 6.54 | 0.55 | 7.20 | 0.92 |
| W-TYPE/W-TYPE/LOLI108/W-TYPE/W-TYPE | 6.51 | 0.19 | 5.92 | 0.63 |

TABLE 3-continued

Average (Av) and standard deviation (SD) of C18:3 seed oil content percentage (%) in elite male and female crosses.

| allele<br>FAD3A1/FAD3C1/FAD3A2/FAD3A3/FAD3C2 | Female | | Male | |
|---|---|---|---|---|
| | Av C18:3 | SD C18:3 | Av C18:3 | SD C18:3 |
| LOLI111 | | | | |
| FAD3A1/FAD3C1/W-TYPE/W-TYPE/W-TYPE | 3.77 | 0.23 | 3.42 | 0.78 |
| FAD3A1/FAD3C1/W-TYPE/LOLI111/W-TYPE | 2.58 | 0.17 | 2.43 | 0.55 |
| FAD3A1/W-TYPE/W-TYPE/W-TYPE/W-TYPE | 6.12 | 0.24 | 4.71 | 0.83 |
| FAD3A1/W-TYPE/W-TYPE/LOLI111/W-TYPE | 4.43 | 0.18 | 3.53 | 0.62 |
| W-TYPE/FAD3C1/W-TYPE/W-TYPE/W-TYPE | 5.60 | 0.85 | 5.01 | 0.96 |
| W-TYPE/FAD3C1/W-TYPE/LOLI111/W-TYPE | 4.59 | 0.24 | 4.17 | 0.16 |
| W-TYPE/W-TYPE/W-TYPE/W-TYPE/W-TYPE | 6.90 | 2.02 | 7.43 | 0.63 |
| W-TYPE/W-TYPE/W-TYPE/LOLI111/W-TYPE | 6.68 | 0.40 | 7.06 | 1.02 |
| LOLI115 | | | | |
| FAD3A1/FAD3C1/W-TYPE/W-TYPE/W-TYPE | 4.02 | 0.24 | 3.44 | 0.49 |
| FAD3A1/FAD3C1/W-TYPE/W-TYPE/LOLI115 | — | — | 3.20 | 0.13 |
| FAD3A1/W-TYPE/W-TYPE/W-TYPE/W-TYPE | 5.17 | ND | — | — |
| FAD3A1/W-TYPE/W-TYPE/W-TYPE/LOLI115 | 6.06 | 0.55 | 4.33 | 0.08 |
| W-TYPE/FAD3C1/W-TYPE/W-TYPE/W-TYPE | 4.35 | 0.58 | 4.71 | 1.22 |
| W-TYPE/FAD3C1/W-TYPE/W-TYPE/LOLI115 | 3.29 | ND | — | — |
| W-TYPE/W-TYPE/W-TYPE/W-TYPE/W-TYPE | 5.93 | 0.69 | 5.86 | 0.79 |
| W-TYPE/W-TYPE/W-TYPE/W-TYPE/LOLI115 | 6.49 | 0.99 | — | — |

ND: could not be determined.

First, plants comprising the FAD3-A1 and FAD3-C1 mutant alleles as described in WO01/25453 and WO04/072259 were compared with plants comprising the LOLI105 (FAD3-A1) and LOLI103 (FAD3-C1) mutant alleles, respectively, for their seed oil composition. Plants homozygous for the LOLI103 allele displayed a similar reduction in C18:3 seed oil content when compared to wild type plants (i.e. not comprising any mutant FAD3 allele) as plants homozygous for the FAD3-A1 allele. Likewise, plants homozygous for the LOLI105 allele displayed a similar reduction in C18:3 seed oil content when compared to wild type plants as plants homozygous for the FAD3-C1 allele.

Next, the seed oil composition of plants comprising the mutant FAD3 alleles LOLI108 (FAD3-A2), LOLI111 (FAD3-A3) or LOLI115 (FAD3-C2) was compared to that of wild type plants and plants comprising the FAD3-A1 and/or FAD3-C1 mutant alleles of WO01/25453 and WO04/072259. The wild type plants (i.e. not comprising any mutant FAD3 allele) displayed a C18:3 seed oil content of about 7%. In seed oil of plants comprising the FAD3-A1 or FAD3-C1 mutant alleles in homozygous state, a reduction of C18:3 seed oil content of about 1-2% was observed. Plants comprising both the FAD3-A1 and FAD3-C1 mutant alleles of WO01/25453 and WO04/072259 in homozygous state showed a reduction in C18:3 seed oil seed content of at most 4%. Plants comprising mutant alleles LOLI108, LOLI111 or LOLI115 in homozygous state did not show a significant reduction in C18:3 in seed oil when compared to seed oil from wild type plants. Surprisingly however, the LOLI108 and LOLI111 alleles did have an additional effect on the C18:3 reduction in seed oil by the FAD3-A1 and/or FAD3-C1 mutant alleles. Particularly in progeny plants from crosses with the elite female line, homozygosity for LOLI108 allele was found to further reduce the C18:3 seed oil content of plants homozygous for the FAD3-C1 mutant allele alone or of plants homozygous for both the FAD3-A1 and FAD3-C1 mutant alleles, leading to a total C18:3 seed oil content in the triple homozygous mutant of below 3%. A similar effect was observed for the LOLI111 allele in combination with the FAD3-A1 mutant allele alone or in combination with both FAD3-A1 and FAD3-C1 mutant alleles, again resulting in a reduction of the C18:3 seed oil content in the triple homozygous mutant to below 3%. In the male elite line a similar trend was observed. Similar to LOLI108 and LOLI111, homozygosity for the LOLI115 allele alone did not have an effect C18:3 seed oil content when compared to wild type plants, but could sometimes further reduce the C18:3 seed oil content of plants already comprising the FAD3-A1 and/or FAD3-C1 mutant alleles.

In conclusion, these data show that, although the FAD3-A2, FAD3-A3 and FAD3-C2 genes only contribute to a small fraction of the total FAD3 expression in the developing seed and mutations in these genes alone did not alter C18:3 content in seed oil in elite crosses, in combination with mutations in the FAD3-A1 and FAD3-C1 genes a reduction of C18:3 to about below 3% could be achieved when plants were grown in the greenhouse.

In a similar experiment, oil composition of plants comprising the mutant FAD3 alleles LOLI108 (FAD3-A2), LOLI111 (FAD3-A3) or LOLI115 (FAD3-C2) in a background comprising the FAD3-A1 and/or FAD3-C1 mutant alleles of WO01/25453 and WO04/072259 was determined after two backcrossings with elite male or female breeding lines. The progeny plants comprising the mutation were subsequently selfed to obtain homozygous plants, and oil composition in seeds of these plants upon a second selfing (BC2S2) were analyzed as described above. Table 4 displays the percentage C18:3 of the total oil content.

TABLE 4

Average (Av) and standard deviation (SD) of C18:3 seed oil content percentage (%) in elite male and female crosses.

| | Female | | Male | |
|---|---|---|---|---|
| allele FAD3A1/FAD3C1/FAD3A2/FAD3A3/FAD3C2 | Av C18:3 | SD C18:3 | Av C18:3 | SD C18:3 |
| LOLI108 | | | | |
| FAD3A1/FAD3C1/W-TYPE/W-TYPE/W-TYPE | 3.76 | 0.13 | 3.68 | 0.09 |
| FAD3A1/FAD3C1/LOLI108/W-TYPE/W-TYPE | 2.99 | 0.07 | 3.89 | 0.03 |
| LOLI111 | | | | |
| FAD3A1/FAD3C1/W-TYPE/W-TYPE/W-TYPE | 3.88 | 0.09 | 3.79 | 0.08 |
| FAD3A1/FAD3C1/W-TYPE/LOLI111/W-TYPE | 2.70 | 0.04 | 2.33 | 0.05 |
| LOLI115 | | | | |
| FAD3A1/FAD3C1/W-TYPE/W-TYPE/W-TYPE | 3.86 | 0.10 | 3.09 | 0.06 |
| FAD3A1/FAD3C1/W-TYPE/W-TYPE/LOLI115 | 2.98 | 0.05 | 4.26 | 0.09 |

These data confirm that, although the FAD3-A2, FAD3-A3 and FAD3-C2 genes only contribute to a small fraction of the total FAD3 expression in the developing seed and mutations in these genes alone did not alter C18:3 content in seed oil in elite crosses, in combination with mutations in the FAD3-A1 and FAD3-C1 genes a reduction of C18:3 to about below 3% could be achieved when plants were grown in the greenhouse.

Example 7—Analysis of the Fatty Acid Composition of the Seed Oil of *Brassica* Plants Comprising One to Four Mutant *Brassica* FAD3 Genes in Elite *Brassica* Lines Grown in the Greenhouse The effect of more than three mutant FAD3 alleles on fatty acid composition of the seed oil of *Brassica* plants was determined in the greenhouse. Of the *Brassica* plants identified in Example 5 (F1S2), plants comprising a mutant allele of each of the FAD3 genes (LOLI105, LOLI103, LOLI108, LOLI115 and LOLI111) were selfed to obtain homozygous plants. Further crosses between the lines containing the mutant FAD3 alleles were made to obtain plants with more than one mutant FAD3 gene. Subsequently, the fatty acid composition of the seed oil of individual progeny *Brassica* plants (nonBC) homozygous for the mutant FAD3 allele(s) was determined as described above. Table 5 shows the percentace C18:3 of the total oil of the *Brassica* plants in the greenhouse.

TABLE 5

Average (Av) and standard deviation (SD) of C18:3 seed oil content percentage (%) from *Brassica* plants grown in the greenhouse

| allele FAD3A1/FAD3A2/FAD3A3/FAD3C1/FAD3C2 | Av C18:3 | SD C18:3 |
|---|---|---|
| W-TYPE/W-TYPE/W-TYPE/W-TYPE/W-TYPE | 9.08 | 0.11 |
| Single mutants | | |
| LOLI105/W-TYPE/W-TYPE/W-TYPE/W-TYPE | 7.33 | 0.20 |
| W-TYPE/LOLI108/W-TYPE/W-TYPE/W-TYPE | 9.10 | 0.09 |
| W-TYPE/W-TYPE/W-TYPE/LOLI103/W-TYPE | 7.67 | 0.15 |
| W-TYPE/W-TYPE/W-TYPE/W-TYPE/LOLI115 | 9.25 | 0.30 |
| Double mutants | | |
| LOLI105/LOLI108/W-TYPE/W-TYPE/W-TYPE | 6.45 | 0.09 |
| LOLI105/W-TYPE/W-TYPE/LOLI103/W-TYPE | 4.57 | 0.05 |
| LOLI105/W-TYPE/W-TYPE/W-TYPE/LOLI115 | 6.17 | 0.06 |
| W-TYPE/LOLI108/W-TYPE/LOLI103/W-TYPE | 6.92 | 0.08 |
| W-TYPE/LOLI108/W-TYPE/W-TYPE/LOLI115 | 8.26 | 0.10 |
| Triple mutants | | |
| LOLI105/LOLI108/W-TYPE/LOLI103/W-TYPE | 3.39 | 0.05 |
| LOLI105/LOLI108/W-TYPE/W-TYPE/LOLI115 | 5.52 | 0.09 |
| W-TYPE/LOLI108/W-TYPE/LOLI103/LOLI115 | 5.27 | 0.03 |
| Quadruple mutant | | |
| LOLI105/LOLI108/W-TYPE/LOLI103/LOLI115 | 2.36 | 0.07 |

From the experiment with the single mutants, it can be concluded that only FAD3A1 and in FAD3C1 mutant alleles cause a significant reduction of C18:3 seed oil content. As also observed in the previous experiment, FAD3A2, FAD3A3 and FAD3C2 mutants do further reduce C18:3 seed oil content in a genetic background already containing either mutant FAD3A1, or mutant FAD3C1, or both. In addition, it is consistently observed that, in the double and triple mutants, lines comprising both the FAD3A1 and FAD3C1 mutant alleles contain a significantly lower C18:3 seed oil content than the other lines containing the same number of mutant FAD3 genes. Moreover, there seems to be a trend towards the more mutant FAD3 alleles present, the lower the C18:3 content in the seed oil.

Example 8—Analysis of the Effect of Stacking Multiple Mutant FAD3 Genes on Fatty Acid Composition in *Brassica* Plants Grown in the Greenhouse Next, it was investigated to what extent stacking of mutant alleles of different FAD3 genes, on top of the FAD3A1 and FAD3C1 mutant alleles, had an effect on fatty acid composition in *Brassica* grown in the greenhouse. To this end, the lines containing the LOLI108, LOLI111 and LOLI115 mutations were backcrossed twice or three times with elite male and female lines comprising the FAD3-A1 and/or FAD3-C1 mutant alleles of WO01/25453 and WO04/072259. The progeny plants comprising the mutant alleles were subsequently selfed to obtain homozygous plants. Further crosses between the lines containing the mutant alleles of FAD3 genes that had been backcrossed twice were made to obtain plants with mutant alleles of multiple FAD3 genes. Oil composition in seeds of these plants upon a second selfing (BC2S2 for the quadruple mutants and BC3S2 for the triple mutants) were analyzed as described above. Table 6 displays the percentage C18:3 of the total oil content.

TABLE 6

Average (Av) and standard deviation (SD) of C18:3 seed oil content percentage (%) in elite male and female crosses upon stacking the different FAD3 mutant alleles on top of the mutant FAD3A1 and FAD3C1 alleles.

| allele<br>FAD3A1/FAD3C1/FAD3A2/FAD3A3/FAD3C2 | Female | | Male | |
|---|---|---|---|---|
| | Av<br>C18:3 | SD<br>C18:3 | Av<br>C18:3 | SD<br>C18:3 |
| LOLI108 | | | | |
| FAD3A1/FAD3C1/W-TYPE/W-TYPE/W-TYPE | 2.56 | 0.07 | 2.18 | 0.05 |
| FAD3A1/FAD3C1/LOLI108/W-TYPE/W-TYPE | 2.02 | 0.04 | 2.09 | 0.03 |
| LOLI111 | | | | |
| FAD3A1/FAD3C1/W-TYPE/W-TYPE/W-TYPE | 2.70 | 0.08 | 2.29 | 0.03 |
| FAD3A1/FAD3C1/W-TYPE/LOLI111/W-TYPE | 2.24 | 0.04 | 1.56 | 0.02 |
| LOLI115 | | | | |
| FAD3A1/FAD3C1/W-TYPE/W-TYPE/W-TYPE | 2.49 | 0.06 | 2.47 | 0.07 |
| FAD3A1/FAD3C1/W-TYPE/W-TYPE/LOLI115 | 2.05 | 0.08 | 1.92 | 0.04 |
| LOLI108/LOLI111 | | | | |
| FAD3A1/FAD3C1/W-TYPE/W-TYPE/W-TYPE | 2.44 | 0.07 | 2.21 | 0.06 |
| FAD3A1/FAD3C1/LOLI108/W-TYPE/W-TYPE | 2.02 | 0.05 | 2.50 | 0.03 |
| FAD3A1/FAD3C1/W-TYPE/LOLI111/W-TYPE | 2.22 | 0.03 | 1.51 | 0.14 |
| FAD3A1/FAD3C1/LOLI108/LOLI111/W-TYPE | 1.59 | 0.02 | 1.60 | 0.05 |

These results show that, in line with the previous results, the FAD3A2, FAD3A3 and FAD3C2 mutant alleles further reduce the C18:3 content in lines containing FAD3A1 and FAD3C1 mutant alleles. Moreover, especially in the female line, stacking the FAD3A2 and FAD3A3 mutants in a background with FAD3A1 and FAD3C1 mutants even further reduces the C18:3 content to levels clearly below 2%.

To investigate in more detail the effect of stacking mutants of different FAD3 genes on top of the FAD3A1 and FAD3C1 mutants LOLI105 and LOLI108, the fatty acid composition was determined in lines containing two, three, four or five mutant FAD3 genes. To this end, the lines containing the LOLI105, LOLI103, LOLI108, LOLI111 and LOLI115 alleles were backcrossed three times in elite *Brassica* lines. The progeny plants comprising the mutation were subsequently selfed to obtain homozygous plants, and further crossed with lines containing other mutant FAD3 alleles in order to obtain combinations of different mutants. Oil composition in seeds of these plants upon a second selfing (BC3S2) was analyzed as described above. Table 7 displays the percentage C18:3 of the total oil content.

TABLE 7

Average (Av) and standard deviation (SD) of C18:3 seed oil content percentage (%) in elite male and female crosses upon stacking the the different mutant FAD3 alleles on top of the mutant FAD3A1 and FAD3C1 alleles.

| allele<br>FAD3A1/FAD3C1/FAD3A2/FAD3A3/FAD3C2 | Av<br>C18:3 | SD<br>C18:3 |
|---|---|---|
| W-TYPE/W-TYPE/W-TYPE/W-TYPE/W-TYPE | 4.84 | 0.10 |
| Double mutant | | |
| LOLI105/LOLI103/W-TYPE/W-TYPE/W-TYPE | 2.95 | 0.05 |
| Triple mutants | | |
| LOLI105/LOLI103/LOLI108/W-TYPE/W-TYPE | 2.39 | 0.11 |
| LOLI105/LOLI103/W-TYPE/LOLI111/W-TYPE | 2.23 | 0.04 |
| LOLI105/LOLI103/W-TYPE/W-TYPE/LOLI115 | 2.42 | 0.04 |
| Quadruple mutants | | |
| LOLI105/LOLI103/LOLI108/LOLI111/W-TYPE | 1.48 | 0.01 |
| LOLI105/LOLI103/LOLI108/W-TYPE/LOLI115 | 1.62 | 0.05 |
| LOLI105/LOLI103/W-TYPE/LOLI111/LOLI115 | 1.50 | 0.01 |
| Quintuple mutant | | |
| LOLI105/LOLI103/LOLI108/LOLI111/LOLI115 | 0.80 | 0.02 |

From Table 7, it can be observed that the more mutant alleles of other FAD genes on top of mutant alleles of FAD3A1 and FAD3C1, the lower the C18:3 content. In the quadruple mutants comprising both FAD3A1 and FAD3C1 mutant alleles as well as mutant alleles of two other FAD3 genes, the C18:3 content can be reduced towards about 1.5%, and in the quintuple mutants comprising mutant alleles of FAD3A1, FAD3C1, FAD3A2, FAD3A2 and FAD3C2, the C18:3 oil content can be further reduced to 0.8%.

It is believed that in a background with a higher C18:3 seed oil content than these male and female elite lines, introduction of the LOLI103 allele will also have an additional effect on the C18:3 reduction in seed oil by the FAD3-A1 and/or FAD3-C1 mutant alleles. It is furthermore believed that the more mutant FAD3 alleles will be combined in a plant, the greater the reduction in C18:3 seed oil content will be.

Example 9—Analysis of the Effect of Mutant FAD3 Genes on Fatty Acid Composition in *Brassica* Plants Grown in the Field Tests were set up and are conducted to further analyze the correlation between the presence of mutant FAD3 genes in *Brassica* plants and the C18:3 seed oil content of the *Brassica* plants in the field. Of the *Brassica* plants identified in Example 5 (F1S2), plants comprising a mutant allele of each of the FAD3 genes (LOLI105, LOLI103, LOLI108, LOLI115 and LOLI111) were selfed to obtain homozygous plants. Further crosses between the lines containing the mutant FAD3 genes were made to obtain plants with more than one mutant FAD3 gene. The plants were grown in the field in Belgium (one location) and in Canada (two locations). The fatty acid composition of the seed oil of these plants (nonBC) was determined as described above. Table 8 shows the percentace C18:3 of the total oil of the *Brassica* plants grown in the field in Belgium, and Table 9 shows the percentage of C18:3 of the total oil of the *Brassica* plants grown at two locations in the field Canada.

TABLE 8

Average (Av) and standard deviation (SD) of C18:3 seed oil content percentage (%) in *Brassica* plants with different mutant FAD3 genes grown in the field in Belgium.

| allele FAD3A1/FAD3A2/FAD3A3/FAD3C1/FAD3C2 | Av C18:3 | SD C18:3 |
|---|---|---|
| W-TYPE/W-TYPE/W-TYPE/W-TYPE/W-TYPE | 10.0 | 0.38 |
| Single mutants | | |
| LOLI105/W-TYPE/W-TYPE/W-TYPE/W-TYPE | 7.05 | 0.28 |
| W-TYPE/LOLI108/W-TYPE/W-TYPE/W-TYPE | 9.33 | 0.22 |
| W-TYPE/W-TYPE/LOLI111/W-TYPE/W-TYPE | 8.76 | 0.43 |
| W-TYPE/W-TYPE/W-TYPE/LOLI103/W-TYPE | 7.69 | 0.15 |
| W-TYPE/W-TYPE/W-TYPE/W-TYPE/LOLI115 | 9.71 | 0.25 |
| Double mutants | | |
| LOLI105/W-TYPE/W-TYPE/LOLI103/W-TYPE | 4.10 | 0.10 |
| W-TYPE/LOLI108/W-TYPE/LOLI103/W-TYPE | 6.95 | 0.29 |
| W-TYPE/LOLI108/W-TYPE/W-TYPE/LOLI115 | 9.20 | 0.28 |
| W-TYPE/W-TYPE/LOLI111/LOLI103/W-TYPE | 6.76 | 0.41 |

TABLE 9

Average of C18:3 seed oil content percentage (%) in *Brassica* plants with different mutant FAD3 genes grown at two locations in the field in Canada.

| allele FAD3A1/FAD3A2/FAD3A3/FAD3C1/FAD3C2 | C18:3 |
|---|---|
| W-TYPE/W-TYPE/W-TYPE/W-TYPE/W-TYPE | 12.26 |
| Single mutants | |
| LOLI105/W-TYPE/W-TYPE/W-TYPE/W-TYPE | 9.58 |
| W-TYPE/LOLI108/W-TYPE/W-TYPE/W-TYPE | 11.84 |
| W-TYPE/W-TYPE/W-TYPE/LOLI103/W-TYPE | 9.00 |
| W-TYPE/W-TYPE/W-TYPE/W-TYPE/LOLI115 | 11.98 |
| Double mutants | |
| LOLI105/LOLI108/W-TYPE/W-TYPE/W-TYPE | 8.07 |
| LOLI105/W-TYPE/W-TYPE/LOLI103/W-TYPE | 5.73 |
| LOLI105/W-TYPE/W-TYPE/W-TYPE/LOLI115 | 7.68 |
| W-TYPE/LOLI108/W-TYPE/LOLI103/W-TYPE | 8.23 |
| W-TYPE/LOLI108/W-TYPE/W-TYPE/LOLI115 | 10.62 |
| Triple mutants | |
| LOLI105/LOLI108/W-TYPE/LOLI103/W-TYPE | 4.49 |
| LOLI105/LOLI108/W-TYPE/W-TYPE/LOLI115 | 7.08 |
| W-TYPE/LOLI108/W-TYPE/LOLI103/LOLI115 | 8.12 |
| Quadruple mutant | |
| LOLI105/LOLI108/W-TYPE/LOLI103/LOLI115 | 3.54 |
| LSD | 0.62 |

LSD = Fisher's least significant difference.

Tables 8 and 9 show that, also in the field, seed oil of plants comprising the FAD3-A1 or FADS-C1 mutant alleles in homozygous state, C18:3 seed oil content was reduced as compared to wild-type plants. Plants comprising mutant alleles LOLI108, LOLI111 or LOLI115 in homozygous state show only a minor reduction in C18:3 in seed oil when compared to seed oil from wild type plants. However, similar to in the greenhouse, the LOLI108, LOLI111 and LOLI115 alleles do have an additional effect on the C18:3 reduction in seed oil by the FAD3-A1 and/or FADS-C1 mutant alleles. In addition, it is consistently observed that, for the double and triple mutants, lines comprising both the FAD3A1 and FAD3C1 mutant contain a significantly lower C18:3 seed oil content than other lines containing the same number of mutant FADS alleles. For the triple and quadruple mutants, it can also be observed, in particular when mutant alleles of both FAD3A1 and FAD3C1 are present, that the more mutant FAD3 alleles are stacked in the genome, the further is the reduction in C18:3 content.

Further tests are set up to analyze the correlation between the presence of mutant FAD3 genes in *Brassica* plants and the C18:3 seed oil content of the *Brassica* plants in the field upon further backcrossing with elite *Brassica* lines.

Example 10—Detection and/or Transfer of Mutant FAD3 Alleles into (Elite) *Brassica* Lines The mutant FAD3 genes are transferred into (elite) *Brassica* breeding lines by the following method: A plant containing a mutant FAD3 gene (donor plant), is crossed with an (elite) *Brassica* line (elite parent/recurrent parent) or variety lacking the mutant FAD3 gene. The following introgression scheme is used (the mutant FAD3 allele is abbreviated to fad3 while the wild type is depicted as FAD3):

Initial cross: fad3/fad3 (donor plant)×FAD3/FAD3 (elite parent) F1 plant: FAD3/fad3
BC1 cross: FAD3/fad3×FAD3/FAD3 (recurrent parent) BC1 plants: 50% FAD3/fad3 and 50% FAD3/FAD3
The 50% FAD3/fad3 are selected using molecular markers (e.g. AFLP, PCR, Invader™, TaqMan® and the like; see also below) for the mutant FAD3 allele (fad3).
BC2 cross: FAD3/fad3 (BC1 plant)×FAD3/FAD3 (recurrent parent) BC2 plants: 50% FAD3/fad3 and 50% FAD3/FAD3
The 50% FAD3/fad3 are selected using molecular markers for the mutant FAD3 allele (fad3).
Backcrossing is repeated until BC3 to BC6
BC3-6 plants: 50% FAD3/fad3 and 50% FAD3/FAD3
The 50% FAD3/fad3 are selected using molecular markers for the mutant FAD3 allele (fad3).
To reduce the number of backcrossings (e.g. until BC3 instead of BC6), molecular markers can be used specific for the genetic background of the elite parent.

BC3-6 S1 cross: FAD3/fad3×FAD3/fad3
BC3-6 S1 plants: 25% FAD3/FAD3 and 50% FAD3/fad3 and 25% fad3/fad3
Plants containing fad3 are selected using molecular markers for the mutant FAD3 allele (fad3). Individual BC3-6 S1 or BC3-6 S2 plants that are homozygous for the mutant FAD3 allele (fad3/fad3) are selected using molecular markers for the mutant and the wild-type FAD3 alleles. These plants are then used for seed production.

To select for plants comprising a point mutation in a FAD3 allele, direct sequencing by standard sequencing techniques known in the art, such as those described in Example 4, can be used.

Alternatively, Invader™ technology (Third Wave Agbio) can be used to discriminate plants comprising a specific point mutation in an FAD3 allele from plants not comprising that specific point mutation. Discriminating Invader™ probes were thus developed to detect the presence or absence and the zygosity status of mutant alleles identified in Example 4, in particular of LOLI103, LOLI105, LOLI108, LOLI111 and LOLI115, based on the single nucleotide difference between the mutant and wildtype allele. Briefly, probes specific for the mutant or corresponding wild-type target FAD3 gene (indicated hereinafter as "5' flap1-x1" and "5' flap2-x2", respectively, wherein x1 and x2 represent wildtype and mutant allele-specific sequences) and "invading" probes which can be used in combination with them were developed. Generally, each probe set consists of one probe specific for the mutant or the wild type target gene of which the first nucleotide after the 5' flap sequence matches with the nucleotide difference (the so-called "primary probe") and one probe specific for the nucleotides upstream of the nucleotide difference (the so-called "Invader® oligo"). The last nucleotide of the latter primer may match with the nucleotide difference in the mutant, but other nucleotides may be used as well for this last nucleotide as long as the primary probe and the Invader® oligo are still able to form a single base overlap when hybridized to the target DNA to generate the specific invasive structure recognized by the Cleavase® enzymes (Third Wave Agbio). The Invader™ assay procedure and interpretation of the data are performed as prescribed by the manufacturer (Third Wave Agbio). Briefly, the nucleotide sequences indicated as "flap1" and "flap2" represent the sequences of the 5' "flaps" which are cleaved from the primary probes in the primary phase of the Invader™ assay and which are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target FAD3 gene, respectively. The following discriminating Invader™ assays were thus developed to detect the presence or absence and the zygosity status of the mutant alleles identified in Example 4 (see Table 2):

TABLE 10

Invader probes, forward (Fw) and reverse (Rv) primers. Mutation position is underlined, FAM probe: mutant allele, VIC probe: wild-type allele.

| allele | dye | probe sequence (5'-3') | Fw/Rv | primer sequence (5'-3') |
|---|---|---|---|---|
| LOLI 105 | FAM | TCTTTGTAATGTGATTGGA SEQ ID NO: 18 | Fw | CAGTCACAGTTCTCAAAGTCTATGGAG SEQ ID NO: 20 |
| | VIC | CTTTGTAATGTGGTTGGAC SEQ ID NO: 19 | Rv | TGCCTCTGTACCAAGGCAACTTAT SEQ ID NO: 21 |
| LOLI 103 | FAM | GGATGACTACAGTGATACA SEQ ID NO: 22 | Fw | CCTCTCTATCTGGTAAATCCTAATTCCTAA SEQ ID NO: 24 |
| | VIC | GATGACTACAGTGGTACAGA SEQ ID NO: 23 | Rv | GTATGGGTTATAATGTGACCCTTCTTTAC SEQ ID NO: 25 |
| LOLI 108 | FAM | ATCTTTGTAATGTAGTTGGA SEQ ID NO: 26 | Fw | GGTGTTCCTTACATTGTAAGTTTCACA SEQ ID NO: 28 |
| | VIC | ATCTTTGTAATGTGGTTGGA SEQ ID NO: 27 | Rv | GCCTCTGTACCAAGGCAACTTCT SEQ ID NO: 29 |
| LOLI 111 | FAM | TTACTGCAGTGATACAGAA SEQ ID NO: 30 | Fw | CGCTTACCCGATCTATCTGGTATTT SEQ ID NO: 32 |
| | VIC | TTACTGCAGTGGTACAGA SEQ ID NO: 31 | Rv | GGGTTAAAATGTGACCCTTCTTTTC SEQ ID NO: 33 |
| LOLI 115 | FAM | GACCTTAACTACAGTAGTAC SEQ ID NO: 34 | Fw | ATGCTCGCTTACCCGATCTATTT SEQ ID NO: 36 |
| | VIC | ACCTTAACTACAGTGGTACA SEQ ID NO: 35 | Rv | CTCTCGCTTGGAGCAAATAAACTA SEQ ID NO: 37 |

In conclusion, the current invention is directed at least to the plants, nucleic acid molecules, proteins, plant cells, seeds, oils, methods, uses and kits as described in the following paragraphs:

1. A *Brassica* plant comprising at least two full knock-out mutant FAD3 alleles, wherein
   i. the first full knock-out mutant FAD3 allele is selected from the group consisting of FAD3-A1 or FAD3-C1; and
   ii. the second full knock-out mutant FAD3 allele is selected from the group consisting of FAD3-A2, FAD3-A3 or FAD3-C2.
2. The plant of paragraph 1, further comprising a third full knock-out mutant FAD3 allele, wherein said third full knock-out mutant FAD3 allele is selected from the group consisting of FAD3-A1 or FAD3-C1, whereby the mutant FAD3 alleles are mutant alleles of at least three different FAD3 genes.

3. The plant of paragraph 2, further comprising a fourth full knock-out mutant FAD3 allele, wherein said fourth full knock-out mutant FAD3 allele selected from the group consisting of FAD3-A2, FAD3-A3 or FAD3-C2, whereby the mutant FAD3 alleles are mutant alleles of at least four different FAD3 genes.

4. The plant of paragraph 3, further comprising a fifth full knock-out mutant FAD3 allele, wherein said fifth full knock-out mutant FAD3 allele is selected from the group consisting of FAD3-A2, FAD3-A3 or FAD3-C2, whereby the mutant FAD3 alleles are mutant alleles of at least five different FAD3 genes.

5. The plant of any one of paragraphs 1-4, wherein said full knock-out mutant FAD3 alleles each comprise a nucleotide sequence selected from the group consisting of:
   (a) a nucleotide sequence which comprises at least 90% sequence identity to SEQ ID NO: 1, SEQ ID NO: 3, SEQ ID NO: 5, SEQ ID NO: 7 or SEQ ID NO: 9;
   (b) a nucleotide sequence which comprises at least 90% sequence identity to SEQ ID NO: 11, SEQ ID NO: 12, SEQ ID NO: 13, SEQ ID NO: 14 or SEQ ID NO: 15; or
   (c) a nucleotide sequence encoding an amino acid sequence which comprises at least 90% sequence identity to SEQ ID NO: 2, SEQ ID NO: 4, SEQ ID NO: 6, SEQ ID NO: 8 or SEQ ID NO: 10.

6. The plant of any one of paragraphs 1-5, wherein said full knock-out mutant allele comprises a stop codon mutation 7. The plant of any one of paragraphs 1-6, wherein said full knock-out FAD3 alleles are selected from the group consisting of LOLI105, LOLI103, LOLI108, LOLI111 or LOLI115.

8. The plant of any one of paragraphs 1-7, which produces a significantly reduced amount of functional FAD3 protein compared to the amount of functional FAD3 protein produced by a corresponding plant not comprising said full knock-out FAD3 alleles.

9. The plant of any one of paragraphs 1-8, characterized in that the seed of said plant has a significantly reduced C18:3 content compared to plants not comprising said full knock-out alleles.

10. The plant of any one of paragraphs 1-9 which is homozygous for at least one of said full knock-out mutant FAD3 alleles.

11. A nucleic acid molecule comprising a nucleotide sequence selected from the group consisting of:
    (a) a nucleotide sequence which comprises at least 90% sequence identity to SEQ ID NO: 1, SEQ ID NO: 3, SEQ ID NO: 5, SEQ ID NO: 7 or SEQ ID NO: 9;
    (b) a nucleotide sequence which comprises at least 90% sequence identity to SEQ ID NO: 11, SEQ ID NO: 12, SEQ ID NO: 13, SEQ ID NO: 14 or SEQ ID NO: 15; or
    (c) a nucleotide sequence encoding an amino acid sequence which comprises at least 90% sequence identity to SEQ ID NO: 2, SEQ ID NO: 4, SEQ ID NO: 6, SEQ ID NO: 8 or SEQ ID NO: 10.

12. A full knock-out mutant allele of a FAD3 gene comprising a nucleotide sequence selected from the group consisting of:
    (a) a nucleotide sequence which comprises at least 90% sequence identity to SEQ ID NO: 1, SEQ ID NO: 3, SEQ ID NO: 5, SEQ ID NO: 7 or SEQ ID NO: 9;
    (b) a nucleotide sequence which comprises at least 90% sequence identity to SEQ ID NO: 11, SEQ ID NO: 12, SEQ ID NO: 13, SEQ ID NO: 14 or SEQ ID NO: 15; or
    (c) a nucleotide sequence encoding an amino acid sequence which comprises at least 90% sequence identity to SEQ ID NO: 2, SEQ ID NO: 4, SEQ ID NO: 6, SEQ ID NO: 8 or SEQ ID NO: 10.

13. The full knock-out mutant allele of paragraph 12, which comprises a stop codon mutation.

14. The full knock-out mutant allele of paragraph 13, which is selected from the group consisting of LOLI105, LOLI103, LOLI108, LOLI111 or LOLI115

15. A FAD3 protein encoded by a nucleotide sequence of any one of paragraphs 12-14.

16. A FAD3 protein comprising an amino acid sequence having at least 90% sequence identity to an amino acid sequence selected from the group consisting of SEQ ID NO: 2, SEQ ID NO: 4, SEQ ID NO: 6, SEQ ID NO: 8, or SEQ ID NO: 10.

17. A *Brassica* plant comprising at least one full knock-out mutant allele of a FAD3 gene comprising a nucleotide sequence selected from the group consisting of:
    (a) a nucleotide sequence which comprises at least 90% sequence identity to SEQ ID NO: 1, SEQ ID NO: 3, SEQ ID NO: 5, SEQ ID NO: 7 or SEQ ID NO: 9;
    (b) a nucleotide sequence which comprises at least 90% sequence identity to SEQ ID NO: 11, SEQ ID NO: 12, SEQ ID NO: 13, SEQ ID NO: 14 or SEQ ID NO: 15; or
    (c) a nucleotide sequence encoding an amino acid sequence which comprises at least 90% sequence identity to SEQ ID NO: 2, SEQ ID NO: 4, SEQ ID NO: 6, SEQ ID NO: 8 or SEQ ID NO: 10.

18. The *Brassica* plant of paragraph 17, wherein said full knock-out mutant allele comprises a stop codon mutation 19. The *Brassica* plant of paragraph 17 or 18, wherein said full knock-out mutant allele is selected from the group consisting of LOLI105, LOLI103, LOLI108, LOLI111 or LOLI115

20. A *Brassica* plant comprising a mutant FAD3 protein comprising an amino acid sequence having at least 90% sequence identity to an amino acid sequence selected from the group consisting of SEQ ID NO: 2, SEQ ID NO: 4, SEQ ID NO: 6, SEQ ID NO: 8 or SEQ ID NO: 10.

21. A plant cell, seed, or progeny of the plant of any one of paragraphs 1-10 or 17-20.

22. A seed oil obtainable from the seeds of the plant of any one of paragraphs 1-10 or 17-20.

23. A *Brassica* seed selected from the group consisting of:
    *Brassica* seed comprising FAD3-A1-LOLI105 and FAD3-C1-LOLI103 having been deposited at the NCIMB Limited on Oct. 9, 2009, under accession number NCIMB 41655.
    *Brassica* seed comprising FAD3-A2-LOLI108 and FAD3-C2-LOLI115 having been deposited at the NCIMB Limited on Oct. 9, 2009, under accession number NCIMB 41656.
    *Brassica* seed comprising FAD3-A3-LOLI111 having been deposited at the NCIMB Limited on Oct. 9, 2009, under accession number NCIMB 41657.

24. A *Brassica* plant, or a cell, part, seed or progeny thereof, obtained from the seed of paragraph 23.
25. A method for identifying a mutant FAD3 allele of any one of paragraphs 12-14 in a biological sample comprising determining the presence of a mutant FAD3 specific region in a nucleic acid present in the biological sample.
26. A method for determining the zygosity status of a mutant FAD3 allele of any one of paragraphs 12-14 in a plant, or a cell, part, seed or progeny thereof, comprising determining the presence of a mutant and/or a corresponding wild type FAD3 specific region in the genomic DNA of said plant, or a cell, part, seed or progeny thereof.
27. A method for combining a least two selected mutant FAD3 alleles of any one of paragraphs 12-14 in one plant comprising the steps of:
    (a) identifying at least two plants each comprising at least one selected mutant FAD3 allele according to paragraph 25;
    (b) crossing the at least two plants and collecting F1 hybrid seeds from the at least one cross; and
    (c) optionally, identifying an F1 plant comprising at least two selected mutant FAD3 alleles according to paragraph 25.
28. The method according to paragraph 27, which further comprises the step of identifying an F1 plant, which is homozygous or heterozygous for a selected mutant FAD3 allele by determining the zygosity status of the selected mutant FAD3 allele according to paragraph 26.
29. A method for transferring at least one selected mutant FAD3 allele from one plant to another plant comprising the steps of:
    (a) identifying a first plant comprising at least one selected mutant FAD3 allele according to any one of paragraphs 12-14 or generating a first plant comprising at least two selected mutant FAD3 alleles according to paragraph 27 or 28;
    (b) crossing the first plant with a second plant not comprising the at least one selected mutant FAD3 allele and collecting F1 hybrid seeds from the cross,
    (c) optionally, identifying F1 plants comprising the at least one selected mutant FAD3 allele according to paragraph 25;
    (d) backcrossing F1 plants comprising the at least one selected mutant FAD3 allele with the second plant not comprising the at least one selected mutant FAD3 allele for at least one generation (x) and collecting BCx seeds from the crosses; and
    (e) identifying in every generation BCx plants comprising the at least one selected mutant FAD3 allele according to paragraph 25.
30. The method according to paragraph 29, which further comprises the step of identifying a BCx plant, which is homozygous or heterozygous for a selected mutant FAD3 allele by determining the zygosity status of the selected mutant FAD3 allele, according to paragraph 26.
31. A method for producing a plant of any one of paragraphs 1-10 or 17-20 comprising combining and/or transferring mutant FAD3 alleles of any one of paragraphs 12-14 in or to one *Brassica* plant, according to any one of paragraphs 27-30.
32. A method to reduce the C18:3 content in the seed oil of a *Brassica* plant comprising combining at least two full knock-out FAD3 alleles in the genomic DNA of said plant, wherein
    i. the first full knock-out mutant FAD3 allele is selected from the group consisting of FAD3-A1 or FAD3-C2; and
    ii. the second full knock-out mutant FAD3 allele is selected from the group consisting of FAD3-A2, FAD3-A3 or FAD3-C2.
33. The method of paragraph 32, wherein said plant further comprises a third full knock-out mutant FAD3allele, said third full knock-out mutant FAD3 allele being selected from the group consisting of FAD3-A1 or FAD3-C1, whereby the mutant FAD3 alleles are mutant alleles of at least three different FAD3 genes.
34. The method of paragraph 33, wherein said plant further comprises a fourth full knock-out mutant FAD3 allele, said fourth full knock-out mutant FAD3 allele being selected from the group consisting of FAD3-A2, FAD3-A3 or FAD3-C2, whereby the mutant FAD3 alleles are mutant alleles of at least four different FAD3 genes.
35. The method of paragraph 34, wherein said plant further comprises a fifth full knock-out mutant FAD3 allele, said fifth full knock-out mutant FAD3 allele being selected from the group consisting of FAD3-A2, FAD3-A3 or FAD3-C2, whereby the mutant FAD3 alleles are mutant alleles of at least five different FAD3 genes.
36. The method of any one of paragraphs 32-35, wherein said full knock-out mutant FAD3 alleles each comprise a nucleotide sequence selected from the group consisting of:
    (a) a nucleotide sequence which comprises at least 90% sequence identity to SEQ ID NO: 1, SEQ ID NO: 3, SEQ ID NO: 5, SEQ ID NO: 7 or SEQ ID NO: 9;
    (b) a nucleotide sequence which comprises at least 90% sequence identity to SEQ ID NO: 11, SEQ ID NO: 12, SEQ ID NO: 13, SEQ ID NO: 14 or SEQ ID NO: 15; or
    (c) a nucleotide sequence encoding an amino acid sequence which comprises at least 90% sequence identity to SEQ ID NO: 2, SEQ ID NO: 4, SEQ ID NO: 6, SEQ ID NO: 8 or SEQ ID NO: 10.
37. The method of any one of paragraphs 32-36, wherein said full knock-out mutant allele comprises a stop codon mutation.
38. The method of any one of paragraphs 32-37, wherein said full knock-out FAD3 alleles are selected from the group consisting of LOLI105, LOLI103, LOLI108, LOLI111 or LOLI115.
39. Use of a plant comprising one or more mutant FAD3 alleles of any one of paragraphs 12-14 according to the methods of any one of paragraphs 25-38.
40. Use of a mutant FAD3 allele of any one of paragraphs 12-14 to reduce the C18:3 content in the seed oil of a *Brassica* plant.
41. Use of the plant of any one of paragraphs 1-10, 17-20 or 24 to produce oilseed rape oil or an oilseed rape seed cake.
42. Use of the seeds of paragraph 21 or 23 to produce oilseed rape oil or an oilseed rape seed cake.
43. Use of the plant of any one of paragraphs 1-10 or 17-20 to produce seed comprising one or more mutant FAD3 alleles.
44. Use of the plant of any one of paragraphs 1-10 or 17-20 to produce a crop of oilseed rape, comprising one or more mutant FAD3 alleles.

45. A kit for identifying a mutant FAD3 allele of one of paragraph 12-14 in a biological sample, comprising a set of primers or probes, said set selected from the group consisting of:
a set of primers or probes, wherein one of said primers or probes specifically recognizes the 5' flanking region of the mutant FAD3 allele and the other of said primers or probes specifically recognizes the 3' flanking region of the mutant FAD3 allele;
a set of primers or probes, wherein one of said primers or probes specifically recognizes the 5' or 3' flanking region of the mutant FAD3 allele and the other of said primers or probes specifically recognizes the mutation region of the mutant FAD3 allele;
a set of primers or probes, wherein one of said primers specifically recognizes the 5' or 3' flanking region of the mutant FAD3 allele and the other of said primers or probes specifically recognizes the joining region between the 3' or 5' flanking region and the mutation region of the mutant FAD3 allele, respectively; or
a probe which specifically recognizes the joining region between the 5' or 3' flanking region and the mutation region of the mutant FAD3 allele.

46. A kit for determining the zygosity status of a mutant FAD3 allele of any one of paragraphs 12-14 in a plant, or a cell, part, seed or progeny thereof, comprising a set of primers or probes, wherein at least two of said primers or at least one of said probes specifically recognize the wild type FAD3 allele and wherein at least two of said primers or at least one of said probes specifically recognize the mutant FAD3 allele, selected from the group consisting of:
a set of at least two primers or probes, wherein a first primer or probe specifically recognizes the 5' flanking region of the mutant and the wild type FAD3 allele and a second primer or probe specifically recognizes the 3' flanking region of the mutant and the wild type FAD3 allele;
a set of at least three primers or probes, wherein a first primer or probe specifically recognizes the 5' or 3' flanking region of the mutant and the wild type FAD3 allele, a second primer or probe specifically recognizes the mutation region of the mutant FAD3 allele, and a third primer or probe specifically recognizes the mutation region of the wild type FAD3 allele;
a set of at least three primers or probes, wherein a first primer or probe specifically recognizes the 5' or 3' flanking region of the mutant and the wild type FAD3 allele, a second primer or probe specifically recognizes the joining region between the 3' or 5' flanking region and the mutation region of the mutant FAD3 allele, respectively, and a third primer or probe specifically recognizes the joining region between the 3' or 5' flanking region and the mutation region of the wild type FAD3 allele, respectively; or
a set of at least two probes, wherein a first probe specifically recognizes the joining region between the 5' or 3' flanking region and the mutation region of the mutant FAD3 allele and a second probe specifically recognizes the joining region between the 5' or 3' flanking region and the mutation region of the wild type FAD3 allele.

The invention claimed is:

1. A *Brassica* plant comprising at least two endogenous full knock-out mutant FAD3 alleles, wherein
   i. the first full knock-out mutant FAD3 allele is a full knock-out mutant FAD3 allele of a FAD3 gene, said FAD3 gene is FAD3-A1 or FAD3-C1, wherein
      (a) said FAD3-A1 gene comprises a nucleotide sequence comprising at least 95% sequence identity to SEQ ID NO: 1, or has a coding region comprising at least 95% sequence identity to SEQ ID NO: 11, or encodes a protein comprising at least 95% sequence identity to SEQ ID NO: 2; and
      (b) said FAD3-C1 gene comprises a nucleotide sequence comprising at least 95% sequence identity to SEQ ID NO: 3, or has a coding region comprising at least 95% sequence identity to SEQ ID NO: 12, or encodes a protein comprising at least 95% sequence identity to SEQ ID NO: 4; and
      wherein said full knock-out mutant FAD3 allele of said FAD3-A1 gene comprises a nucleotide sequence which comprises at least 90% sequence identity to SEQ ID NO: 1, and wherein said full knock-out mutant FAD3 allele of said FAD3-C1 gene comprises a nucleotide sequence which comprises at least 90% sequence identity to SEQ ID NO: 3; and
   ii. the second full knock-out mutant FAD3 allele is a full knock-out mutant FAD3 allele of a FAD3 gene, said FAD3 gene is FAD3-A2, FAD3-A3 or FAD3-C2, wherein
      (a) said FAD3-A2 gene comprises a nucleotide sequence comprising at least 95% sequence identity to SEQ ID NO: 5, or has a coding region comprising at least 95% sequence identity to SEQ ID NO: 13, or encodes a protein comprising at least 95% sequence identity to SEQ ID NO: 6;
      (b) said FAD3-A3 gene comprises a nucleotide sequence comprising at least 95% sequence identity to SEQ ID NO: 7, or has a coding region comprising at least 95% sequence identity to SEQ ID NO: 14, or encodes a protein comprising at least 95% sequence identity to SEQ ID NO: 8; and
      (c) said FAD3-C2 gene comprises a nucleotide sequence comprising at least 95% sequence identity to SEQ ID NO: 9, or has a coding region comprising at least 95% sequence identity to SEQ ID NO: 15, or encodes a protein comprising at least 95% sequence identity to SEQ ID NO: 10;

wherein said full knock-out mutant FAD3 allele of said FAD3-A2 gene comprises a nucleotide sequence which comprises at least 90% sequence identity to SEQ ID NO: 5, wherein said full knock-out mutant FAD3 allele of said FAD3-A3 gene comprises a nucleotide sequence which comprises at least 90% sequence identity to SEQ ID NO: 7, and wherein said full knock-out mutant FAD3 allele of said FAD3-C2 gene comprises a nucleotide sequence which comprises at least 90% sequence identity to SEQ ID NO: 9;

wherein each of said full knock-out mutant FAD3 allele comprises one or more nucleotide deletions, insertions or substitutions relative to the wild type nucleic acid sequences, wherein the mutations result in a completely abolished biological activity of the encoded FAD3 protein relative to the wild type protein, and wherein each of said full knock-out mutant FAD3 allele comprises a. a deletion, frameshift or stop-codon mutation that leads to an entire deletion of the encoded FAD3 protein;

b. a stop-codon, frameshift or splice site mutation leading to a disruption or deletion of the ER retention motif at a position corresponding to position 373-377 of SEQ ID NO: 2 of the encoded protein;

c. a missense, insertion or deletion mutation in the sequence encoding the ER retention motif at a position corresponding to position 373-377 of SEQ ID NO: 2 of the encoded protein;

d. a missense mutation in the codon encoding any of the conserved histidines at a position corresponding to position 92, 96, 128, 131, 132, 295, 298 or 299 of SEQ ID NO: 2 of the encoded protein;

e. an insertion, deletion or splice site mutation that deletes or disrupts any one of the eight conserved histidine residues at a position corresponding to position 92, 96, 128, 131, 132, 295, 298 or 299 of SEQ ID NO: 2 of the encoded protein; or f. a nonsense mutation which results in a change of the position of the start ATG codon thereby encoding an N-terminally truncated protein lacking the signal sequence; and wherein said *Brassica* plant is homozygous for each of said full knock-out mutant FAD3 allele.

2. The plant of claim 1, further comprising a third, or a third and a fourth, or a third, a fourth and a fifth endogenous full knock-out mutant FAD3 allele, wherein said third full knock-out mutant FAD3 allele is a full knock-out mutant FAD3 allele of said FAD3-A1 gene or said FAD3-C1 gene, and wherein said fourth and said fifth full knock-out mutant FAD3 alleles are a full knock-out mutant FAD3 allele of said FAD3-A2 gene, said FAD3-A3 gene, or said FAD3-C2 gene, and whereby said full knock-out mutant FAD3 alleles are mutant alleles of different FAD3 genes.

3. The plant of claim 1 or 2, wherein said full knock-out FAD3 allele of said FAD3-A1 gene is LOLI105, said full knock-out FAD3 allele of said FAD3-C1 gene is LOLI103, said full knock-out FAD3 allele of said FAD3-A2 gene is LOLI108, said full knock-out FAD3 allele of said FAD3-A3 gene is LOLI111, and/or said full knock-out FAD3 allele of said FAD3-C2 gene is LOLI115.

4. A full knock-out mutant allele of a FAD3 gene, said mutant allele is:

i. a mutant allele having the sequence of SEQ ID NO: 5 wherein the G at position 3934 is substituted with A, ii. a mutant allele having the sequence of SEQ ID NO: 7 wherein the G at position 2847 is substituted with A; or iii. a mutant allele having the sequence of SEQ ID NO: 9 wherein the G at position 3909 is substituted with A.

5. A plant cell, seed, or progeny of the plant of any one of claim 1 or 2, wherein said plant cell, seed, or progeny comprises the at least two full knock-out FAD3 alleles.

6. The *Brassica* plant according to claim 3, which is obtainable from a:

*Brassica* seed comprising FAD3-A1-LOLI105 and FAD3-C1-LOLI103 having been deposited at the NCIMB Limited on Oct. 9, 2009, under accession number NCIMB 41655;

*Brassica* seed comprising FAD3-A2-LOLI108 and FAD3-C2-LOLI115 having been deposited at the NCIMB Limited on Oct. 9, 2009, under accession number NCIMB 41656; or

*Brassica* seed comprising FAD3-A3-LOLI111 having been deposited at the NCIMB Limited on Oct. 9, 2009, under accession number NCIMB 41657.

7. A method for determining the zygosity status of a *Brassica* plant, or a cell, part, seed or progeny thereof comprising at least two endogenous full knock-out mutant FAD3 alleles as described in claim 1, said method comprising determining the presence of a mutant and a corresponding wild type FAD3 specific region in the genomic DNA that serve as control of said plant, or a cell, part, seed or progeny thereof, said method comprising subjecting the genomic DNA of said plant, or a cell, part, seed or progeny thereof, to a polymerase chain reaction assay using two primers specifically recognizing the mutant FAD3 allele and two primers that serve as control to specifically recognize the wild-type FAD3 allele, or a hybridization based assay using at least one probe specifically recognizing the mutant FAD3 allele and at least one probe that serve as control to specifically recognize the wild-type FAD3 allele.

8. A method for combining at least two endogenous full knock-out mutant FAD3 alleles as described in claim 1 in one plant comprising:

(a) identifying at least two plants each comprising at least one full knock-out mutant FAD3 allele by determining the zygosity status of the at least one selected mutant FAD3 allele;

(b) crossing the at least two plants and collecting F1 hybrid seeds from the crossing; and (c) optionally, identifying an F1 plant comprising at least two full knock-out mutant FAD3 alleles by determining the zygosity status of the at least two full knock-out mutant FAD3 alleles.

9. A method to reduce the C18:3 content in the seed oil of a *Brassica* plant comprising combining at least two endogenous full knock-out FAD3 alleles in the genomic DNA of said plant, wherein:

i. the first full knock-out mutant FAD3 allele is a full knock-out mutant FAD3 allele of a FAD3 gene, said FAD3 gene is FAD3-A1 or FAD3-C1, wherein (a) said FAD3-A1 gene comprises a nucleotide sequence comprising at least 95% sequence identity to SEQ ID NO: 1, or has a coding region comprising at least 95% sequence identity to SEQ ID NO: 11, or encodes a protein comprising at least 95% sequence identity to SEQ ID NO: 2; and (b) said FAD3-C1 gene comprises a nucleotide sequence comprising at least 95% sequence identity to SEQ ID NO: 3, or has a coding region comprising at least 95% sequence identity to SEQ ID NO: 12, or encodes a protein comprising at least 95% sequence identity to SEQ ID NO: 4; and wherein said full knock-out mutant FAD3 allele of said FAD3-A1 gene comprises a nucleotide sequence which comprises at least 90% sequence identity to SEQ ID NO: 1, and wherein said full knock-out mutant FAD3 allele of said FAD3-C1 gene comprises a nucleotide sequence which comprises at least 90% sequence identity to SEQ ID NO: 3; and ii. the second full knock-out mutant FAD3 allele is a full knock-out mutant FAD3 allele of a FAD3 gene, said FAD3 gene is FAD3-A2, FAD3-A3 and FAD3-C2, wherein (a) said FAD3-A2 gene comprises a nucleotide sequence comprising at least 95% sequence identity to SEQ ID NO: 5, or has a coding region comprising at least 95% sequence identity to SEQ ID NO: 13, or encodes a protein comprising at least 95% sequence identity to SEQ ID NO: 6;

(b) said FAD3-A3 gene comprises a nucleotide sequence comprising at least 95% sequence identity to SEQ ID NO: 7, or has a coding region comprising at least 95% sequence identity to SEQ ID NO: 14, or encodes a protein comprising at least 95% sequence identity to SEQ ID NO: 8; and (c) said FAD3-C2 gene comprises a nucleotide sequence comprising at least 95% sequence identity to SEQ ID NO: 9, or has a coding region comprising at least 95% sequence identity to SEQ ID NO: 15, or encodes a protein comprising at least 95% sequence identity to SEQ ID NO: 10; and wherein said full knock-out mutant FAD3 allele of said FAD3-A2 gene comprises a nucleotide sequence which comprises at least 90% sequence identity to SEQ ID NO: 5, wherein said full knock-out mutant FAD3 allele of said FAD3-A3 gene comprises a nucleotide sequence which comprises at least 90% sequence identity to SEQ ID NO: 7, and wherein said full knock-out mutant FAD3 allele of said FAD3-C2 gene comprises a nucleotide sequence which comprises at least 90% sequence identity to SEQ ID NO: 9; and wherein each of said full knock-out mutant FAD3 allele comprises one or more nucleotide deletions, insertions or substitutions relative to the wild type nucleic acid sequences, wherein the mutations result in a completely abolished biological activity of the encoded FAD3 protein relative to the wild type protein, and wherein each of said full knock-out mutant FAD3 allele comprises a. a deletion, frameshift or stop-codon mutation that leads to an entire deletion of the encoded FAD3 protein;

b. a stop-codon, frameshift or splice site mutation leading to a disruption or deletion of the ER retention motif at a position corresponding to position 373-377 of SEQ ID NO: 2 of the encoded protein;

c. a missense, insertion or deletion mutation in the sequence encoding the ER retention motif at a position corresponding to position 373-377 of SEQ ID NO: 2 of the encoded protein;

d. a missense mutation in the codon encoding any of the conserved histidines at a position corresponding to position 92, 96, 128, 131, 132, 295, 298 or 299 of SEQ ID NO: 2 of the encoded protein;

e. an insertion, deletion or splice site mutation that deletes or disrupts any one of the eight conserved histidine residues at a position corresponding to position 92, 96, 128, 131, 132, 295, 298 or 299 of SEQ ID NO: 2 of the encoded protein; or f. a nonsense mutation which results in a change of the position of the start ATG codon thereby encoding an N-terminally truncated protein lacking the signal sequence, wherein said Brassica plant is homozygous for each of said full knock-out mutant FAD3 allele.

10. The method of claim 9, wherein said plant further comprises a third, or a third and a fourth, or a third, a fourth and a fifth full knock-out mutant FAD3 allele, said third full knock-out mutant FAD3 allele being a full knock-out mutant FAD3 allele of said FAD3-A1 gene or a full knock-out FAD3 allele of said FAD3-C1 gene, and said fourth and said fifth full knock-out mutant FAD3 alleles being a full knock-out mutant FAD3 allele of a said FAD3-A2 gene, a full knock-out FAD3 allele of said FAD3-A3 gene, or a full knock-out FAD3 allele of said FAD3-C2 gene, whereby said full knock-out mutant FAD3 alleles are mutant alleles of different FAD3 genes.

11. The method of claim 9 or 10, wherein said full knock-out FAD3 allele of said FAD3-A1 gene is LOLI105, said full knock-out FAD3 allele of said FAD3-C1 gene is LOLI103, said full knock out FAD3-A2 gene is LOLI108, said full knock-out FAD3 allele of said FAD3-A3 gene is LOLI111, and/or said full knock-out FAD3 allele of said FAD3-C2 gene is LOLI115.

12. A method to produce oilseed rape oil or an oilseed rape seed cake, said method comprising planting the seeds of claim 5, and growing progeny from said seeds.

13. A method to produce seed oil comprising crushing seeds of the plants of any one of claim 1 or 2.

14. The Brassica plant according to claim 1, wherein said second full knock-out mutant FAD3 allele is said full knock-out mutant FAD3 allele of said FAD3-A2 gene or said full knock-out mutant FAD3 allele of said FAD3-A3 gene.

15. The method of claim 7, wherein said first full knock-out mutant FAD3 allele is LOLI105 or LOLI103, and wherein said second full knock-out mutant FAD3 allele is LOLI108, LOLI111, or LOLI115.

16. The method of claim 8, wherein said first full knock-out mutant FAD3 allele is LOLI105 or LOLI103, and wherein said second full knock-out mutant FAD3 allele is LOLI108, LOLI111, or LOLI115.

17. The plant of claim 1, wherein said plant has a reduced level of C18:3 as compared to a plant not comprising said at least two endogenous full knock-out mutant FAD3 alleles.

18. The full knock-out mutant allele of a FAD3 gene of claim 4, said mutant allele is:

i. a mutant allele having the sequence of SEQ ID NO: 5 wherein the G at position 3934 is substituted with A, or ii. a mutant allele having the sequence of SEQ ID NO: 7 wherein the G at position 2847 is substituted with A.

19. The Brassica plant of claim 1, wherein the second full knock-out mutant FAD3 allele is said full knock-out mutant FAD3 allele of said FAD3-A3 gene.

20. The Brassica plant of claim 2, comprising three full knockout mutant FAD3 alleles, wherein the third full knock-out mutant FAD3 allele is said full knock-out mutant FAD3 allele of said FAD3-A1 gene or said full knock-out mutant FAD3 allele of said FAD3-C1 gene, whereby the mutant FAD3 alleles are mutant alleles of at least three different FAD3 genes.

21. The *Brassica* plant of claim 2, comprising four full knockout mutant FAD3 alleles, wherein the third full knock-out mutant FAD3 allele is said full knock-out mutant FAD3 allele of said FAD3-A1 gene or said full knock-out mutant FAD3 allele of said FAD3-C1 gene, and the fourth full knock-out mutant FAD3 allele is said full knock-out mutant FAD3 allele of said FAD3-A2 gene, said full knock-out mutant FAD3 allele of said FAD3-A3 gene, or said full knock-out mutant FAD3 allele of said FAD3-C2 gene, whereby the mutant FAD3 alleles are mutant alleles of at least four different FAD3 genes.

22. The *Brassica* plant of claim 21, wherein the first full knockout mutant FAD3 allele is said full knock-out mutant FAD3 allele of said FAD3-A1 gene, said third full knockout mutant FAD3 allele is said full knock-out mutant FAD3 allele of said FAD3-C1 gene, said second full knockout mutant FAD3 allele is said full knock-out mutant FAD3 allele of said FAD3-A2 gene, and said fourth full knockout mutant FAD3 allele is said full knock-out mutant FAD3 allele of said FAD3-A3 gene.

23. The method of claim 9, wherein the second full knock-out mutant FAD3 allele is said full knock-out mutant FAD3 allele of said FAD3-A3 gene.

24. The method of claim 10, comprising combining three full knockout mutant FAD3 alleles, wherein the third full knock-out mutant FAD3 allele is said full knock-out mutant FAD3 allele of said FAD3-A1 gene or said full knock-out mutant FAD3 allele of said FAD3-C1 gene, whereby the mutant FAD3 alleles are mutant alleles of at least three different FAD3 genes.

25. The method of claim 10, comprising combining four full knockout mutant FAD3 alleles, wherein the third full knock-out mutant FAD3 allele is said full knock-out mutant FAD3 allele of said FAD3-A1 gene or said full knock-out mutant FAD3 allele of said FAD3-C1 gene, and the fourth full knock-out mutant FAD3 allele is said full knock-out mutant FAD3 allele of said FAD3-A2 gene, FAD3-A3, or said full knock-out mutant FAD3 allele of said FAD3-C2 gene, whereby the mutant FAD3 alleles are mutant alleles of at least four different FAD3 genes.

26. The method of claim 25, wherein said first knockout mutant FAD3 allele is said a full knock-out mutant FAD3 allele of said FAD3-A1 gene, said third full knockout mutant FAD3 allele is said full knock-out mutant FAD3 allele of said FAD3-C1 gene, said second full knockout mutant FAD3 allele is said full knock-out mutant FAD3 allele of said FAD3-A2 gene, and said fourth full knockout mutant FAD3 allele is said full knock-out mutant FAD3 allele of said FAD3-A3 gene.

* * * * *